United States Patent [19]

Matsumura et al.

[11] Patent Number: 5,269,965
[45] Date of Patent: Dec. 14, 1993

[54] OPTICALLY ACTIVE COMPOUNDS, LIQUID CRYSTAL COMPOSITIONS COMPRISING SAID COMPOUNDS AND LIQUID CRYSTAL OPTICAL MODULATORS USING SAID COMPOSITIONS

[75] Inventors: Koichi Matsumura, Ibaraki; Mitsuru Kawada, Amagasaki; Yoshitaka Uesugi, Ohtsu; Yuka Sudo, Kasama; Katsumi Kondo; Teruo Kitamura, both of Katsuta, all of Japan

[73] Assignees: Takeda Chemical Industries, Osaka; Hitachi, Ltd., Tokyo, both of Japan

[21] Appl. No.: 47,629

[22] Filed: Apr. 15, 1993

Related U.S. Application Data

[63] Continuation of Ser. No. 457,841, Dec. 27, 1989, abandoned.

[30] Foreign Application Priority Data

Dec. 28, 1988 [JP] Japan .................. 63-335239

[51] Int. Cl.$^5$ ............... C09K 19/30; C09K 19/34; C07C 239/02; C07C 69/76
[52] U.S. Cl. ............ 252/299.63; 252/299.61; 252/299.65; 252/299.66; 252/299.67; 544/302; 544/305; 544/310; 560/9; 560/19; 560/61; 560/76; 560/87
[58] Field of Search .............. 252/299.01, 299.61, 252/299.63, 299.64, 299.65, 299.66, 299.67; 544/302, 305, 310; 560/9, 17, 18, 59, 61, 73, 76, 84, 87, 122; 568/631

[56] References Cited

U.S. PATENT DOCUMENTS 4,650,600  3/1987  Heppke et al. ............... 252/299.01

List continued on next page

FOREIGN PATENT DOCUMENTS 0138006  4/1985  European Pat. Off. .

List continued on next page

OTHER PUBLICATIONS

Tetrahedron Letters, No. 6, pp. 419-422, 1976, Rosenblum et al.
Tetrahedron Letters, vol. 37, No. 12, pp. 2249-2254, 1981, Bystrom et al.
Patent Abstracts of Japan, vol. 13, No. 151.
Patent Abstracts of Japan, vol. 13, No. 278.
Patent Abstracts of Japan, unexamined applications, vol. 7, No. 131, pp. 156, C169, 1983.

*Primary Examiner*—Robert L. Stoll
*Assistant Examiner*—Shean C. Wu
*Attorney, Agent, or Firm*—Antonelli, Terry, Stout & Kraus

[57] ABSTRACT

The invention relates to optically active compounds represented by the general formula

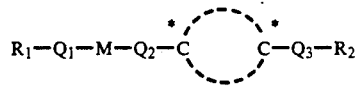

wherein $R_1$, $R_2$, $Q_1$, $Q_2$, $Q_3$,

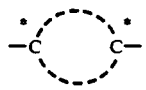

and M are defined as in the specification, methods and intermediates for their preparation, liquid crystal compositions comprising at least one optically active compound of formula I and their use in electrooptical display, switching and modulation devices.

28 Claims, 1 Drawing Sheet

U.S. PATENT DOCUMENTS

| | | | |
|---|---|---|---|
| 4,873,019 | 10/1989 | Krause et al. | 252/299.61 |
| 4,943,384 | 7/1990 | Sucrow et al. | 252/299.61 |
| 5,013,475 | 5/1991 | Shibata et al. | 252/299.61 |
| 5,100,579 | 3/1992 | Higuchi et al. | 252/299.65 |
| 5,130,048 | 7/1992 | Wand et al. | 252/299.01 |
| 5,152,919 | 10/1992 | Kitamura et al. | 252/299.61 |
| 5,167,855 | 12/1992 | Wand et al. | 252/299.01 |
| 5,167,863 | 12/1992 | Kitamura et al. | 252/299.65 |

FOREIGN PATENT DOCUMENTS

| | | |
|---|---|---|
| 0257457 | 3/1988 | European Pat. Off. . |
| 3333677 | 9/1983 | Fed. Rep. of Germany . |
| 3534777 | 9/1985 | Fed. Rep. of Germany . |
| 3604899 | 2/1986 | Fed. Rep. of Germany . |
| 3739588 | 7/1988 | Fed. Rep. of Germany . |
| 253632 | 1/1988 | German Democratic Rep. . |
| 86/05484 | 9/1986 | Int'l Pat. Institute . |
| 60-168780 | 2/1985 | Japan . |
| 60-218358 | 11/1985 | Japan . |
| 61-68449 | 4/1986 | Japan . |
| 62-46 | 1/1987 | Japan . |
| 62-30740 | 2/1987 | Japan . |
| 62-103043 | 5/1987 | Japan . |
| 62-111950 | 5/1987 | Japan . |
| 62-142131 | 6/1987 | Japan . |
| 62-175443 | 8/1987 | Japan . |
| 62-228036 | 10/1987 | Japan . |
| 63-307837 | 12/1988 | Japan . |
| 1-75449 | 3/1989 | Japan . |

F I G. 1
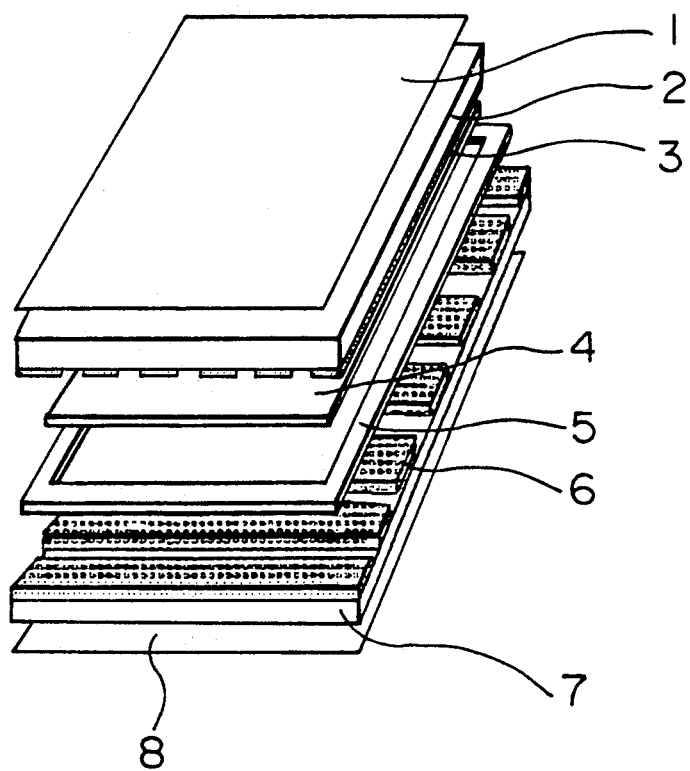

OPTICALLY ACTIVE COMPOUNDS, LIQUID CRYSTAL COMPOSITIONS COMPRISING SAID COMPOUNDS AND LIQUID CRYSTAL OPTICAL MODULATORS USING SAID COMPOSITIONS

This application is a continuation application of application Ser. No. 457,841, filed Dec. 27, 1989, now abandoned.

BACKGROUND OF THE INVENTION

1. Field of the Invention

The present invention relates to novel optically active compounds and liquid crystal compositions comprising said compounds. The present invention provides, in particular, ferroelectric liquid crystal materials, for example, optically active compounds and liquid crystal compositions comprising said compounds both useful as electrooptic switching elements (e.g. liquid crystal display devices) in liquid crystal optical modulators, as well as liquid crystal optical modulators using liquid crystal compositions comprising said compounds.

2. Related Art Statement

Liquid crystal display devices have various excellent features such as low-voltage operability, lower electricity consumption, being thin and light-weight, being a non-emissive type and easy on the eye, etc. Accordingly, they are in wide use as various display devices.

Liquid crystal display devices using a nematic liquid crystal operating in the so-called twisted nematic mode (TN mode) are in use currently. However, display devices using this kind of nematic liquid crystal have the drawback of being very slow in response as compared to luminescent type display devices such as CRT, EL and the like. When the liquid crystal display devices using a nematic liquid crystal are applied in a large-scale display device capable of displaying a large amount of information, it is impossible to obtain a display of good contrast because of insufficient threshold characteristic. Thus the liquid crystal display devices using a nematic liquid crystal have had a limitation for wide application. There has recently been developed a liquid crystal display device using a nematic liquid crystal operating in the so-called super twisted nematic mode (STN mode) or SBE and capable of giving a display of improved contrast because of improved threshold characteristic. Even in this STN mode liquid crystal display device, however, the response is not sufficiently improved, and therefore said device has a limitation for application to displays capable of displaying a still larger amount of information. Hence, various attempts have been made to develop a new liquid crystal display system which is applicable to large-scale displays capable of displaying a large amount of information.

Ferroelectric liquid crystals have a memory characteristic and give a high speed response, and accordingly their application to large-scale displays is highly expected. As liquid crystals having ferroelectric properites, there are known those showing a chiral smectic C phase, a chiral smectic H phase, a chiral smectic J phase, etc. Of these ferroelectric liquid crystals, those showing a chiral smectic C phase are thought to have highest practical utility. Ferroelectric liquid crystals showing a chiral smectic C phase were first synthesized in 1975 by R. B. Meyer et al.; one typical example thereof is 2-methylbutyl 4-(4'-n-decyloxybenzylideneamino)cinnamate (hereinafter abbreviated to DOBAMBC) [J. Physique, 36, L-69 (1975)]. A thin film liquid crystal cell was prepared using DOBAMBC and was found to have a high speed response in the order of $\mu$sec and a memory characteristic [N. A. Clark et al., Appl. Phys. Lett., 36, 89 (1980)].

Since that time, there was started the development of optical modulation devices (e.g. liquid crystal display devices, photo-printer heads) using a ferroelectric liquid crystal showing a chiral smectic C phase (hereinafter may be referred to simply as "ferroelectric liquid crystal").

As a result, a number of ferroelectric liquid crystal compounds showing a chiral smectic C phase have been developed since then, and various ferroelectric liquid crystal compounds are already known. However, no ferroelectric liquid crystal compound is found yet which has satisfactory reliability and capability for use in large-scale displays, etc.

In order for a ferroelectric liquid crystal to be practically used in a liquid crystal display device, etc., the liquid crystal must be superior in high speed response, orientation, memory characteristic, characteristic of threshold voltage, temperature dependences of these properties, etc. Also, the ferroelectric liquid crystal is required to show a chiral smectic C phase over a wide temperature change so that it can operate within a sufficiently wide temperature range including room temperature, and further to have excellent physical and chemical stabilities.

Of these requirements, particularly important are physical and chemical stabilities and stable expression of high speed response and memory characteristic.

It is reported by Clark et al. based on their experiment that a response in the order of $\mu$sec is possible under certain conditions. However, even if the conditions used by Clark et al. could have materialized a large-scale display capable of displaying a large amount of information, i.e. a display having a very large number of pixels, the display must show a faster response.

The response time ($\tau$) of a ferroelectric liquid crystal is approximately given by the following formula when a torque generated by the dielectric anisotropy and an external electric field is neglected.

$$\tau = \eta/PsE$$

($\tau$ is a response time, $\eta$ is a viscosity coefficient, Ps is a spontaneous polarization, and E is an applied electric field). Therefore, increase in spontaneous polarization is effective to obtain a faster (shorter time) response.

Meanwhile, memory characteristic is considered to improve dependently upon the value of spontaneous polarization. Increase in spontaneous polarization gives rise to increase in polarization electric field, which brings about uniformity of dipole moment, i.e. stabilization of memory condition.

Thus, increase in spontaneous polarization is very effective for the simultaneous solution of the two tasks perculiar to ferroelectric liquid crystals. Hence, development of ferroelectric liquid crystal compounds with increased spontaneous polarization has recently been pushed forward. As a result, there have been reported, for example, ferroelectric liquid crystal compounds of ester type using, as an optically active group, (R)- or (S)-1-methyl butanol or (R)- or (S)-1-methylheptanol, which are stable physically and chemically [K. Terashima et al., Mol. Cryst. Liq. Cryst., 141, 237 (1986)]. These compounds have a relatively high spontaneous polarization of 50 nC/cm² or more, but the value is not sufficient.

In order to obtain a larger spontaneous polarization, there have been synthesized compounds having two asymmetric carbon atoms in the optically active group which is essential for the expression of a chiral smectic C phase. These compounds include, for example, liquid crystal compounds having a dichiral epoxide side chain [David M. Walba et al., Journal of American Chemical Society, 108, 7424 (1986)], and liquid crystal compounds having a halogen atom and a methyl group on two adjacent asymmetric carbon atoms [cf. e.g. JP-A-168780/1985, 218358/1985, 68449/1986, 30740/1987, 46/1987, 103043/1987, 111950/1987, 142131/1987, 175443/1987].

A typical example of the above liquid crystal compounds is 4'-octylcarbonyloxy-4-biphenyl (S)-3-methyl-2-chloropentanoate [JP-A-68449/1986]. This liquid crystal compound has a very large spontaneous polarization of 180 nC/cm², but, being an aliphatic chloro compound, has poor chemical stability. Hence, there has been synthesized 4'-octylcarbonyloxy-4-[(S)-2-methoxy-(S)-3-methylpentyloxycarbonyl]biphenyl [JP-A-228036/1987]. This compound has excellent chemical stability but has a small spontaneous polarization of 17 nC/cm². Thus, no compound has been developed yet which is chemically stable and yet has a large spontaneous polarization.

OBJECT AND SUMMARY OF THE INVENTION

The present inventors made investigation in order to find out a ferroelectric liquid crystal compound having excellent physical and chemical stabilities and a large spontaneous polarization, and have reached the present invention. That is, the present inventors made investigation on liquid crystal compounds wherein a chemically stable ester compound and an optically active group having two asymmetric carbon atoms are combined, particularly on the correlation of the chemical structure of the optically active group and the spontaneous polarization of the resulting liquid crystal compound, and have reached the present invention based on the results of the investigation.

The spontaneous polarization of a ferroelectric liquid crystal depends on the dipole moment of the ether group or carboxylic acid ester group bonding to the asymmetric carbons. When a polar group such as ether group, carboxylic acid ester group or the like is allowed to bond to each of the two asymmetric carbons, the correlation of the dipole moment vectors of the two polar groups is important. That is, it was found that fixing the steric conformation of the two polar groups, i.e. preventing the free rotation of the bond between the two asymmetric carbon atoms is very effective to obtain a large spontaneous polarization. Thus, a large spontaneous polarization has been successufliy obtained by fixing the steric conformation of the polar groups on the asymmetric carbon atoms, without using a halogen-atom bond which has poor chemical stability.

BRIEF DESCRIPTION OF DRAWING

FIG. 1 is a schematic illustration of an example of the liquid crystal display device according to the present invention. 1 and 2 are each a polarization plate; 2 is a front side glass; 3 and 6 are each a transparent electrode; 4 is a ferroelectric liquid crystal phase; 5 is a seal; 7 is a back side glass.

DETAILED DESCRIPTION OF PREFERRED EMBODIMENTS

The present invention relates to optically active compounds represented by the general formula

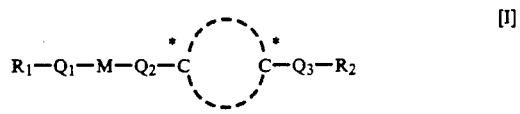

[I]

wherein $R_1$ is an alkyl group, an alkenyl group or an alkynyl group each of 3-14 carbon atoms; $R_2$ is an alkyl group of 1-10 carbon atom, an alkenyl group of 2-10 carbon atoms or an alkynyl group of 2-10 carbon atoms;

is a five- to eight-membered ring which may contain hetero-atom(s) or double bond(s); $Q_1$ is a single bond, a (thio)ether group, a carboxylic acid ester group, a carbonyl group or a carbonyldioxy group; $Q_2$ and $Q_3$ are independently a single bond, a (thio)ether group, a carboxylic acid ester group, a carbonyl group, a carbonyldioxy group or a methyleneoxy group; M is

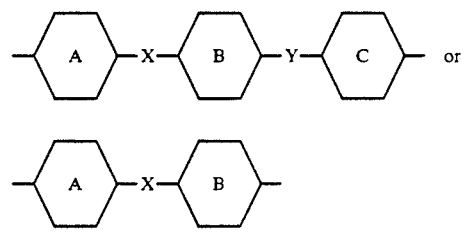

(X and Y are independently a single bond, a carboxylic acid ester group, a methyleneoxy group or an ethylene group, and

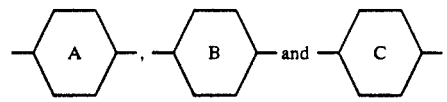

are independently a homocyclic or heterocyclic six-membered ring-1,4-diyl group which may contain 1-2 oxygen or nitrogen atoms as ring-forming atoms); the carbon atoms with the asterisk (*) denote asymmetric carbon atoms; the hydrogen atoms bonding to the asymmetric carbon atoms may be substituted with a lower alkyl group of 1-6 carbon atoms or a lower alkenyl group of 2-6 carbon atoms.

The liquid crystal compounds I of the present invention have properties essential for ferroelectric liquid crystal compounds, despite the steric conformation of the polar groups on the asymmetric carbon atoms of the ring portion, and are characterized by expressing a large spontaneous polarization when the two polar groups on the asymmetric carbon atoms are in a same direction steric conformation. For example, when steric conformation of the two polar groups on the asymmetric carbon atoms of the ring portion is formed in such a way that a 5-membered ring or the like is formed using two adjacent asymmetric carbon atoms and $Q_2$ and $Q_3$ are allowed to be in the same direction relative to the plane of the ring, i.e. in a cis form, the vectors of the dipole moments of $Q_2$ and $Q_3$ have the same direction and as a result a large spontaneous polarization can be obtained.

Therefore, the first aspect of the present invention lies in liquid crystal compounds having a large spontaneous polarization; the second aspect lies in liquid crystal compositions comprising at least one of said optically active compounds; the third aspect lies in liquid crystal optical modulators using said liquid crystal compositions.

The compounds I relating to the first aspect of the present invention can be classified into the following compounds I' and I", depending upon the basic skeleton M.

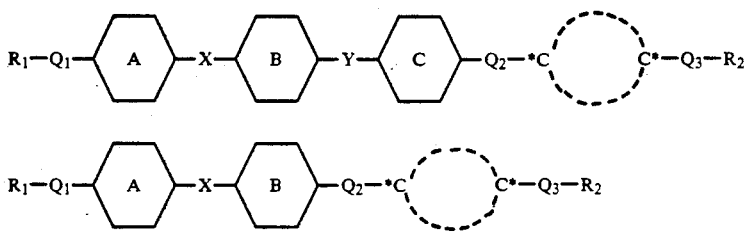

In the above compounds I, I' and I", the alkyl groups of 3-14 carbon atoms, represented by $R_1$ can be of straight chain or branched chain. Specifically, there can be mentioned straight chain alkyl groups such as propyl, butyl, pentyl, hexyl, heptyl, octyl, nonyl, decyl, undecyl, dodecyl, tridecyl, tetradecyl and the like, as well as branched chain alkyl groups such as isopropyl, isobutyl, sec-butyl, tert-butyl, isopentyl, neopentyl, tert-pentyl, isohexyl, 1-methylpentyl, 2-methylpentyl, 5-methylhexyl, 2,3,5-trimethylhexyl, 2,7,8-trimethyldecyl, 4-ethyl-5-methylnonyl and the like. Of these, preferable are straight chain alkyl groups of 6-12 carbon atoms, such as hexyl, heptyl, octyl, decyl, undecyl, dodecyl and the like.

As the alkenyl groups and alkynyl groups represented by $R_1$, there can be mentioned, for example, those alkenyl and alkynyl groups corresponding to the above alkyl groups.

The alkyl groups of 1-10 carbon atoms represented by $R_2$ can be of straight chain or branched chain. Specifically, there can be mentioned straight chain alkyl groups such as methyl, ethyl, propyl, butyl, pentyl, hexyl, heptyl, octyl, nonyl, decyl and the like, as well as branched chain alkyl groups such as isopropyl, isobutyl, sec-butyl, tert-butyl, isopentyl, neopentyl, tert-pentyl, isohexyl, 1-methylpentyl, 2-methylpentyl, 5-methylhexyl, 4-ethylhexyl, 2,3,5-trimethylhexyl, 4-ethyl-5-methylhexyl and the like. Of these, preferable are straight chain alkyl group of 1-8 carbon atoms, such as methyl, ethyl, propyl, butyl, phenyl, hexyl, heptyl and octyl.

As the alkenyl and alkynyl groups represented by $R_2$, there can be mentioned, for example, those alkenyl and alkynyl groups corresponding to the above alkyl groups.

$Q_1$, $Q_2$ and $Q_3$ each represent a single bond, a (thio)ether group, a carboxylic acid ester group, a carbonyl group, a carbonyldioxy group or a methyleneoxy group.

As the carboxylic acid ester group, there can be mentioned a

ester group and a

ester group.

As the methylenoxy group, there can be mentioned a —$CH_2O$— group and a —$OCH_2$— group.

With respect to the various bond and groups which can be taken by $Q_1$, $Q_2$ and $Q_3$, $Q_1$ is preferably a single bond, a (thio)ether group or a

ester group; $Q_2$ is preferably a

ester group, a

ester group or an ether group; and $Q_3$ is preferably a (thio)ether group, a

ester group or a

ester group.

As the carboxylic acid ester group represented by X or Y, there can be mentioned a

ester group and a

ester group. As the methylenoxy group represented by X or Y, there can be mentioned a —CH$_2$O— group and a —OCH$_2$— group.

As the six-membered ring-1,4-diyl group represented by

 ,  or  , there can be specifically mentioned, for example, p-phenylene, 1,4-cyclohexylene, 2,5-(1,3-dioxane)diyl, 2,5-pyridinediyl, 2,5-pyrimidinediyl, 2,5-(1,4-pyrazine)diyl and 3,6-(1,2-pyridazine)diyl. These rings may be substituted with halogen, cyano, methyl or methoxy.

 ,  and 

may be the same or different.

2,5-(1,3-Dioxane)diyl can be

 or  ;

2,5-pyridinediyl can be

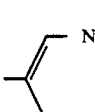 or 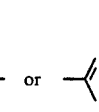 ;

2,5-pyrimidinediyl can be

 or  .

When M is

—X——Y— , preferable combinations of

 ,  , 

X and Y include the case where one of X and Y is a single bond, the other of them is a carboxylic acid ester bond, and all of

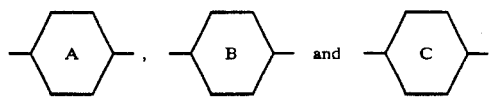

are p-phenylene or one of them is 2,5-pyrimidinediyl. When M is

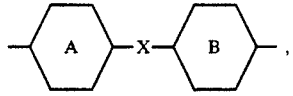 , preferable combinations of

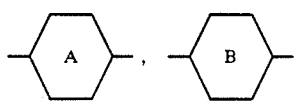

and X include the case where X is a single bond and both of

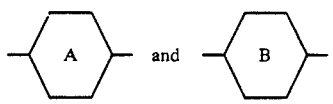

are p-phenylene or one of them is 2,5-pyrimidinediyl.

The compounds I have two asymmetric carbon atoms within the molecule and therefore have four different optical isomers, that is, (R,R) type (R,S) type, (S,R) type and (S,S) type.

The compounds I of the present invention can be produced according to, for example, the following processes.

Method 1

Compounds of the general formula I wherein Q$_2$ is a $$-\overset{\overset{O}{\|}}{C}-O-$$

ester group.

Scheme 1

R$_1$—Q$_1$—M—COOH
[II]

↓

HO—*C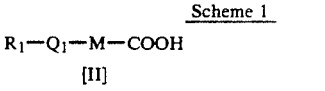C*—Q$_3$—R$_2$
[III]

↓

R$_1$—Q$_1$—M—$\overset{\overset{O}{\|}}{C}$—O—*C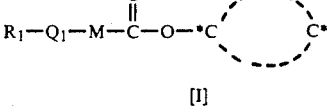C*—Q$_3$—R$_2$
[I]

($R_1$, $R_2$, $Q_1$, $Q_3$ and M have the same definitions as above. The same applies hereinafter.)

As shown in the above scheme 1, the compound I can be obtained by subjecting a carboxylic acid II and an optically active dichiral alcohol III to a condensation reaction. This condensation reaction per se is known and can be effected according to a conventional method. For example, the carboxylic acid II and the dichiral alcohol III are condensed in an organic solvent in the presence of a proton acid. As the proton acid, there can be used, for example, inorganic acids such as sulfuric acid, hydrochloric acid, perchloric acid and the like; organic sulfonic acids such as p-toluene-sulfonic acid, benzene-sulfonic acid, trifluoromethane-sulfonic acid, methane-sulfonic acid and the like; and strongly acidic ion exchange resins such as Amberlist ® and the like. As the organic solvent, there can be mentioned, for example, hydrocarbons such as hexane, benzene, toluene and the like, halogenated hydrocarbons such as chloroform, methylene chloride, carbon tetrachloride, 1,2-dichloroethane and the like, ethers such as diethyl ether, tetrahydrofuran, dioxane and the like, ethyl acetate, acetonitrile and dimethylformamide. It is possible that the carboxylic acid II be converted to an acid halide with, for example, a halogenating agent such as phosphorus pentachloride, thionyl chloride, thionyl bromide or the like and the halide be reacted with the dichiral alcohol III in the above mentioned organic solvent in the presence of, for example, a tertiary amine such as pyridine, triethylamine or the like. It is further possible that the alcohol III be converted to a trimethylsilyl ether derivative

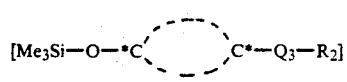

and the ether be condensed with an acid halide derivative of the carboxylic acid II in the presence of a Lewis acid such as zinc chloride or the like.

It is furthermore possible that the carboxylic acid II and the alcohol III be reacted with an activating agent such as N,N'-dicyclohexylcarbodiimide (DCC), Mukaiyama's reagent illustrated by a 1-methyl-2-halopyridium iodide, diethyl azodicarboxylate (DEAD) and triphenylphosphine ($Ph_3P$) (Mitsunobu's reagent), triphenylphosphine dibromide or the like.

These methods are described in, for example, J. Org. Chem., 27, 4675 (1962); Tetrahedron Lett., 1978, 4475; Chemistry Lett., 1975, 1045; Chemistry Lett., 1976, 13; Bull. Chem. Soc. Japan, 50, 1863 (1977); Bull, Chem. Soc. Japan. 40, 2380 (1967); Syn. Commun., 16, 1423 (1986); and Syh. Commun., 16, 659 (1986).

Method 2

Compounds of the general formula I wherein $Q_2$ is a

group.

Scheme 2

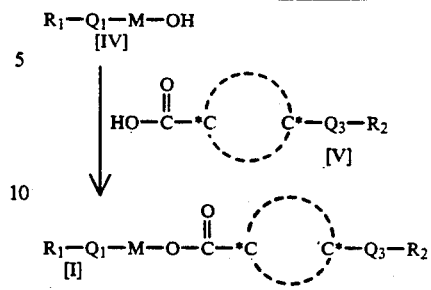

As shown in the above scheme 2, the compound I can be obtained by subjecting a hydroxyl group-containing compound IV and an optically active dichiral carboxylic acid V to a condensation reaction. This condensation reaction per se is known and can be effected according to a conventional method.

Method 3

Compounds of the general formula I wherein $Q_2$ is an ether group (—O—).

Scheme 3

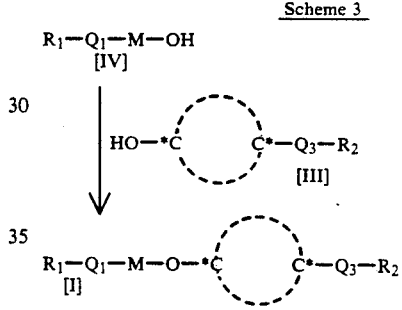

As shown in the above scheme 3, the compound I can be obtained by subjecting a hydroxyl group-containing compound IV and an optically active dichiral alcohol III to an etherification reaction. This etherification reaction per se is known and can be effected according to a conventional method. For example, the reaction can be effected with diethyl azodicarboxylate (DEAD) and triphenylphosphine ($Ph_3P$) (S. Bittner et al., Chem. & Ind., 1975, 281).

It is also possible that the dichiral alcohol III and an organic sulfonyl chloride be reacted in an organic solvent in the presence of an organic base (e.g. pyridine, triethylamine) or an inorganic base (e.g. sodium hydride) to obtain a corresponding organic sulfonic acid ester and the ester be reacted with the hydroxyl group-containing compound IV. This reaction is conducted in an organic solvent in the presence of an inorganic base (e.g. potassium carbonate, sodium hydride) or an organic base (e.g. pyridine, triethylamine). As the organic sulfonyl chloride usable in the reaction, there can be mentioned, for example, aromatic sulfonyl chlorides such as p-toluenesulfonyl chloride, o-toluenesulfonyl chloride, p-chlorobenzenesulfonyl chloride, benzenesulfonyl chloride, α-naphthalenesulfonyl chloride, β-naphthalenesulfonyl chloride and the like, as well as aliphatic sulfonyl chlorides such as methanesulfonyl chloride, trifluoromethanesulfonyl chloride and the like.

As the organic solvent usable in the etherification reaction, there can be mentioned, for example, aliphatic hydrocarbons (e.g. hexane, cyclohexane), halogenated hydrocarbons (e.g. chloroform, methylene chloride, carbon tetrachloride, 1,2-dichloroethane), ethers (e.g. diethyl ether, tetrahydrofuran, dioxane), aromatic hydrocarbons (e.g. benzene, toluene), ethyl acetate, acetonitrile, dimethylformamide (DMF), dimethyl sulfoxide (DMSO) and hexamethylphosphoric triamide (HMPA).

In the etherification reaction, the activation of the dichiral alcohol III can be effected not only by converting the dichiral alcohol III to the above mentioned organic sulfonic acid ester but also by converting the alcohol III to a halogen derivative. The conversion to a halogen derivative can be effected by, for example, reacting the organic sulfonic acid ester with a metal halide (e.g. sodium iodide, potassium iodide). Or, the dichiral alcohol III can be directly reacted with a halogenating agent such as phosphorus pentachloride, thionyl chloride, thionyl bromide or the like. The thus obtained halogen derivative can be reacted with the hydroxyl group-containing compound IV in organic solvent in the presence of the above mentioned inorganic or organic base.

$Q_2$ also represents a single bond, a carbonyl group, a carbonyldioxy group or a methyleneoxy group, and those compounds of the general formula I having, as $Q_2$ one of these bonds or groups can also be produced according to a conventional method.

The compounds I obtained by the above processes can be separated from the reaction mixture and purified by ordinary separation and purification methods such as extraction, solvent operation, column chromatography, liquid chromatography, recrystallization and the like.

All of the starting materials II, III, IV and V for production of the optically active compounds I of the present invention are known substances or can be easily derived from known substances. For example, the optically active dichiral compound III or V is a novel compound and can be derived from known optically active dichiral compounds, and can also be obtained by, for example, a chemical asymmetric synthesis [J. D. Morrison et al., Asymmetric Synthesis, vol. 1 (1983) to vol. 5 (1985); B. Bosnich et al., Asymmetric Catalysis (1986); M. A. Sutter et al., Ann., 1983, 939], a biological asymmetric synthesis using an enzyme or a microorganism [J. B. Jones et al., "Applications of Biochemical Systems in Organic Chemistry", John Wiley, New York (1976); G. Frater et al., Tetrahedron, 40, 1269 (1984); R. W. Hoffman et al., Chem. Ber., 114, 2786 (1981); K. Nakamura et al., Tetrahedron Lett., 27, 3155 (1986)], and an optical resolution [J. Jacques et al., "Enantiomers, Racemates and Resolutions", John Wiley & Sons (1981); A. W. Ingersoll, Org. Synth., Coll. vol., 2, 506 (1943); H. Nohira et al., Chemistry Lett., 1981, 875, 951]. The thus obtained dichiral compound III or V can be subjected to inversion of configuration on asymmetric carbon by a chemical or biological method to convert it into other optical isomer(s). As the typical methods for inverting the hydroxyl group of optically active secondary alcohol, there are known, for example, a method in which the hydroxyl group is converted into an organic sulfonic acid ester and then subjected to an intramolecular nucleophillic substitution reaction to effect inversion [E. J. Corey et al., Tetrahedron Lett., 1975, 3183; D. T. Sawyer and M. J. Gibian, Tetrahedron, 35, 1471 (1979); W. H. Krulzinger et al., J. Org. Chem., 46, 4321 (1981); J. W. Hoffman and R. C. Desai, Syn. Commun., 13, 553 (1978)], a method in which an optically active secondary alcohol is activated by N,N'-dicyclohexylcarbodiimide (DCC) in the presence of cuprous chloride and then reacted with an appropriate carboxylic acid to effect inversion [J. Kaulen, Angew. Chem., 99, 800 (1987)], and a method in which an optically active secondary alcohol is reacted with diethyl azodicarboxylate (DEAD), triphenylphosphine (Ph₃P) and an appropriate carboxylic acid to effect inversion [O. Mitsunobu and E. Eguchi, Bull. Chem. Soc. Japan, 44, 3427 (1971); O. Mitsunobu, Synthesis, 1981, 1].

In the optically active dichiral secondary alcohol III and optically active dichiral carboxylic acid V which are both the important materials for the dichiral portion of the optically active compounds of the present invention, the

is a five- to eight-membered alicyclic compound, a five- to eight-membered cyclic compound containing heteroatom(s) or a five- to eight-membered cyclic compound containing double bond(s).

These cyclic compounds may have, on the asymmetric carbon atoms and other ring-forming atoms, substituent(s) such as lower alkyl group of 1-6 carbon atoms, alkenyl group of 2-6 carbon atoms and the like.

When the

is an alicyclic compound, it may be any of five- to eight-membered rings, but is preferably a five- or six-membered ring. It is specifically as follows when shown by the general formula.

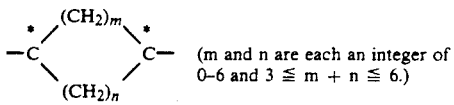 (m and n are each an integer of 0-6 and $3 \leq m + n \leq 6$.)

In the above formula, however, when m=n and the ring group has no substituent, the carbon atoms with the asterisk (*) are not asymmetric carbon atoms; therefore, such an alicyclic compound is excluded from the present invention.

When the

is an alicyclic compound, examples of the compounds represented by the general formula III and the general formula V are as follows.

Examples of the optically active dichiral secondary alcohol III wherein $Q_3$ is an ether group (—O—), are as follows.

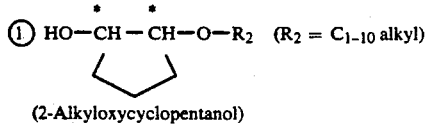

(2-Alkyloxycyclopentanol)

Specific examples of this alcohol include straight chain alkyloxy cyclopentanols such as 2-methoxycyclopentanol, 2-ethoxycyclopentanol, 2-propoxycyclopentanol, 2-butoxycyclopentanol, 2-pentyloxycyclopentanol, 2-hexyloxycyclopentanol, 2-heptyloxycyclopentanol, 2-octyloxycyclopentanol, 2-nonyloxycyclopentanol, 2-decyloxycyclopentanol and the like, as well as branched chain alkyloxycyclopentanols such as 2-isopropoxycyclopentanol, 2-isobutoxycyclopentanol, 2-tert-butoxycyclopentanol, 2-(2-methylpentyloxy)cyclopentanol, 2-(3-methylpentyloxy)cyclopentanol and the like.

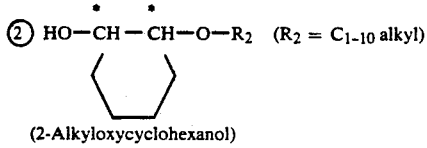

(2-Alkyloxycyclohexanol)

Specific examples of this compound include straight chain alkyloxycyclohexanols such as 2-methoxycyclohexanol, 2-ethoxycyclohexanol, 2-propoxycyclohexanol, 2-butoxycyclohexanol, 2-pentyloxycyclohexanol, 2-hexyloxycyclohexanol, 2-heptyloxycyclohexanol, 2-octyloxycyclohexanol, 2-nonyloxycyclohexanol, 2-decyloxycyclohexanol and the like, as well as branched chain alkyloxycyclohexanols such as 2-isopropoxycyclohexanol, 2-isobutoxycyclohexanol, 2-tert-butoxycyclohexanol, 2-(2-methylpentyloxy)cyclohexanol, 2-(3-methylpentyloxy)cyclohexanol and the like.

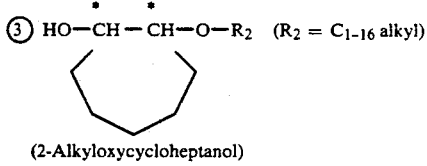

(2-Alkyloxycycloheptanol)

Specific examples of this compound include straight chain alkyloxycycloheptanols such as 2-methoxycycloheptanol, 2-ethoxycycloheptanol, 2-propoxycycloheptanol, 2-butoxycycloheptanol, 2-pentyloxycycloheptanol, 2-hexyloxycycloheptanol, 2-heptyloxycycloheptanol, 2-octyloxycycloheptanol, 2-nonyloxycycloheptanol, 2-decyloxycycloheptanol and the like, as well as branched chain alkyloxycycloheptanols such as 2-isopropoxycycloheptanol, 2-isobutoxycycloheptanol, 2-tert-butoxycycloheptanol, 2-(2-methylpentyloxy)cycloheptanol, 2-(3-methylpentyloxy)cycloheptanol and the like.

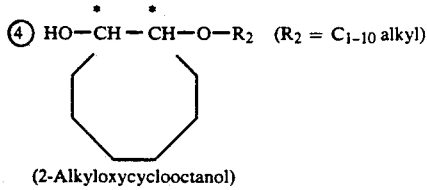

(2-Alkyloxycyclooctanol)

Specific examples of this compound include straight chain alkyloxycyclooctanols such as 2-methoxycyclooctanol, 2-ethoxycyclooctanol, 2-propoxycyclooctanol, 2-butoxycyclooctanol, 2-pentyloxycyclooctanol, 2-hexyloxycyclooctanol, 2-heptyloxycyclooctanol, 2-octyloxycyclooctanol, 2-nonyloxycyclooctanol, 2-decyloxycyclooctanol and the like, as well as branched alkyloxycyclooctanols such as 2-isopropoxycyclooctanol, 2-isobutoxycyclooctanol, 2-tert-butoxycyclooctanol, 2-(2-methylpentyloxy)cyclooctanol, 2-(3-methylpentyloxy)cyclooctanol and the like.

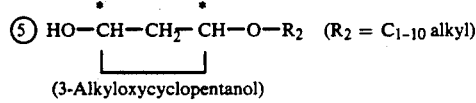

(3-Alkyloxycyclopentanol)

Specific examples of this compound include straight chain alkyloxycyclopentanols such as 3-methoxycyclopentanol, 3-ethoxycyclopentanol, 3-propoxycyclopentanol, 3-butoxycyclopentanol, 3-pentyloxycyclopentanol, 3-hexyloxycyclopentanol, 3-heptyloxycyclopentanol, 3-octyloxycyclopentanol, 3-nonyloxycyclopentanol, 3-decyloxycyclopentanol and the like, as well as alkyloxycyclopentanols such as 3-isopropoxycyclopentanol, 3-isobutoxycyclopentanol, 3-tert-butoxycyclopentanol, 3-(2-methylpentyloxy)cyclopentanol, 3-(3-methylpentyloxy)cyclopentanol and the like.

Specific examples of other homologues of the alicyclic secondary alcohol III wherein $Q_3$ is an ether group, are as follows.

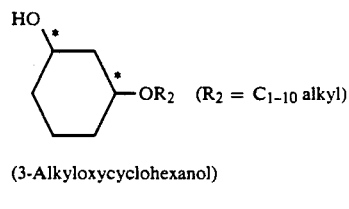

(3-Alkyloxycyclohexanol)

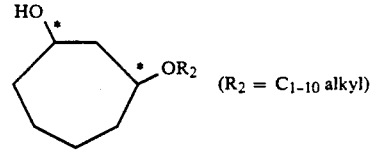

(3-Alkyloxycycloheptanol)

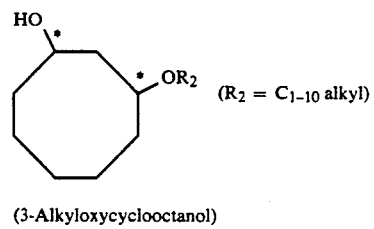

(3-Alkyloxycyclooctanol)

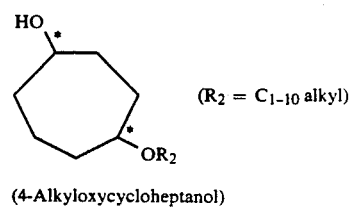

(4-Alkyloxycycloheptanol)

(4-Alkyloxycyclooctanol) — cyclooctane ring with HO at one position and OR$_2$ at another (R$_2$ = C$_{1-10}$ alkyl)

Specific examples of the optically active dichiral secondary alcohol III wherein Q$_3$ is a $$-O-\overset{O}{\underset{\|}{C}}-$$

ester group, are as follows.

(2-Acyloxycyclopentanol) — cyclopentane with HO and O-C(=O)-R$_2$ (R$_2$ = C$_{1-10}$ alkyl)

(2-Acyloxycyclohexanol) — cyclohexane with HO and O-C(=O)-R$_2$ (R$_2$ = C$_{1-10}$ alkyl)

(2-Acyloxycycloheptanol) — cycloheptane with HO and O-C(=O)-R$_2$ (R$_2$ = C$_{1-10}$ alkyl)

(2-Acyloxycyclooctanol) — cyclooctane with HO and O-C(=O)-R$_2$ (R$_2$ = C$_{1-10}$ alkyl)

Specific examples of the optically active dichiral secondary alcohol III wherein Q$_3$ is a $$-\overset{O}{\underset{\|}{C}}-O-$$

ester group, are as follows.

(Alkyl ester of 2-hydroxycyclopentanecarboxylic acid) — cyclopentane with HO and C(=O)-O-R$_2$ (R$_2$ = C$_{1-10}$ alkyl)

(Alkyl ester of 2-hydroxycyclohexanecarboxylic acid) — cyclohexane with HO and C(=O)-O-R$_2$ (R$_2$ = C$_{1-10}$ alkyl)

(Alkyl ester of 2-hydroxycycloheptanecarboxylic acid) — cycloheptane with HO and C(=O)-O-R$_2$ (R$_2$ = C$_{1-10}$ alkyl)

(Alkyl ester of 2-hydroxycyclooctanecarboxylic acid) — cyclooctane with HO and C(=O)-O-R$_2$ (R$_2$ = C$_{1-10}$ alkyl)

Examples of the optically active cyclic dichiral carboxylic acid V are as follows.

Examples of the optically active cyclic dichiral carboxylic acid V wherein Q$_3$ is an ether group (—O—), are follows (1) (2-Alkyloxycyclopentanecarboxylic acid) — cyclopentane with HOC(=O)- and -OR$_2$ (R$_2$ = C$_{1-10}$ alkyl)

Specific examples of this compound include straight chain alkyloxycyclopentanecarboxylic acids such as 2-methoxycyclopentanecarboxylic acid, 2-ethoxycyclopentanecarboxylic acid, 2-propoxycyclopentanecarboxylic acid, 2-butoxycyclopentanecarboxylic acid, 2-pentyloxycyclopentanecarboxylic acid, 2-hexyloxycyclopentanecarboxylic acid, 2-heptyloxycyclopentanecarboxylic acid, 2-octyloxycyclopentanecarboxylic acid, 2-nonyloxycyclopentanecarboxylic acid, 2-decyloxycyclopentanecarboxylic acid and the like, as well as branched chain alkyloxycyclopentanecarboxylic acids such as 2-isopropoxycyclopentanecarboxylic acid, 2-isobutoxycyclopentanecarboxylic acid, 2-tert-butoxycyclopentanecarboxylic acid, 2-(2-methylpentyloxy)- cyclopentanecarboxylic acid, 2-(3-methylpentyloxy)cyclopentanecarboxylic acid and the like.

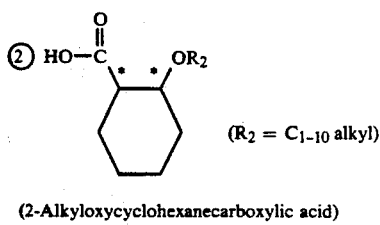

(2-Alkyloxycyclohexanecarboxylic acid)

Specific examples of this compound include straight chain alkyloxycyclohexanecarboxylic acids such as 2-methoxycyclohexanecarboxylic acid, 2-ethoxycyclohexanecarboxylic acid, 2-propoxycyclohexanecarboxylic acid, 2-butoxycyclohexanecarboxylic acid, 2-pentyloxycyclohexanecarboxylic acid, 2-hexyloxycyclohexanecarboxylic acid, 2-heptyloxycyclohexanecarboxylic acid, 2-octyloxycyclohexanecarboxylic acid, 2-nonyloxycyclohexanecarboxylic acid, 2-decyloxycyclohexanecarboxylic acid and the like, as well as branched chain alkyloxycyclohexanecarboxylic acids such as 2-isopropoxycyclohexanecarboxylic acid, 2-isobutoxycyclohexanecarboxylic acid, 2-tert-butoxycyclohexanecarboxylic acid, 2-(2-methylpentyloxy)cyclohexanecarboxylic acid, 2-(3-methylpentyloxy)cyclohexanecarboxylic acid and the like.

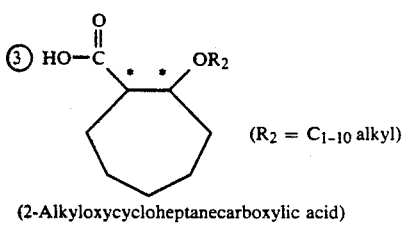

(2-Alkyloxycycloheptanecarboxylic acid)

Specific examples of this compound include straight chain alkyloxycycloheptanecarboxylic acid such as 2-methoxycycloheptanecarboxylic acid, 2-ethoxycycloheptanecarboxylic acid, 2-propoxycycloheptanecarboxylic acid, 2-butoxycycloheptanecarboxylic acid, 2-pentyloxycycloheptanecarboxylic acid, 2-hexyloxycycloheptanecarboxylic acid, 2-heptyloxycycloheptanecarboxylic acid, 2-octyloxycycloheptanecarboxylic acid, 2-nonyloxycycloheptanecarboxylic acid, 2-decyloxycycloheptanecarboxylic acid and the like, as well as branched chain alkyloxycycloheptanecarboxylic acids such as 2-isopropoxycycloheptanecarboxylic acid, 2-isobutoxycycloheptanecarboxylic acid, 2-tert-butoxycycloheptanecarboxylic acid, 2-(2-methylpentyloxy)cycloheptanecarboxylic acid, 2-(3-methylpentyloxy)cycloheptanecarboxylic acid and the like.

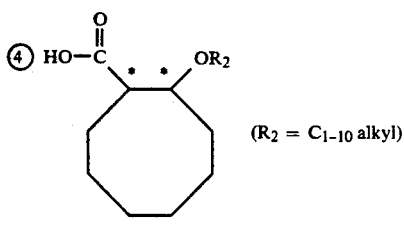

(2-Alkyloxycyclooctanecarboxylic acid)

Specific examples of this compound include straight chain alkyloxycyclooctanecarboxylic acids such as 2-methoxycyclooctanecarboxylic acid, 2-ethoxycyclooctanecarboxylic acid, 2-propoxycyclooctanecarboxylic acid, 2-butoxycyclooctanecarboxylic acid, 2-pentyloxycyclooctanecarboxylic acid, 2-hexyloxycyclooctanecarboxylic acid, 2-heptyloxycyclooctanecarboxylic acid, 2-octyloxycyclooctanecarboxylic acid, 2-nonyloxycyclooctanecarboxylic acid, 2-decyloxycyclooctanecarboxylic acid and the like, as well as branched chain alkyloxycyclooctanecarboxylic acids such as 2-isopropoxycyclooctanecarboxylic acid, 2-isobutoxycyclooctanecarboxylic acid, 2-tert-butoxycyclooctanecarboxylic acid, 2-(2-methylpentyloxy)cyclooctanecarboxylic acid, 2-(3-methylpentyloxy)cyclooctanecarboxylic acid and the like.

Examples of the optically active cyclic dichiral carboxylic acid V wherein $Q_3$ is a

ester group, are as follows.

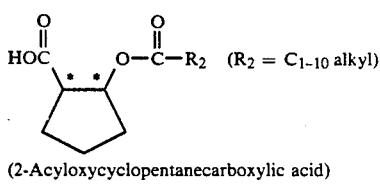

(2-Acyloxycyclopentanecarboxylic acid)

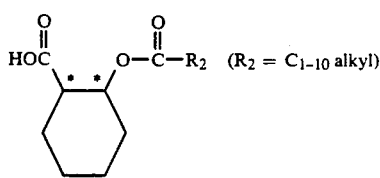

(2-Acyloxycyclohexanecarboxylic acid)

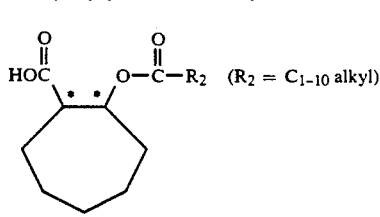

(2-Acyloxycycloheptanecarboxylic acid)

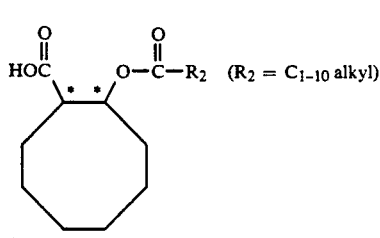

(2-Acyloxycyclooctanecarboxylic acid)

Specific examples of the optically active cyclic dichiral carboxylic acid V wherein $Q_3$ is a

ester group, are as follows.

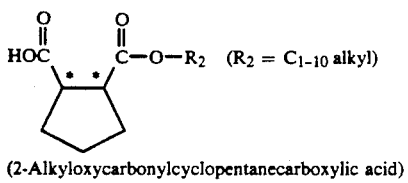

(2-Alkyloxycarbonylcyclopentanecarboxylic acid)

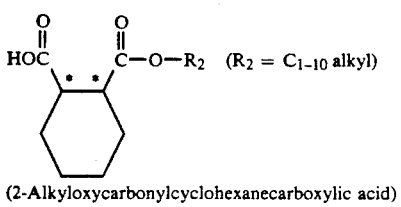

(2-Alkyloxycarbonylcyclohexanecarboxylic acid)

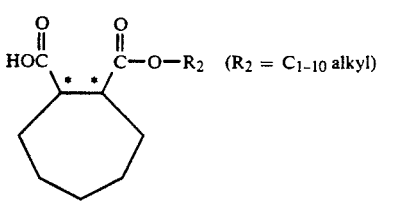

(2-Alkyloxycarbonylcycloheptanecarboxylic acid)

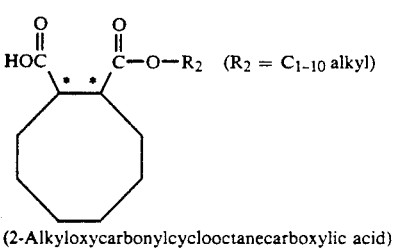

(2-Alkyloxycarbonylcyclooctanecarboxylic acid)

The optically active cyclic dichiral carboxylic acid V wherein $Q_3$ is an ether group (—O—), also includes the followings.

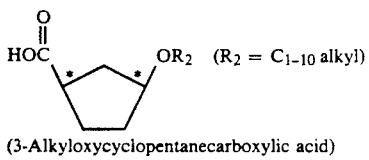

(3-Alkyloxycyclopentanecarboxylic acid)

Specific examples of this compound include straight chain alkyloxycyclopentanecarboxylic acids such as 3-methoxycyclopentanecarboxylic acid, 3-ethoxycyclopentanecarboxylic acid, 3-propoxycyclopentanecarboxylic acid, 3-butoxycyclopentanecarboxylic acid, 3-pentyloxycyclopentanecarboxylic acid, 3-hexyloxycyclopentanecarboxylic acid, 3-heptyloxycycloheptanecarboxylic acid, 3-octyloxycyclopentanecarboxylic acid, 3-nonyloxycyclopentanecarboxylic acid, 3-decyloxycyclopentanecarboxylic acid and the like, as well as branched chain alkyloxycyclopentanecarboxylic acids such as 3-isopropoxycyclopentanecarboxylic acid, 3-isobutoxycyclopentanecarboxylic acid, 3-tert-butoxycyclopentanecarboxylic acid, 3-(2-methylpentyloxy)cyclopentanecarboxylic acid, 3-(3-methylpentyloxy)cyclopentanecarboxylic acid and the like.

Specific examples of other homologues of the 3-alkyloxycyclopentanecarboxylic acid are as follows.

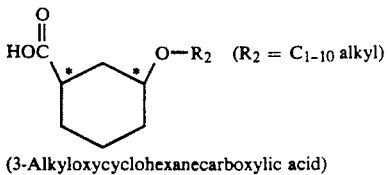

(3-Alkyloxycyclohexanecarboxylic acid)

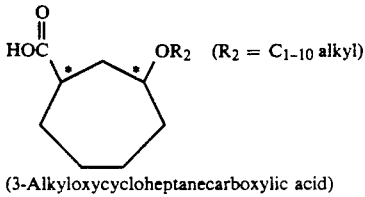

(3-Alkyloxycycloheptanecarboxylic acid)

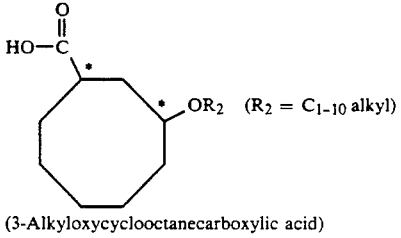

(3-Alkyloxycyclooctanecarboxylic acid)

The optically active cyclic dichiral carboxylic acid V wherein $Q_3$ is a

ester bond, also includes the following compounds.

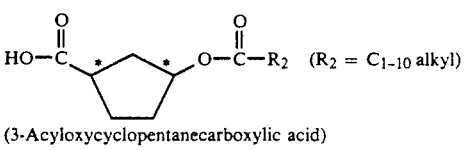

(3-Acyloxycyclopentanecarboxylic acid)

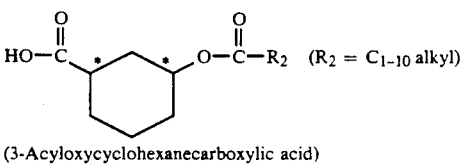

(3-Acyloxycyclohexanecarboxylic acid)

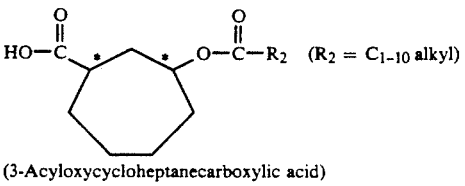

(3-Acyloxycycloheptanecarboxylic acid)

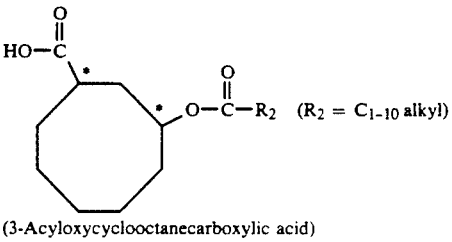

(3-Acyloxycyclooctanecarboxylic acid)

The optically active cyclic dichiral carboxylic acid V wherein $Q_3$ is a

ester group, also includes the following compounds.

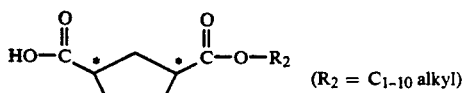

(3-Alkyloxycarbonylcyclopentanecarboxylic acid)

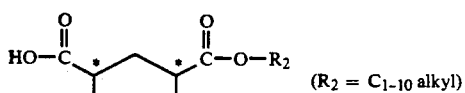

(3-Alkyloxycarbonylcyclohexanecarboxylic acid)

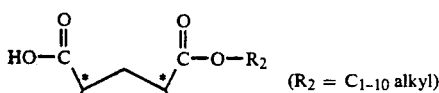

(3-Alkyloxycarbonylcycloheptanecarboxylic acid)

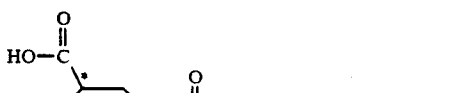

(3-Alkyloxycarbonylcyclooctanecarboxylic acid)

The optically active cyclic dichiral carboxylic acid V wherein $Q_3$ is an ether group (—O—), further includes the following compounds.

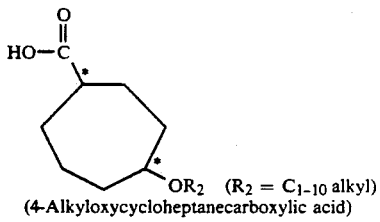

(4-Alkyloxycycloheptanecarboxylic acid)

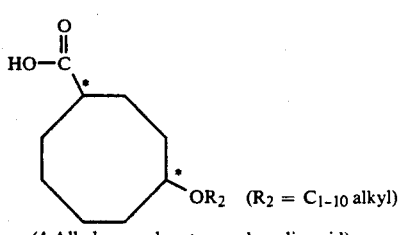

(4-Alkyloxycyclooctanecarboxylic acid)

The optically active cyclic dichiral carboxylic acid V wherein $Q_3$ is a

ester group, further includes the following compounds.

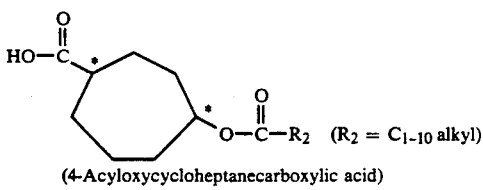

(4-Acyloxycycloheptanecarboxylic acid)

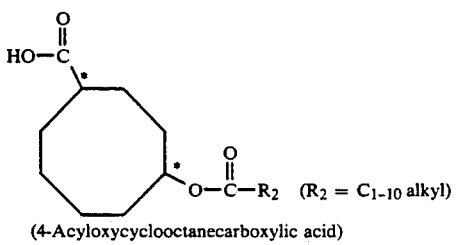

(4-Acyloxycyclooctanecarboxylic acid)

The optically active cyclic dichiral carboxylic acid V wherein $Q_3$ is a

ester group, further includes the following compounds.

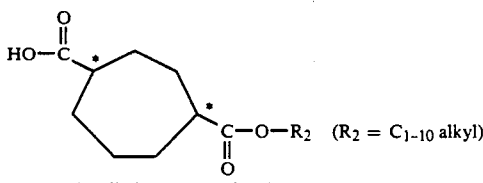

(4-Alkyloxycarbonylcycloheptanecarboxylic acid)

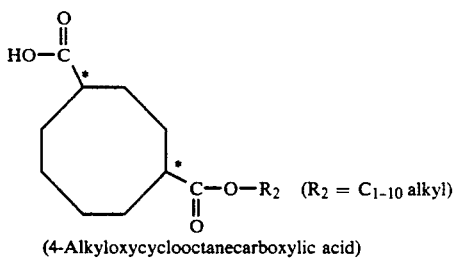

(4-Alkyloxycyclooctanecarboxylic acid)

When

is five to eight-membered heterocyclic compound, there can be mentioned a sulfur or oxygen atom as the hetero-atom in the heterocyclic ring.

When

is heterocyclic compound containing a hetero-atom, examples of the compounds represented by the general formula IV and V are as follows.

When

is five-membered ring containing a hetero-atom, for example, a sulfur atom and $Q_3$ is an ether group (—O—), there can be mentioned the following example.

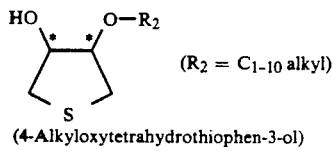

(4-Alkyloxytetrahydrothiophen-3-ol)

Specific examples of this compound include straight chain 4-alkyloxytetrahydrothiophen-3-ols such as 4-methoxytetrahydrothiophen-3-ol, 4-ethoxytetrahydrothiophen-3-ol, 4-propoxytetrahydrothiophen-3-ol, 4-butoxytetrahydrothiophen-3-ol, 4-pentyloxytetrahydrothiophen-3-ol, 4-hexyloxytetrahydrothiophen-3-ol, 4-heptyloxytetrahydrothiophen-3-ol, 4-octyloxytetrahydrothiophen-3-ol, 4-nonyloxytetrahydrothiophen-3-ol, 4-decyloxytetrahydrothiophen-3-ol and the like, as well as branched chain 4-alkyloxytetrahydrothiophen-3-ols such as 4-isopropoxytetrahydrothiophen-3-ol, 4-isobutoxytetrahydrothiophen-3-ol, 4-tert-butoxytetrahydrothiophen-3-ol, 4-(2-methylpentyloxy)tetrahydrothiophen-3-ol, 4-(3-methylpentyloxy)tetrahydrothiophen-3-ol and the like.

When

is a five-membered ring containing a sulfur atom and $Q_3$ is a

ester group, there can be mentioned the following example.

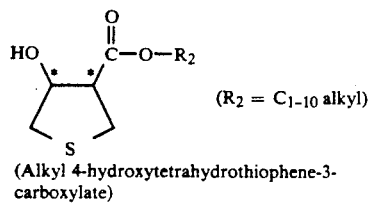

(Alkyl 4-hydroxytetrahydrothiophene-3-carboxylate)

Specific examples of this compound include straight chain alkyl ester derivatives such as methyl 4-hydroxytetrahydrothiophene-3-carboxylate, ethyl 4-hydroxytetrahydrothiophene-3-carboxylate, propyl 4-hydroxytetrahydrothiophene-3-carboxylate, butyl 4-hydroxytetrahydrothiophene-3-carboxylate, pentyl 4-hydroxytetrahydroxythiophene-3-carboxylate, hexyl 4-hydroxytetrahydrothiophene-3-carboxylate, heptyl 4-hydroxytetrahydrothiophene-3-carboxylate, octyl 4-hydroxytetrahydrothiophene-3-carboxylate, nonyl 4-hydroxytetrahydrothiophene-3-carboxylate, decyl 4-hydroxytetrahydrothiophene-3-carboxylate and the like, as well as branched chain alkyl ester derivatives such as isopropyl 4-hydroxytetrahydrothiophene-3-carboxylate, isobutyl 4-hydroxytetrahydrothiophene-3-carboxylate, tert-butyl 4-hydroxytetrahydrothiophene-3-carboxylate, 2-methylpentyl 4-hydroxytetrahydrothiophene-3-carboxylate, 3-methylpentyl 4-hydroxytetrahydrothiophene-3-carboxylate, and the like.

When

is five-mentioned ring containing a sulfur atom and $Q_3$ is a

ester group, there can also be mentioned the following example.

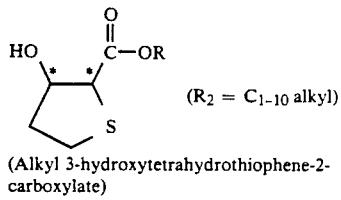

(Alkyl 3-hydroxytetrahydrothiophene-2-carboxylate)

Specific examples of this compound include straight chain alkyl ester derivatives such as methyl 3-hydroxytetrahydrothiophene-2-carboxylate, ethyl 3-hydroxytetrahydrothiophene-2-carboxylate, propyl 3-hydroxytetrahydrothiophene-2-carboxylate, butyl 3-hydroxytetrahydrothiophene-2-carboxylate, pentyl 3-hydroxytetrahydrothiophene-2-carboxylate, hexyl 3-hydroxytetrahydrothiophene-2-carboxylate, heptyl 3-hydroxytetrahydrothiophene-2-carboxylate, octyl 3-hydroxytetrahydrothiophene-2-carboxylate, nonyl 3-hydroxytetrahydrothiophene-2-carboxylate, decyl 3-hydroxytetrahydrothiophene-2-carboxylate and the like, as well as branched chain alkyl ester derivatives such as isopropyl 3-hydroxytetrahydrothiophene-2-carboxylate, isobutyl 3-hydroxytetrahydrothiophene-2-carboxylate, tert-butyl 3-hydroxytetrahydrothiophene-2-carboxylate, 2-methylpentyl 3-hydroxytetrahydrothiophene-2-carboxylate, 3-methylpentyl 3-hydroxytetrahydrothiophene-2-carboxylate and the like.

When

is a five-membered righ containing a sulfur atom and $Q_3$ is a

ester group, there can be mentioned the following example.

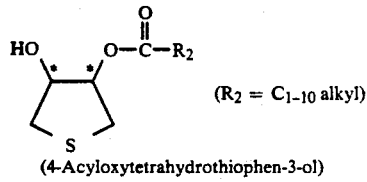

($R_2 = C_{1-10}$ alkyl)

(4-Acyloxytetrahydrothiophen-3-ol)

Specific examples of this compound include straight chain acyloxy derivatives such as 4-acetyloxytetrahydrothiophen-3-ol, 4-propionyloxytetrahydrothiophen-3-ol, 4-butyryloxytetrahydrothiophen-3-ol, 4-valeryloxytetrahydrothiophen-3-ol, 4-hexanoyloxytetrahydrothiophen-3-ol, 4-heptanoyloxytetrahydrothiophen-3-ol, 4-octanoyloxytetrahydrothiophen-3-ol, 4-nonanoyloxytetrahydrothiophen-3-ol, 4-decanoyloxytetrahydrothiophen-3-ol and the like, as well as branched chain acyloxy derivatives such as 4-isobutyryloxytetrahydrothiophen-3-ol, 4-isovaleryloxytetrahydrothiophen-3-ol, 4-pivaloyloxytetrahydrothiophen-3-ol, 4-(2-methylpentanoyloxy)tetrahydrothiophen-3-ol, 4-(3-methylpentanoyloxy)tetrahydrothiophen-3-ol and the like.

In the above, there were described specific examples of the optically active cyclic secondary alcohol III wherein

is a five-membered ring containing a sulfur atom and $Q_3$ is an ether group, a

ester group or a

ester group. However, the alcohol III is not restricted to these examples. For example when

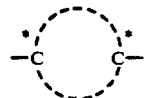

is a five-mentioned ring containing sulfur atom of high oxidation degree, i.e. a sulfoxide or a sulfone, there can be mentioned the following examples.

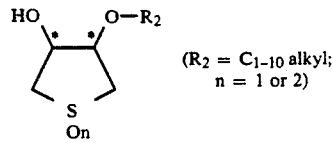

($R_2 = C_{1-10}$ alkyl; n = 1 or 2)

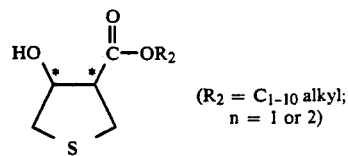

($R_2 = C_{1-10}$ alkyl; n = 1 or 2)

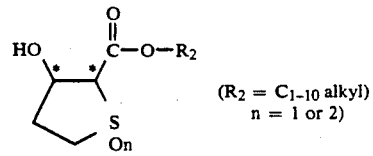

($R_2 = C_{1-10}$ alkyl) n = 1 or 2)

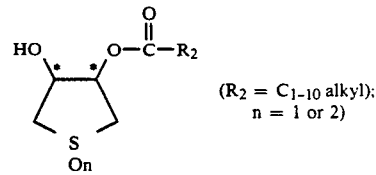

($R_2 = C_{1-10}$ alkyl); n = 1 or 2)

Also when

is a six-membered ring containing a sulfur atom, there can be membered similar derivatives.

Also when

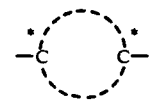

is a five or six-mentioned ring containing a hetero-atom other than sulfur atom, for example, an oxygen atom, there can be mentioned similar derivatives.

When

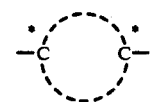

is a five- to eight-membered ring compound containing double bond(s), there are preferably selected five- or six-membered ring compounds. At that time, the number of double bonds is not restricted but is preferably 1 or 2.

Particularly preferable examples are shown below. When

is a five-membered ring containing a double bond, there can be mentioned the following examples.

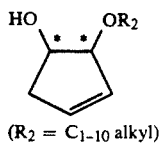

($R_2$ = $C_{1-10}$ alkyl)

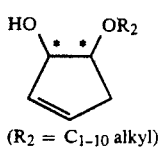

($R_2$ = $C_{1-10}$ alkyl)

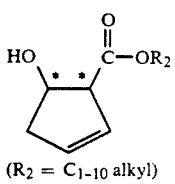

($R_2$ = $C_{1-10}$ alkyl)

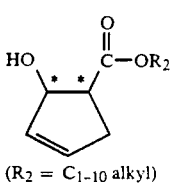

($R_2$ = $C_{1-10}$ alkyl)

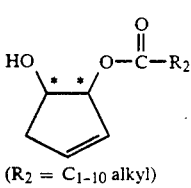

($R_2$ = $C_{1-10}$ alkyl)

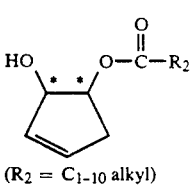

($R_2$ = $C_{1-10}$ alkyl)

When

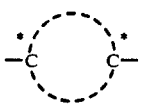

is a six-membered ring containing double bond(s), there can be mentioned the following examples.

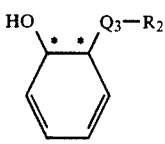

($Q_3$ and $R_2$ have the same definition as above.)

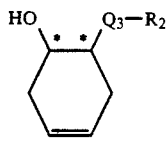

($Q_3$ and $R_2$ have the same definition as above.)

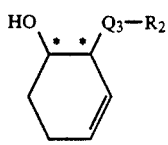

($Q_3$ and $R_2$ have the same definition as above.)

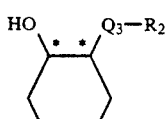

($Q_3$ and $R_2$ have the same definition as above.)

Examples of the optically active cyclic secondary alcohol III were shown above, but the alcohol III is not restricted to these examples.

As specific examples of the optically active cyclic carboxylic acid V wherein the

ring contains a hetero-atom or double bond(s), there can be mentioned the following compounds. However, the carboxylic acid V is not restricted to these examples.

When

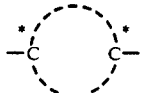

is a five-membered ring containing a hetero-atom, for example, a sulfur atom and $Q_3$ is an ether group (—O—), there can be mentioned the following compounds.

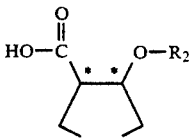

($R_2$ = $C_{1-10}$ alkyl)

(4-Alkyloxytetrahydrothiophene-3-carboxylic acid)

Specific examples of this compound include straight chain alkyloxy derivatives such as 4-methoxytetrahydrothiophene-3-carboxylic acid, 4-ethoxytetrahydrothiophene-3-carboxylic acid, 4-propoxytetrahydrothiophene-3-carboxylic acid, 4-butoxytetrahydrothiophene-3-carboxylic acid, 4-pentyloxytetrahydrothiophene-3-carboxylic acid, 4-hexyloxytetrahydrophene-3-carboxylic acid, 4-heptyloxytetrahydrothiophene-3-carboxylic acid, 4-octyloxytetrahydrothiophene-3-carboxylic acid, 4-nonyloxytetrahydrothiophene-3-carboxylic acid, 4-decyloxytetrahydrothiophene-3-carboxylic acid and the like, as well as branched chain alkyloxy derivatives such as 4-isopropoxytetrahydrothiophene-3-carboxylic acid, 4-isobutoxytetrahydrothiophene-3-carboxylic acid, 4-tert-butoxytetrahydrothiophene-3-carboxylic acid, 4-(2-methylpentyloxy)tetrahydrothiophene-3-carboxylic acid, 4-(3-methylpentyloxy)tetrahydrothiophene-3-carboxylic acid and the like.

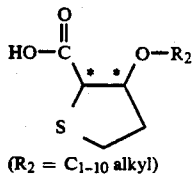

(R$_2$ = C$_{1-10}$ alkyl)

(3-Alkyloxytetrahydrothiophene-2-carboxylic acid)

Specific examples of this compound include straight chain alkyloxy derivatives such as 3-methoxytetrahydrothiophene-2-carboxylic acid, 3-ethoxytetrahydrothiophene-2-carboxylic acid, 3-propoxytetrahydrothiophene-2-carboxylic acid, 3-butoxytetrahydrothiophene-2-carboxylic acid, 3-pentyloxytetrahydrothiophene-2-carboxylic acid, 3-hexyloxytetrahydrothiophene-2-carboxylic acid, 3-heptyloxytetrahydrothiophene-2-carboxylic acid, 3-octyloxytetrahydrothiophene-2-carboxylic acid, 3-nonyltetrahydrothiophene-2-carboxylic acid, 3-decyloxytetrahydrothiophene-2-carboxylic acid and the like, as well as branched chain alkyloxy derivatives such as 3-isopropoxytetrahydrothiophene-2-carboxylic acid, 3-isobutoxytetrahydrothiophene-2-carboxylic acid, 3-tert-butoxytetrahydrothiophene-2-carboxylic acid, 2-(2-methylpentyloxy)tetrahydrothiophene-2-carboxylic acid, 3-(3-methylpentyloxy)tetrahydrothiophene-2-carboxylic acid and the like.

When

is a five-membered ring containing a sulfur atom and Q$_3$ is a

ester group, there can be mentioned the following compound.

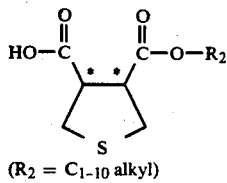

(R$_2$ = C$_{1-10}$ alkyl)

(4-Alkyloxycarbonyltetrahydrothiophene-3-carboxylic acid)

Specific examples of this compound include straight chain alkyloxycarbonyl derivatives such as 4-methoxycarbonyltetrahydrothiophene-3-carboxylic acid, 4-ethoxycarbonyltetrahydrothiophene-3-carboxylic acid, 4-propoxycarbonyltetrahydrothiophene-3-carboxylic acid, 4-butoxycarbonyltetrahydrothiophene-3-carboxylic acid, 4-pentyloxycarbonyltetrahydrothiophene-3-carboxylic acid, 4-hexyloxycarbonyltetrahydrothiophene-3-carboxylic acid, 4-heptyloxycarbonyltetrahydrothiophene-3-carboxylic acid, 4-octyloxycarbonyltetrahydrothiophene-3-carboxylic acid, 4-nonyloxycarbonyltetrahydrothiophene-3-carboxylic acid, 4-decyloxycarbonyltetrahydrothiophene-3-carboxylic acid and the like, as well as branched chain alkyloxycarbonyl derivatives such as 4-isopropoxycarbonyltetrahydrothiophene-3-carboxylic acid, 4-isobutoxycarbonyltetrahydrothiophene-3-carboxylic acid, 4-tert-butoxycarbonyltetrahydrothiophene-3-carboxylic acid, 4-(2-methylpentyloxy)carbonyltetrahydrothiophene-3-carboxylic acid, 4-(3-methylpentyloxy)carbonyltetrahydrothiophene-3-carboxylic acid and the like.

When

is a five-membered ring containing a sulfur atom and Q$_3$ is a

ester group, there can also be mentioned the following compounds.

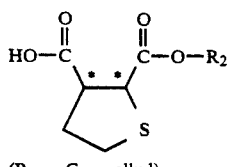

(R$_2$ = C$_{1-10}$ alkyl)

(2-Alkyloxycarbonyltetrahydrothiophenene-3-carboxylic acid)

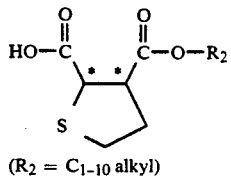

(R$_2$ = C$_{1-10}$ alkyl)

(3-Alkyloxycarbonyltetrahydrothiophene-3-carboxylic acid)

When

is a five-membered ring containing a sulfur atom and Q$_3$ is a

ester group, there can be mentioned the following compound.

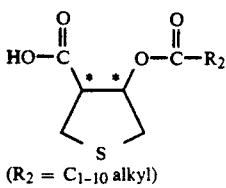

($R_2$ = $C_{1-10}$ alkyl)

(4-Acyloxytetrahydrothiophene-3-carboxylic acid)

Specific examples of this compound include straight chain acyloxy derivatives such as 4-acetyloxytetrahydrothiophene-3-carboxylic acid, 4-propionyloxytetrahydrothiophene-3-carboxylic acid, 4-butyryloxy-tetrahydrothiophene-3-carboxylic acid, 4-valeryloxytetrahydrothiophene-3-carboxylic acid, 4-heptanoyloxytetrahydrothiophene-3-carboxylic acid, 4-octanoyloxytetrahydrothiophene-3-carboxylic acid, 4-nonanoyloxytetrathiophene-3-carboxylic acid, 4-decanoyloxytetrahydrothiophene-3-carboxylic acid and the like, as well as branched chain acyloxy derivatives such as 4-isobutyryloxytetrahydrothiophene-3-carboxylic acid, 4-isovaleryloxytetrahydrothiophene-3-carboxylic acid, 4-pivaloyloxytetrahydrothiophene-3-carboxylic acid, 4-(2-methylpentanoyloxy)tetrahydrothiophene-3-carboxylic acid, 4-(3-methylpentanoyloxy)tetrahydrothiophene-3-carboxylic acid and the like.

When

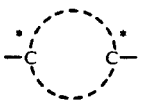

is a five-membered ring containing a sulfur atom and $Q_3$ is a

ester group, there can also be mentioned the following compound.

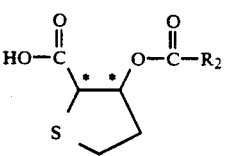

($R_2$ = $C_{1-10}$ alkyl)

(3-Acyloxytetrahydrothiophene-2-carboxylic acid)

Specific examples of this compound include straight chain acyloxy derivatives such as 3-acetyloxytetrahydrothiophene-2-carboxylic acid, 3-propionyloxytetrahydrothiophene-2-carboxylic acid, 3-butyryloxytetrahydrothiophene-2-carboxylic acid, 3-valeryloxytetrahydrothiophene-2-carboxylic acid, 3-heptanoyloxytetrahydrothiophene-2-carboxylic acid, 3-octanoyloxytetrahydrothiophene-2-carboxylic acid, 3-nonanoyloxytetrahydrothiophene-2-carboxylic acid, 3-decanoyloxytetrahydrothiophene-2-carboxylic acid and the like, as well as branched carbon acyloxy derivatives such as 3-isobutyryloxytetrahydrothiophene-2-carboxylic acid, 3-isovaleryloxytetrahydrothiophene-2-carboxylic acid, 3-pivaloyloxytetrahydrothiophene-2-carboxylic acid, 3-(2-methylpentanoyloxy)tetrahydrothiophene-2-carboxylic acid, 3-(3-methylpentanoyloxy)tetrahydrothiophene-2-carboxylic acid and the like.

Specific examples of the optical active cyclic carboxylic acid V were shown above, but the carboxylic acid V is not restricted to these examples. For example, when

is a five-membered ring containing a sulfur atom of high oxidation degree, i.e. a sulfoxide or a sulfone, there can be mentioned the following examples.

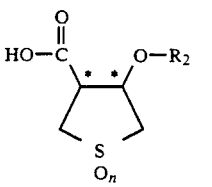

($R_2$ = $C_{1-10}$ alkyl; n = 1 or 2)

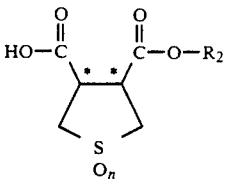

($R_2$ = $C_{1-10}$ alkyl; n = 1 or 2)

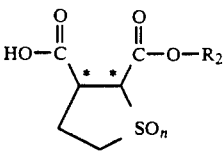

($R_2$ = $C_{1-10}$ alkyl; n = 1 or 2)

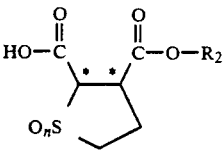

($R_2$ = $C_{1-10}$ alkyl; n = 1 or 2)

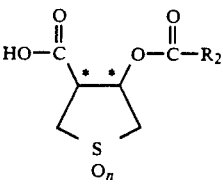

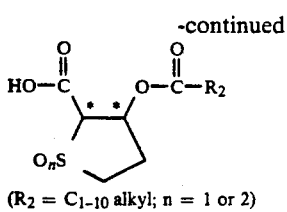

($R_2 = C_{1-10}$ alkyl; n = 1 or 2)

Also when

is a six-membered ring containing a sulfur atom, there can be mentioned similar derivatives.

Also when

is a five- or six-membered ring containing a hetero-atom other than a sulfur atom, for example, an oxygen atom, there can be mentioned similar derivatives.

When

is a five-membered ring containing double bond(s), there can be mentioned the following compounds.

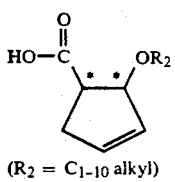

($R_2 = C_{1-10}$ alkyl)

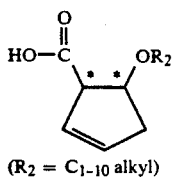

($R_2 = C_{1-10}$ alkyl)

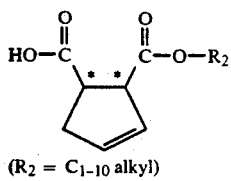

($R_2 = C_{1-10}$ alkyl)

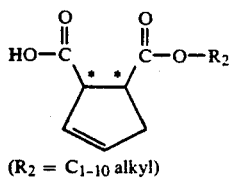

($R_2 = C_{1-10}$ alkyl)

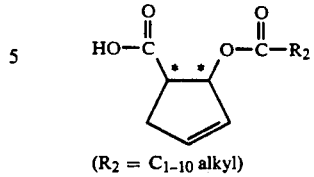

($R_2 = C_{1-10}$ alkyl)

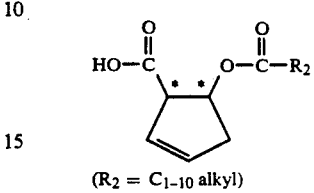

($R_2 = C_{1-10}$ alkyl)

When

is a six-membered ring containing double bond(s), there can be mentioned the following compounds.

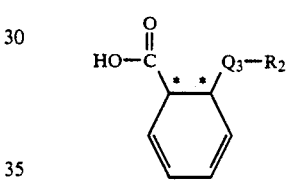

($Q_3$ and $R_2$ have the same definitions as above.)

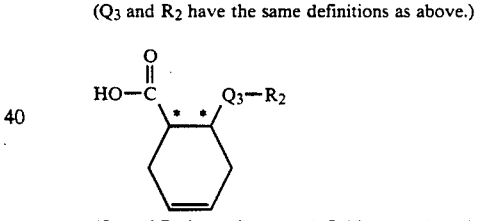

($Q_3$ and $R_2$ have the same definitions as above.)

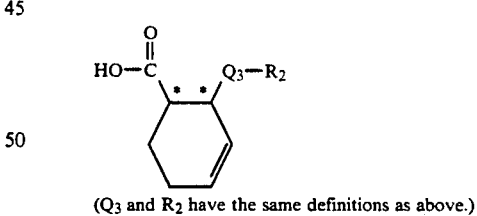

($Q_3$ and $R_2$ have the same definitions as above.)

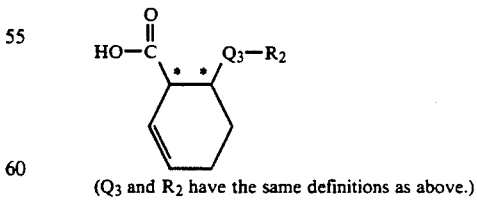

($Q_3$ and $R_2$ have the same definitions as above.)

Examples of the optically active cyclic carboxylic acid V were shown above, but the carboxylic acid V is not restricted to these examples.

The above-mentioned optically active cyclic compounds include novel compounds represented by the following formula;

[In the above formula, $R_2$ represents an alkyl group of 1 to 10 carbon atoms, an alkenyl group of 2 to 10 carbon atoms or an alkynyl group of 2 to 10 carbon atoms, $Q_3$ represents a single bond, a (thio)ether group, a carbonyl group or a methylenoxy group, and Z represents a hydroxyl group or —COOZ′ wherein Z′ represents a hydrogen or an alkyl group of 2 to 10 carbon atoms, and

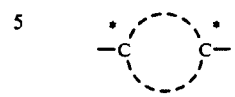

represents a five- to eight-membered ring which may contain hetero-atom(s) or double bond(s).]

These compounds are prepared by the following known method;

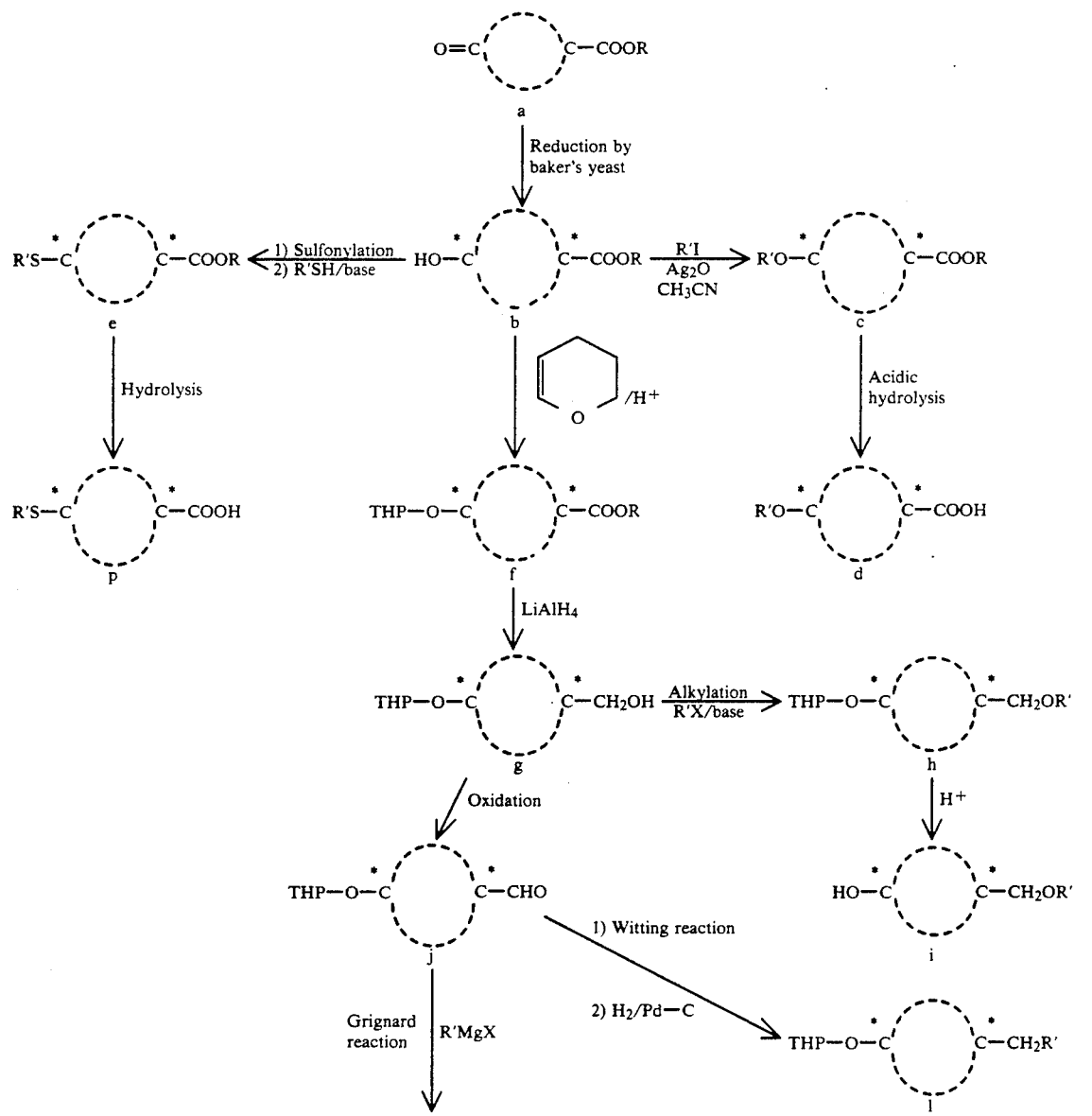

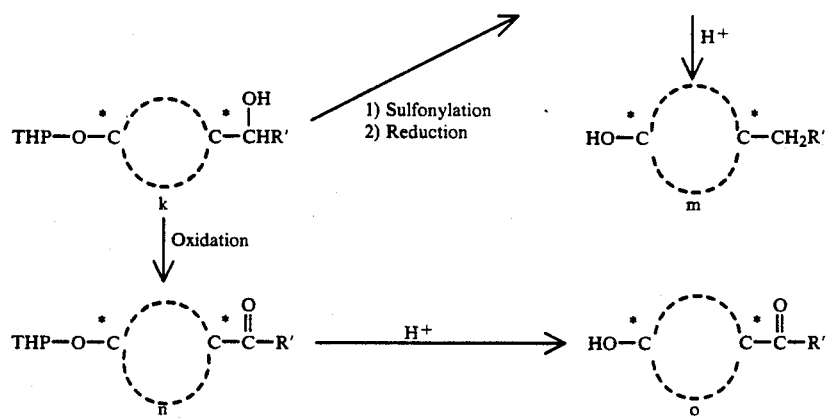

The compound a, which is a known compound, is subjected to asymmetric reduction according to the known method using baker's yeast (B. S. Doel et al., Aust. J. Chem., 29, 2459 (1976)); the resulting compound b is subjected to alkylation to obtain the compound c, and then to acidic hydrolysis to obtain the compound d. The other compounds are prepared by conventional procedures.

The compounds c, d, e, i, m, o and p are novel and useful for an intermediate of the liquid crystal compound.

Furthermore, the optically active cyclic compounds are prepared by the following methods such as enzymatic hydrolysis of the prochiral cyclic 1,2-diester [M. Schneider et al., Angew. Chem. Internat. Ed. Engl., 23, 67 (1984)] and the like.

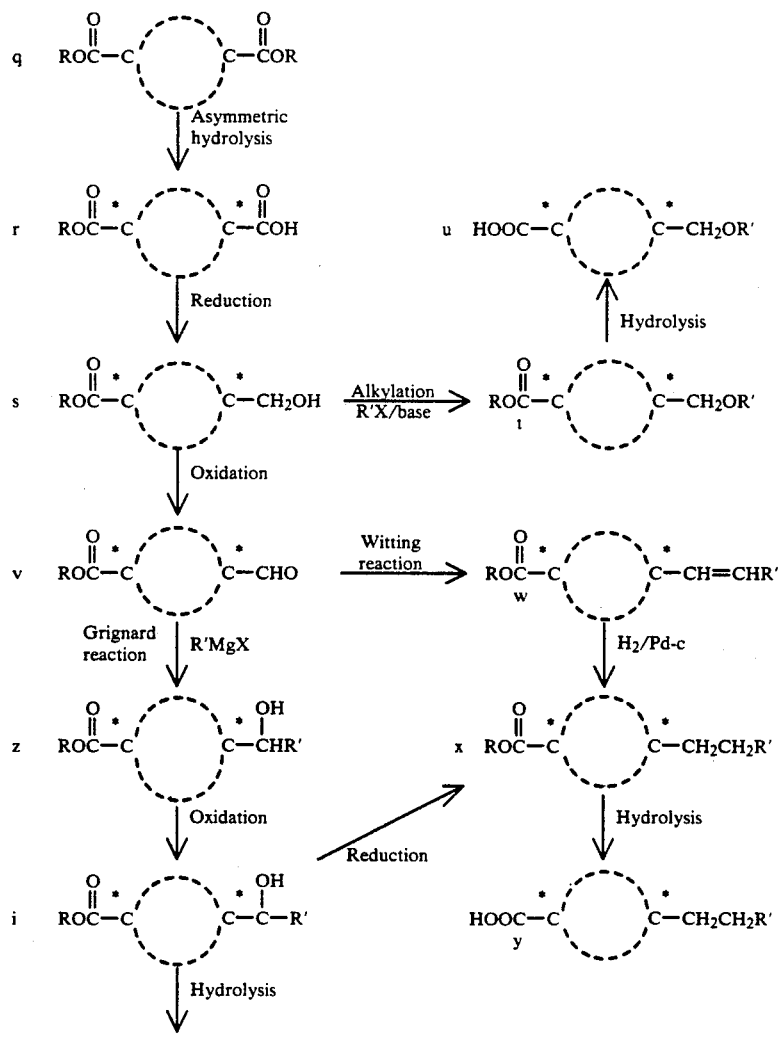

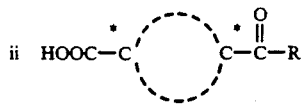

The compound g, which is a known compound, is subjected to asymmetric reduction. The followed compounds are prepared by conventional procedures.

The compounds t, u, x, y, i and ii are novel and useful for an intermediate of the liquid crystal compound.

By a similar manner as above, the optically active cyclic compounds are prepared from the prochiral substance as shown in the following methods [K. Sakai et al., Chem. Commun., 838 (1987), and 966 (1988)];

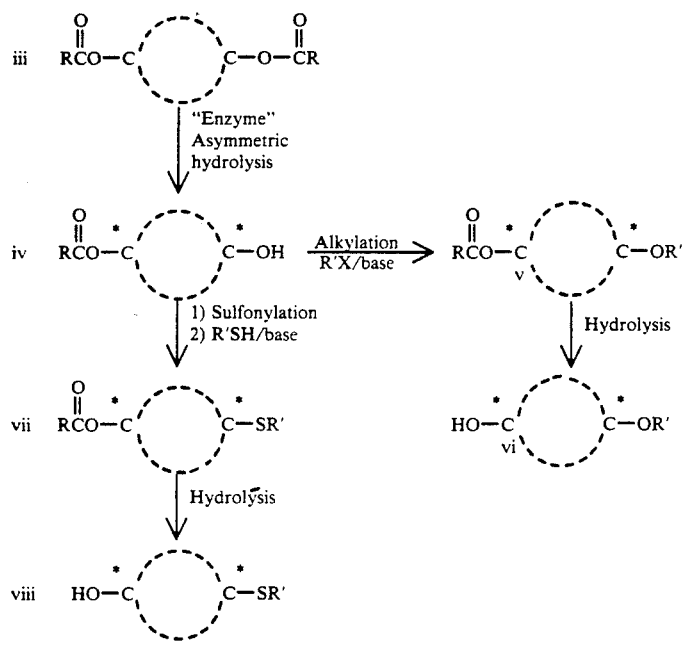

The compound iii, which is a known compound, is subjected to asymmetric reduction. The followed compounds are prepared by conventional procedures.

The compounds iv and viii are novel and useful for an intermediate of the liquid crystal compound.

Specific examples of the optically active dichiral cyclic secondary alcohol III and the optically active cyclic dichiral carboxylic acid V were shown above. Similar cyclic derivatives can be used, also when $Q_3$ is a single bond, a thioether group, a carbonyl group, a carbonyldioxy group or a methyleneoxy group. Therefore, the secondary alcohol III and the carboxylic acid V are not restricted to these examples.

Next, there are specifically described typical examples of the carboxylic acid II and the alcohol or phenolic hydroxyl group-containing compound IV which are both important materials for the skeletal portion of the optically active compounds of the present invention.

The carboxylic acid II can be classified into two type compounds represented by the following general formulas.

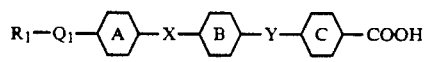  [II']

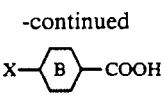 —COOH  [II'']

As typical examples of these compounds, there can be mentioned 4-(4'-alkyloxy or alkyl-4-biphenylcarbonyloxy)benzoic acid, 4-(4'-alkyloxy or alkyl-4-biphenyloxycarbonyl)benzoic acid, 4'-(4-alkyloxy or alkylphenylcarbonyloxy)-4-biphenylcarboxylic acids, 4'-(4-alkyloxy or alkylphenyloxycarbonyl)-4-biphenylcarboxylic acids, 4-alkyloxy or alkyl-4-biphenylcarboxylic acids, 4"-alkyloxy(or alkyl)-4-terphenylcarboxylic acids, 4'-(trans-4-alkyloxy or alkylcyclohexylcarbonyloxy)-4-biphenylcarboxylic acids, trans-4-(4'-alkyloxy or alkyl-4-biphenylcarbonyloxy)cyclohexanecarboxylic acids, 2-[4-(4-alkyloxy or alkylphenylcarbonyloxy)phenyl]pyridimidinyl-5-carboxylic acids, 2-(4'-alkyloxy or alkyl-4-biphenyl)pyrimidinyl-5-carboxylic acids, 4'-(5-alkyloxy or alkylpyrimidinyl-2-oxycarbonyl)biphenyl-4-carboxylic acids, 4'-[2-(5-alkyloxy or alkyl)-2-(pyridyl)ethyl]biphenyl-4-carboxylic acids, 4-[4-(trans-5-alkyloxy or alkyl-1,3-dioxane-2-yl)phenylcarbonyloxy]benzoic acids, 4'-[4-(trans-5-alkyloxy or alkyl-1,3-dioxane-2-yl)]biphenyl-4-carboxylic acids, 2-[4-(4-alkyloxy or alkylphenylcarbonyloxy)phenyl]pyrazinyl-5-carboxylic acids, 2-(4'-alkyloxy or alkyl-4-biphenyl)pyrazinyl-5-carboxylic acids, 4'-(5-alkyloxy or alkylpyrazinyl-2-oxycarbonyl)-biphenyl-4-carboxylic acids and 4'-(6-alkyloxy or alkyl-3-pyridazinyl)biphenyl-4-carboxylic acids.

The alcohol IV or the compound IV having a phenolic hydroxy group can be classified into two type compounds represented by the following general formulas.

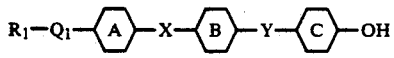

[IV']

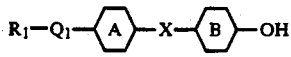

[IV"]

As typical examples of these compounds, there can be mentioned 4-hydroxyphenyl esters of 4'-alkyloxy or alkylbiphenyl-4-carboxylic acids, 4'-alkyloxy or alkyl-4-biphenyl esters of 4-hydroxybenzoic acids, 4'-hydroxy-4-biphenyl esters of 4-alkyloxy or alkylbenzoic acids, 4-alkyloxy or alkylphenyl esters of 4'-hydroxybiphenyl-4-carboxylic acids, 4'-hydroxy-4-biphenyl esters of trans-4-alkyloxy or alkylcyclohexanecarboxylic acids, trans-4-hydroxycyclohexyl esters of 4'-alkyloxy or alkyl-4-biphenylcarboxylic acids, 4-(5-hydroxy-2-pyrimidinyl)phenyl esters of 4-alkyloxy or alkylbenzoic acids, 2-(4'-alkyloxy or alkyl-4-biphenyl)pyrimidine-5-ols, 5-alkyloxy or alkyl-2-pyridinyl esters of 4'-hydroxy-4-biphenylcarboxylic acids, 4'-[2-(5-alkyloxy or alkyl-2-pyridyl)ethyl]biphenyl-4-ols, 4-hydroxyphenyl esters of 4-[4-(trans-5-alkyloxy or alkyl)-1,3-dioxane-2-yl]benzoic acids and 5-alkyloxy or 5-alkyl-2-pyrazinyl esters of 4'-hydroxy-4-biphenylcarboxylic acids.

The optically active compounds I of the present invention have a structure in which each asymmetric carbon atom bonds to oxygen or carbonyl, and therefore the compounds generally show high spontaneous polarization. In addition, most of the compounds I show a chiral smectic C (Sc*) phase which is a liquid crystal phase suitable for display methods utilizing the ferroelectric properties of liquid crystals, and the temperature range of the chiral smectic C phase is low and wide.

The optically active compounds of the present invention are very stable to heat, light, water and air. Accordingly, in putting the compounds to practical use as or in liquid crystal materials, there can be eliminated inconveniences such as arrangements of an apparatus for prevention of overheating, a glass frit seal for prevention of moisture absorption or permeation, etc.

The optically active compounds I of the present invention have excellent compatibility with conventionally known liquid crystal compounds such as those of Schiff's base type, biphenyl type, phenylcyclohexane type, heterocyclic type and the like. Therefore, the compounds can be made into liquid crystal compositions having excellent properties, by incorporating them into said liquid crystal compounds.

As the liquid crystal compounds into which the optically active compounds I of the present invention can be incorporated, there can be mentioned, for example, ferroelectric liquid crystal compounds as well as liquid crystal compounds showing a smectic C phase. The ferroelectric liquid crystal compounds include, for example, biphenyl type liquid crystals described in JP-A-118744/1984 and 13729/1985, ester type liquid crystals described in JP-A-128357/1984, 51147/1985, 22051/1986 and 249953/1986, and pyrimidine type liquid crsytals described in JP-A-260564/1985, 24756/1986, 85368/1986 and 215373/1986. The liquid crystal compounds showing a smectic C phase include, for example, ester type liquid crystal compounds described in JP-A-228036/1987, and cyclohexane type liquid crystals and heterocyclic type liquid crystals described in the materials of the 16th Freiburg Liquid Crystal Forum (Mar. 21, 1986) and the materials of the First International Symposium on Ferroelectric Liquid Crystals (Sep. 21, 1987).

The optically active compounds of the present invention can also be incorporated into the nematic or cholesteric liquid crystals described in "Flüssige Kristalle in Tabellen" I & II, VEB-Verlag, Leipzig, and further can be mixed with commercially available nematic liquid crystal compounds. When the optically active compounds of the present invention are incorporated into nematic liquid crystals, the twisting direction of the cholesteric pitch and the pitch length of the nematic liquid crystal compositions obtained can be freely controlled via the amount added.

When the optically active compound of the present invention is mixed with other liquid crystals as mentioned above, the mixing ratio can be selected depending upon the application purpose of the resulting liquid crystal composition. For example, when it is desired to prepare a ferroelectric liquid crystal composition, the optically active composition of the present invention can be used in an amount of 5-50% by weight based on the total weight of the composition; when a smectic liquid crystal composition is prepared, the compound of the present invention can be used in an amount of 0.1-5% by weight. It is also possible to formulate a liquid crystal composition using only the optically active compounds of the present invention.

As liquid crystal optical modulators, there can be mentioned various display apparatuses using a plurality of liquid crystal devices, for example, display apparatuses used in word processor, lap top type personal computer, work station, etc., image display apparatuses used in TV set, video telephone, etc. and terminal display panels of optical communication apparatuses.

Various types of liquid crystal display devices are known. The liquid crystal compositions of the present invention can be used in any liquid crystal display device as long as the compositions can exhibit the capabilities. The liquid crystal compositions of the present invention can be effectively used in, for example, the liquid crystal devices disclosed in U.S. Pat. No. 4,367,924, JP-B-63-22287, U.S. Pat. No. 4,563,059, etc.

Generally, these liquid crystal devices are basically constituted by a pair of substrates, two polarizing plates provided on the substrates, a pair of transparent electrodes, a pair of molecule polarizing layers, a liquid crystal composition sealed between the substrates by a sealing agent, and a reflecting plate.

The present invention is described more specifically by way of Examples and Application Examples.

The optically active compounds prepared in Examples were measured for phase, phase transition temperature and spontaneous polarization. The results are listed in Table 1 together with the elemental analysis.

Incidentally, phase and phase transition temperature were measured using a polarizing microscope and a differential scanning calorimeter (DSC).

Spontaneous polarization was measured by the Sowyer-Tower method. The values of spontaneous polarization were obtained at a temperature lower by 10° C. than the upper limit temperature of chiral smectic C phase.

The phases such as liquid crystal phase are shown by the following abbreviations.

| | | | |
|---|---|---|---|
| Iso: | isotropic phase | Ch: | cholesteric phase |

| | | | |
|---|---|---|---|
| SA: | smectic A phase | K: | crystalline phase |
| Sc*: | chiral smectic C phase | | |
| S₁, S₂: | smectic phases which are difficult to identify | | |

EXAMPLE 1

Preparation of 4'-octyloxy-4-biphenyl ester of cis-(1R,2S)-2-methoxycyclopentane-1-carboxylic acid (a compound of the general formula I" wherein $R_1$ is n-$C_8H_{17}$, $R_2$ is $CH_3$, $Q_1$ and $Q_3$ are both —O—, $Q_2$ is

X is a single bond, and

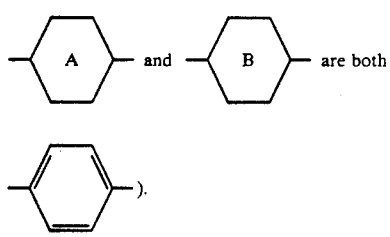

).

(i) Preparation of cis-(1R,2S)-2-methoxycyclopentane-1-carboxylic acid

This optically active cyclic dichiral carboxylic acid can be prepared according to the following scheme.

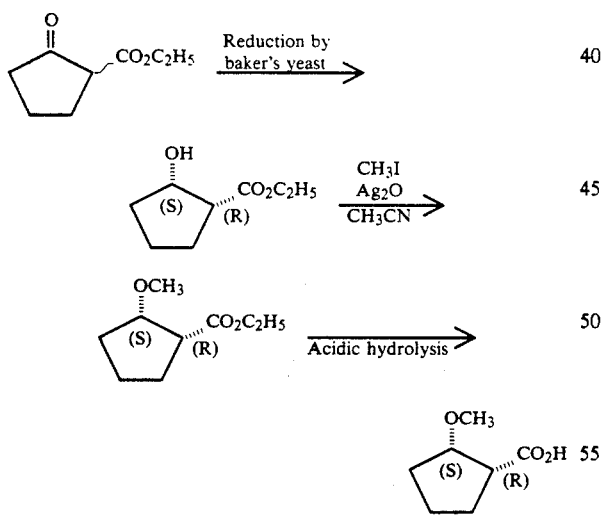

That is, ethyl 2-oxocyclopentane-1-carboxylate was subjected to asymmetric reduction according to the known method using baker's yeast [B. S. Doel et al., Aust. J. Chem., 29, 2459 (1976)]; the resulting ethyl cis-(1R,2S)-2-hydroxycyclopentane-1-carboxylate was subjected to methylation and then to acidic hydrolysis to obtain the title compound as a colorless oil. The IR and ¹H-NMR spectra of the compound are shown below.

IR $v_{max}^{neat}$ cm⁻¹: 2700–2400, 1710

¹H-NMR (90 MHz, CDCl₃) δ: 1.4–2.25(6H, m, CH₂), 2.6–3.05(1H, m, >CHCOO), 3.35(3H, s, OCH₃), 3.85–4.15(1H, m, >CHOCH₃), 7.7–8.6(1H, broad s, CO₂H)

The ¹H-NMR spectra of the ethyl ester of the title compound (as a colorless oil) are shown below.

¹H-NMR (90 MHz, CDCl₃) δ: 1.26(3H, t, J=7.5 Hz, OCH₂CH₃), 1.3–2.3(6H, m, CH₂), 2.6–3.1(1H, m, >CHCO₂Et), 3.28(3H, s, OCH₃), 3.8–4.4(3H, m, >CH-OCH₃ and CO₂CH₂CH₃)

(ii) Esterification 472.5 mg of the cis-(1R,2S)-2-methoxycyclopentane-1-carboxylic acid obtained in i) above was reacted with oxalyl chloride to obtain 382.5 mg of an acid chloride (IR $v_{max}^{neat}$ cm⁻¹: 1800). A solution of this acid chloride dissolved in 5.0 ml of dry toluene was added, with stirring, to a solution of 0.68 g of 4'-octyloxy-4-biphenol and 0.6 ml of pyridine dissolved in 10 ml of dry tetrahydrofuran. The mixture was stirred for 4 days at room temperature. The reaction mixture was concentrated under reduced pressure, and the residue was mixed with benzene. The insoluble materials were removed by filtration and the filtrate was concentrated under reduced pressure. The residue was subjected to column chromatography using silica gel (150 g) and carbon tetrachloride-ether (10:1). 0.44 g of the title compound was obtained from the relevant fraction as waxy crystals. The IR and ¹H-NMR spectra of the compound are shown below.

IR $v_{max}^{neat}$ cm⁻¹: 1755, 1500, 1245, 1210, 1165

¹H-NMR (90 MHz, CDCl₃) δ: 0.89(3H, t, J=6 Hz, —CH₂CH₃), 1.0–2.5(18H, m, CH₂), 2.9–3.4 (1H, m, >CH—COO), 3.39(3H, s, OCH₃), 3.99(2H, t, J=6 Hz, OCH₂), 3.9–4.25(1H, m, >CH—OCH₃), 6.75–7.6(8H, m, aromatic H)

EXAMPLE 2

Preparation of 4-(4'-octyloxy-4-biphenyloxycarbonyl)phenyl ester of cis-(1R,2S)-2-methoxycyclopentane-1-carboxylic acid (a compound of the general formula I' wherein $R_1$ is n-$C_8H_{17}$, $R_2$ is $CH_3$, $Q_1$ and $Q_3$ are both —O—, $Q_2$ is

X is a single bond, Y is

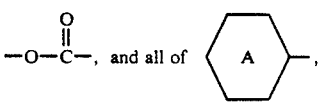, and all of

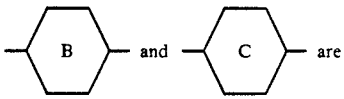 are

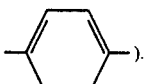).

Using 382.5 mg of cis-(1R,2S)-2-methoxycyclopentane-1-carboxylic acid chloride and 0.95 g of 4-(4'-octyloxy-4-biphenyloxycarbonyl)phenol and in the same procedure as in Example 1, there was obtained 0.65 g of the title compound as colorless powder (recrystallized from ethanol).

EXAMPLE 3

Preparation of 4'-(4-octyloxyphenyloxycarbonyl)-4-biphenyl ester of cis-(1R,2S)-2-methoxycyclopentane-1-carboxylic acid (a compound of the general formula I' wherein $R_1$ is n-$C_8H_{17}$, $R_2$ is $CH_3$, $Q_1$ and $Q_3$ are both —O—, $Q_2$ is

X is

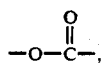

Y is a single bond, and all of

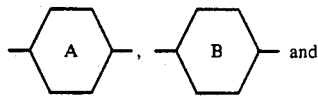

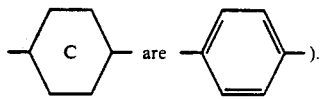

Using 382.5 mg of cis-(1R,2S)-2-methoxycyclopentane-1-carboxylic acid chloride and 0.95 g of 4-octyloxyphenyl 4'-hydroxy-4-biphenylcarboxylate and in the same procedure as in Example 1, there was obtained 0.51 g of the title compound as colorless needles (recrystallized from ethanol).

EXAMPLE 4

Preparation of 4'-(4-octyloxyphenylcarbonyloxy)-4-biphenyl ester of cis-(1R,2S)-2-methoxycyclopentane-1-carboxylic acid (a compound of the general formula I' wherein $R_1$ is n-$C_8H_{17}$, $R_2$ is $CH_3$, $Q_1$ and $Q_3$ are both —O—, $Q_2$ is

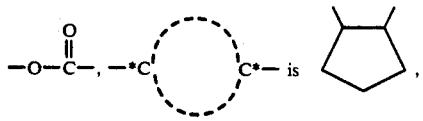

X is

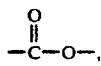

Y is a single bond, and all of

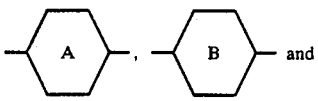

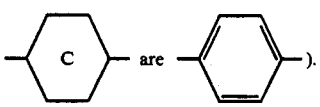

Using 382.5 mg of cis-(1R, 2S)-2-methoxycyclopentane-1-carboxylic acid chloride and 0.95 g of 4'-(4-octyphenylcarbonyloxy)-4-biphenol and in the same procedure as in Example 1, there was obtained 0.39 g of the title compound as colorless needles (recrystallized from ethyl acetate-ethanol).

EXAMPLE 5

Preparation of 4'-(4-n-octyloxyphenyloxycarbonyl)-4-biphenyl ester of cis-(1R,2S)-2-methoxycyclohexane-1-carboxylic acid (a compound of the general formula I' wherein $R_1$ is n-$C_8H_{17}$, $R_2$ is $CH_3$, $Q_1$ and $Q_3$ are both —O— $Q_2$ is

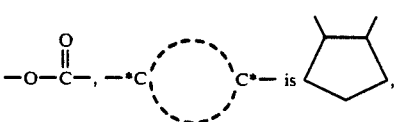

X is

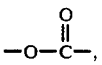

Y is a single bond, and all of

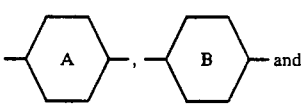

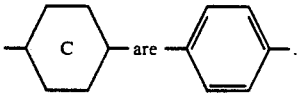

(i) Preparation of cis-(1R,2S)-2-methoxycyclohexane-1-carboxylic acid

This optically active cyclic dichiral carboxylic acid can be prepared according to the following scheme.

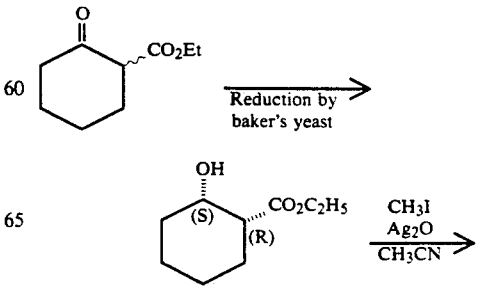

-continued

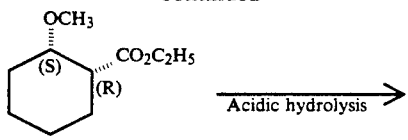

Acidic hydrolysis →

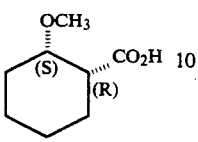

That is, ethyl 2-oxocyclohexane-1-carboxylate was subjected to asymmetric reduction according to the known method using baker's yeast [B. S. Doel et al., Aust. J. Chem., 29, 2459 (1979)], and the resulting ethyl cis-(1R,2S)-2-hydroxycyclohexane-1-carboxylate was subjected to methylation and then to acidic hydrolysis to obtain the title compound. The NMR spectra of the ethyl ester of the title compound which is a colorless oil are shown below.

$^1$H-NMR (90 MHz, CDCl$_3$) δ: 0.8–2.2(8H, m, CH$_2$), 1.25(3H, t, J=7 Hz, CO$_2$CH$_2$C$\underline{H}_3$), 2.2–2.55 (1H, m, >C$\underline{H}$CO$_2$Et), 3.29(3H, s, OC$\underline{H}_3$), 3.55–3.9(1H, m, >C$\underline{H}$OCH$_3$), 3.9–4.35(2H, m, CO$_2$C$\underline{H}_2$CH$_3$)

(ii) Esterification 4.0 g of the cis-(1R,2S)-2-methoxycyclohexane-1-carboxylic acid obtained in i) above was reacted with oxalyl chloride to obtain 2.2 g of an acid chloride (IR ν$_{max}$$^{neat}$ cm$^{-1}$: 1800 $^1$H-NMR (90 MHz, CDCl$_3$) δ: 0.85–2.55(8H, m, CH$_2$), 2.6–3.05(1H, m,

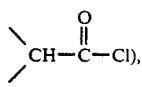

3.34(3H, s, OCH$_3$), 3.8–4.3(1H, m, >C$\underline{H}$—OCH$_3$)) 0.5 g of this acid chloride was added, with stirring, to a solution of 1.05 g of 4-octyloxyphenyl 4-hydroxy-4-biphenylcarboxylate and 0.6 g of pyridine dissolved in 10 ml of dry tetrahydrofuran. The mixture was subjected to a reaction overnight. The reaction mixture was concentrated under reduced pressure. The residue was subjected to separation and purification by column chromatography using silica gel and carbon tetrachloride-ether (30:1) and then recrystallized from ethanol to obtain 0.3 g of the title compound. The IR and $^1$H-NMR spectra of the compound are shown below.

IR ν$_{max}$$^{neat}$ cm$^{-1}$: 2800–3000, 1740, 1605

$^1$H-NMR (90 MHz, CDCl$_3$) δ: 0.89(3H, t) 1.1–2.0 (20H, m), 2.6–2.9(1H, m), 3.40(3H, s), 3.9–4.1 (3H, m), 6.8–8.3(12H, m)

EXAMPLE 6

Preparation of 4-(4'-n-octyloxy-4-biphenyloxycarbonyl)phenyl ester of cis-(1R,2S)-2-methoxycyclohexane-1-carboxylic acid (a compound of the general formula I' wherein R$_1$ is n-C$_8$H$_{17}$, R$_2$ is CH$_3$, Q$_1$ and Q$_3$ are both —O—, Q$_2$ is

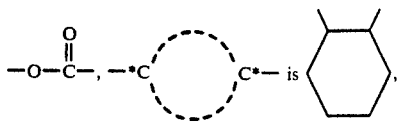

X is a single bond, Y is

and all of

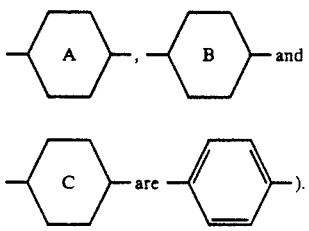

Using 0.50 g of cis-(1R,2S)-2-methoxycyclohexane-1-carboxylic acid chloride and 1.05 g of 4-(4'-octyloxy-4-biphenyloxycarbonyl)phenol and in the same procedure as in Example 5; there was obtained 0.38 g of the title compound (recrystallized from ethanol).

EXAMPLE 7

Preparation of 4'-octyloxy-4-biphenyl ester of cis-(1R,2S)-2-methoxycyclohexane-1-carboxylic acid (a compound of the general formula I" wherein R$_1$ is n-C$_8$H$_{17}$, R$_2$ is CH$_3$, Q$_1$ Q$_3$ are both —O—, Q$_2$ is

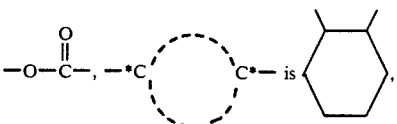

X is a single bond, and all of

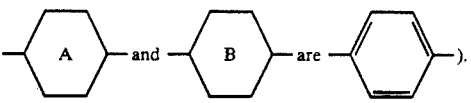

Using 0.7 g of cis(1R,2S)-2-methoxycyclohexane-1-carboxylic acid chloride and 1.05 g of 4'-octyloxy-4-biphenol and in the same procedure as in Example 5, there was obtained 0.62 g of the title compound.

EXAMPLE 8

Preparation of 4'-(4-octyloxyphenylcarbonyloxy)-4-biphenyl ester of cis-(1R,2S)-2-methoxycyclohexane-1-carboxylic acid (a compound of the general formula I' wherein R$_1$ is n-C$_8$H$_{17}$, R$_2$ is CH$_3$, Q$_1$ and Q$_3$ are both —O—, Q$_2$ is

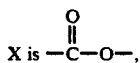

Y is a single bond and all of

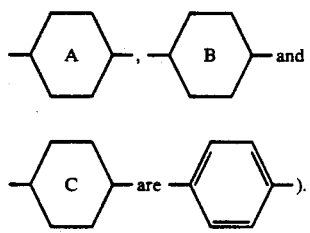

Using 0.50 g of cis-(1R, 2S)-2-methoxycyclohexane-1-carboxylic acid chloride and 1.05 g of 4'-hydroxy-4-biphenyl-4-octyloxybenzoate and in the same procedure as in Example 5, there was obtained 0.77 g of the title compound.

EXAMPLE 9

(i) Preparation of trans-(1S,2S)-2-methoxycyclopentane-1-carboxylic acid

The ethyl cis-(1R,2S)-2-hydroxycyclopentane-1-carboxylate prepared in Example 1 i) was subjected to inversion of configuration at the 1-position in ethanol in the presence of a base ($K_2CO_3$) to convert to ethyl trans-(1S,2S)-2-hydroxycyclopentane-1-carboxylate. This ester was subjected to methyl etherification and then to acidic hydrolysis to obtain the title compound.

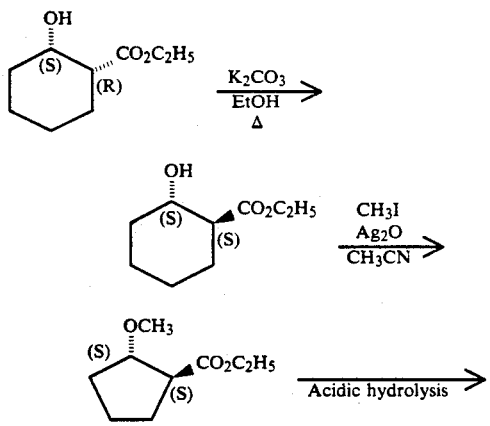

(ii) Esterification

The same procedure as in Example 1 ii) was repeated except that trans-(1S,2S)-2-methoxycyclopentane-1-carboxylic acid chloride was used in place of cis-(1R,2S)-2-methoxycyclopentane-1-carboxylic acid chloride and subjected to a condensation reaction with 4-octyloxyphenyl 4'-hydroxy-4-biphenylcarboxylate, whereby the title compound was obtained.

EXAMPLES 10 and 11

The trans-(1S,2S)-2-methoxycyclopentane-1-carboxylic acid obtained in Example 9 i) was converted to a corresponding acid chloride according to an ordinary method, and the acid chloride was subjected to a condensation reaction with a corresponding compound containing a phenolic hydroxyl group, to obtain compounds of Examples 10 and 11, respectively.

EXAMPLE 12

Preparation of 4-(4-octyloxyphenyloxycarbonyl)phenyl ester of cis-(1R,2S)-2-methoxycyclohexane-1-carboxylic acid (a compound of the general formula I" wherein $R_1$ is n-$C_8H_{17}$, $R_2$ is $CH_3$, $Q_1$ and $Q_3$ are both —O—, $Q_2$ is

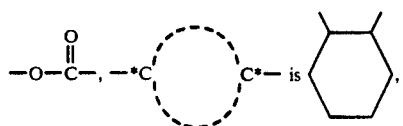

X is

and all of

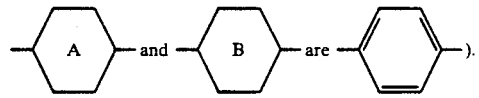

Using 0.68 g of cis-(1R,2S)-2-methoxycyclohexane-1-carboxylic acid chloride and 1.03 g of 4-(4-octyloxyphenyloxycarbonyl)phenol and in the same procedure as in Example 5, there was obtained 1.30 g of the title compound.

EXAMPLE 13

Preparation of 4'-octyloxycarbonyl-4-biphenyl ester of cis-(1R,2S)-2-methoxycyclohexane-1-carboxylic acid (a compound of the general formula I wherein $R_1$ is n-$C_8H_{17}$, $R_2$ is $CH_3$, $Q_1$ and $Q_2$ are both

$Q_3$ is —O—,

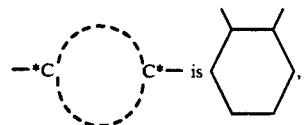

X is a single bond, and all of

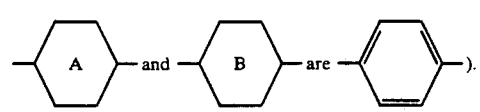

Using 0.80 g of cis-(1R,2S)-2-methoxycyclohexane-1-carboxylic acid chloride and 1.14 g of 4'-octyloxycarbonyl-4-biphenol and in the same procedure as in Example 5, there was obtained 0.80 g of the title compound.

EXAMPLE 14

Preparation of 4'-(4-octylphenoxycarbonyl)-4-biphenyl ester of cis-(1R,2S)-2-methoxycyclohexane-1-carboxylic acid (a compound of the general formula I' wherein $R_1$ is n-$C_8H_{17}$, $R_2$ is $CH_3$, $Q_1$ is a single bond, $Q_2$ is

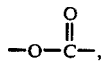

$Q_3$ is —O—,

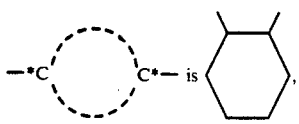

X is

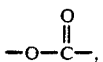

Y is a single bond, and all of

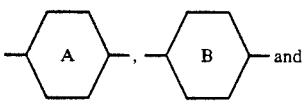

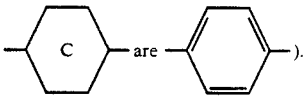

Using 0.57 g of cis-(1R,2S)-2-methoxycyclohexane-1-carboxylic acid chloride and 1.00 g of 4'-(4-n-octylphenyloxycarbonyl)-4-biphenol and in the same procedure as in Example 5, there was obtained 1.04 g of the title compound.

EXAMPLE 15

Preparation of 4-(4'-octyloxy-4-biphenylcarbonyloxy)phenyl ester of cis-(1R,2S)-2-methoxycyclohexane-1-carboxylic acid (a compound of the general formula I' wherein $R_1$ is n-$C_8H_{17}$, $R_2$ is $CH_3$, $Q_1$ and $Q_3$ are —O—, $Q_2$ is

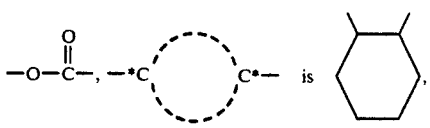

X is a single bond, Y is

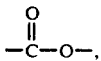

and all of

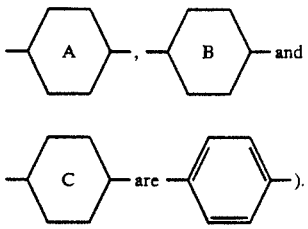

Using 0.57 g of cis-(1R,2S)-2-methoxycyclohexane-1-carboxylic acid chloride and 1.05 g of 4-(4'-octyloxy-4-biphenylcarbonyloxy)phenol and in the same procedure as in Example 5, there was obtained 1.05 g of the title compound.

EXAMPLE 16

Preparation of 4'-(4-n-propyloxyphenyloxycarbonyl)-4-biphenyl ester of cis-(1R,2S)-2-methoxycyclohexane-1-carboxylic acid (a compound of the general formula I' wherein $R_1$ is n-$C_3H_7$, $R_2$ is $CH_3$, $Q_1$ and $Q_3$ are both —O—, $Q_2$ is

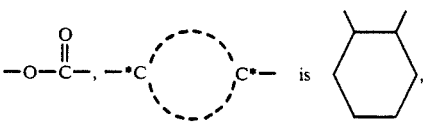

X is

Y is single bond, and all of

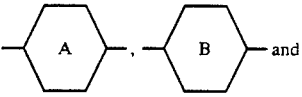

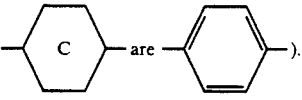

Using 0.69 g of cis-(1R,2S)-2-methoxycyclohexane-1-carboxylic acid chloride and 1.05 of 4'-(4-n-propyloxyphenyloxycarbonyl)-4-biphenol and in the same procedure as in Example 5, there was obtained 1.05 g of the title compound.

EXAMPLE 17

Preparation of 4'-decyloxy-4-biphenyl ester of cis-(1R,2S)-2-methoxycyclohexane-1-carboxylic acid (a compound of the general formula I" wherein $R_1$ is n-$C_{10}H_{21}$, $R_2$ is $CH_3$, $Q_1$ and $Q_3$ are both —O—, $Q_2$ is

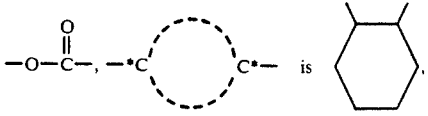

X is a single bond, all of

Using 0.69 g of cis-(1R,2S)-2-methoxycyclohexane-1-carboxylic acid chloride and 0.98 g of 4'-decyloxy-4-biphenol and in the same procedure as in Example 5, there was obtained 0.72 g of the title compound.

EXAMPLE 18

Preparation of 4'-dodecyloxy-4-biphenyl ester of cis-(1R,2S)-2-methoxycyclohexane-1-carboxylic acid (a compound of the general formula I″ wherein $R_1$ is n-$C_{12}H_{25}$, $R_2$ is $CH_3$, $Q_1$ and $Q_3$ are both —O—, $Q_2$ is

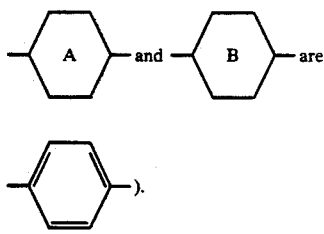

X is a single bond, and all of

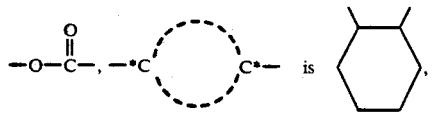

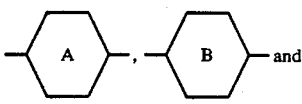

Using 0.69 g of cis-(1R,2S)-2-methoxycyclohexane-1-carboxylic acid chloride and 1.06 g of 4'-dodecyloxy-4-biphenol and in the same procedure as in Example 5, there was obtained 0.4 g of the title compound.

EXAMPLE 19

Preparation of 4'-(4-octyloxybenzyloxy)-4-biphenyl ester of cis-(1R,2S)-2-methoxycyclohexane-1-carboxylic acid (a compound of the general formula I' wherein $R_1$ is n-$C_8H_{17}$, $R_2$ is $CH_3$, $Q_1$ and $Q_3$ are both —O—, $Q_2$ is

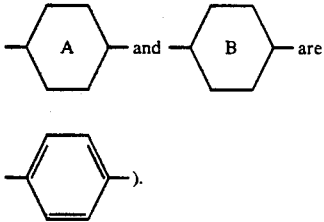

X is —$CH_2$—O—, Y is a single bond, and all of

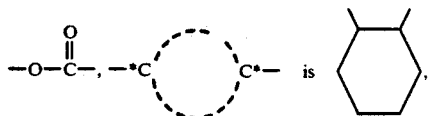

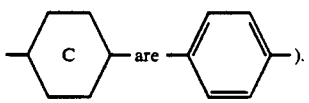

Using 0.57 g of cis-(2-methoxycyclohexane-1-carboxylic acid chloride and 1.01 g of 4'-(4-octyloxybenzyloxy)-4-biphenol and in the same procedure as in Example 5, there was obtained 0.32 g of the title compound.

EXAMPLE 20

Preparation of 4'-(4-n-octyloxyphenylcarbonyloxy)-4-biphenyl ester of cis-(1R,2S)-2-butoxycyclopentane-1-carboxylic acid (a compound of the general formula I' wherein $R_1$ is n-$C_8H_{17}$, $R_2$ is —Bu(n), $Q_1$ and $Q_3$ are both —O—, $Q_2$ is

X is

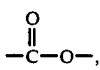

Y is a single bond, and all of

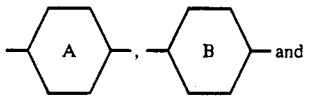

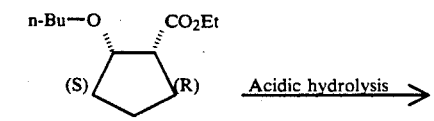

(1) Preparation of cis-(1R,2S)-2-butoxycyclopentane-1-carboxylic acid

This optically active cyclic dichiral carboxylic acid can be prepared according to the following scheme.

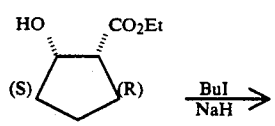

The ethyl cis-(1R,2S)-2-hydroxycyclopentane-1-carboxylate obtained in Example 1 i) was subjected to butylation and then to acidic hydrolysis to obtain the title compound. The NMR spectra of the ethyl ester of the title compound are shown below:

$^1$H-NMR (90 MHz, CDCl$_3$) δ: 0.7–1.05(3H, m, CH$_3$), 1.05–2.5(10H, m, CH$_2$), 1.26(3H, t, J=7.15 Hz, OCH$_2$C$\underline{H}_3$), 2.6–3.0(1H, m, CHCO$_2$Et), 3.1–3.6 (2H, m, OC$\underline{H}_2$CH$_2$—), 3.85–4.3(1H, m, >CHOBu), 4.14(2H, q, J=7.15 Hz,

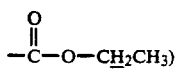

(ii) Esterification 1.0 g of the cis-(1R,2S)-2-butoxycyclopentane-1-carboxylic acid obtained in i) above was reacted with oxalyl chloride to obtain 0.70 g of an acid chloride (IR $\nu_{max}^{neat}$ cm$^{-1}$: 1800). 0.35 g of this acid chloride was added, with stirring at room temperature, to a solution of 0.71 g of 4′-(4-n-octyloxyphenylcarbonyloxy)-4-biphenyl ester and 0.4 g of pyridine dissolved in 10 ml of dry tetrahydrofuran. The mixture was subjected to a reaction overnight. The reaction mixture was concentrated under reduced pressure. The residue was subjected to separation and purification by column chromatography using carbon tetrachloride-ether (30:1) and silica gel and then recrystallized from ethanol to obtain 0.63 g of the title compound.

EXAMPLE 21

Preparation of 4-(4′-octyloxy-4-biphenyloxycarbonylphenyl ester of cis-(1R,2S)-2-butoxycyclopentane-1-carboxylic acid (a compound of the general formula I′ wherein R$_1$ is n-C$_8$H$_{17}$, R$_2$ is Bu(n), Q$_1$ and Q$_3$ are both —O—, Q$_2$ is

X is a single bond, Y is

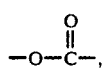

and all of

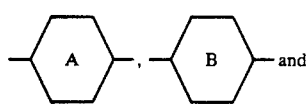

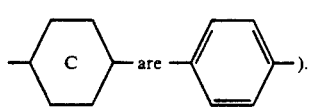

Using 0.35 g of cis-(1R,2S)-2-butoxycyclopentane-1-carboxylic acid chloride and 0.71 g of 4-(4′-octyloxy-4-biphenyloxycarbonyl)phenol and in the same procedure as in Example 1, there was obtained 0.78 g of the title compound.

EXAMPLE 22

(i) Cis-(1R,2S)-2-methoxy-1-methylcyclopentanecarboxylic acid

The ethyl cis-(1R,2S)-2-hydroxycyclopentanecarboxylate prepared in Example 1 i) was subjected to methylation, methyl etherification and hydrolysis in this order according to the method by Fra'ter et al. [Tetrahedron, 40, 1269 (1984)] and the method by Mori and Ebara [Tetrahedron, 42, 4413 (1986)] to obtain the title compound as a colorless oil (the following scheme).

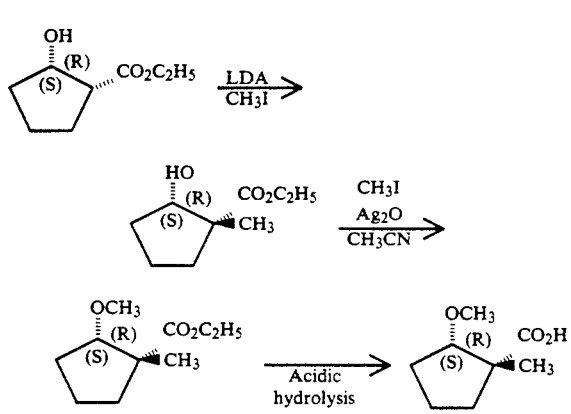

The IR spectrum of the compound is shown below.
IR $\nu_{max}^{neat}$ cm$^{-1}$: 1700–2300, 1700

(ii) Esterification

The compound of Example 22 shown in Table 1 was obtained in the same procedure as in Example 1 ii).

EXAMPLES 23–25

The compounds of Examples 23–25 shown in Table 1 were obtained by subjecting the cis-(1R,2S)-2-methoxy-1-methylcyclopentanecarboxylic acid obtained in Example 22 (i), to a condensation reaction with an appropriate skeletal compound in accordance with the above methods, for example, the method of Example 1 (ii).

EXAMPLE 26

Preparation of 4′-octyloxy-4-biphenyl ester of 4-[trans-(1R,2S)-2-methoxymethyl-1-cyclopentyloxy]-benzoic acid (i) Preparation of cis-(1S,2S)-2-methoxymethylcyclopentanol This optically active cyclic dichiral alcohol can be prepared according to the following scheme.

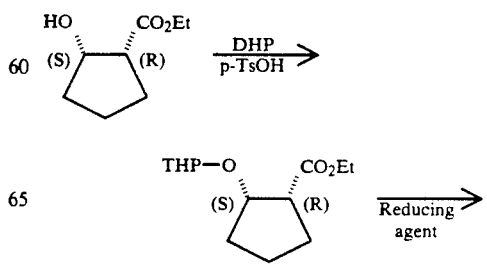

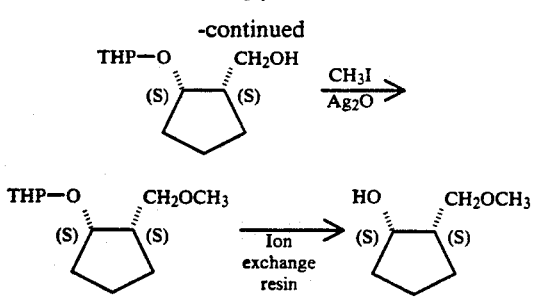

That is, the ethyl cis-(1R,2S)-2-hydroxycyclopentanecarboxylate obtained in Example 1 was subjected to tetrahydropyranylation, reduction by lithium aluminum hydride, methylation and detetrahydropyranylation by ion exchange resin in this order, to obtain the title compound. The IR and $^1$H-NMR spectra of the compound are shown below.

IR $\nu_{max}^{neat}$ cm$^{-1}$: 3200–3700, 2800–3000, 1740

$^1$H-NMR (90 MHz, CDCl$_3$) δ: 1.4–1.9 (6H, m), 2.3–2.5(1H, broad), 3.36(s, 3H), 3.52(1H, s), 3.6(1H, s), 4.2–4.4(m, 2H)

(ii) Etherification 0.49 g of the optically active alcohol obtained in i) above, 1.05 g of 4'-octyloxy-4-biphenyl 4-hydroxybenzoate and 0.98 g of triphenylphosphine were dissolved in 10 ml of dry tetrahydrofuran. To the solution was added 0.65 g of diethyl azodicarboxylate with stirring at room temperature. The reaction mixture was stirred for 1 hour at room temperature. Then, the solvent was removed by distillation. The residue was subjected to column chromatograph using silica gel and carbon tetrachloride-ether (30:1) to obtain 0.60 g of the title compound.

The IR and $^1$H-NMR spectra are shown below.

IR $\nu_{max}^{neat}$ cm$^{-1}$: 800–3000, 1735, 1605

$^1$H-NMR (90 MHz, CDCl$_3$) δ: 0.9(t, 3H), 1.2–1.5(m, 12H), 1.6–2.0(m, 6H), 2.2–2.5 (m, 1H), 3.34(t, 5H), 4.0(d, 2H), 4.6–4.8 (m, 1H), 6.9–8.2(m, 12H)

EXAMPLE 27

Preparation of 4-[trans-(1R,2S)-2-methoxymethyl-1-cyclopentoxy]phenyl ester of 4'-octyloxy-4-biphenylcarboxylic acid Using 0.49 g of cis-(1S,2S)-2-methoxymethylcyclopentanol and 1.05 g of 4-hydroxyphenyl 4'-octyloxy-4-biphenylcarboxylate and in the same procedure as in Example 26, there was obtained 0.70 g of the title compound.

EXAMPLE 28

Preparation of 4'-[trans-(1R,2S)-2-methoxymethyl-1-cyclopentyloxy]-4-biphenyl ester of 4-octyloxybenzoic acid Using 0.49 g of cis-(1S,2S)-2-methoxymethylcyclopentanol and 1.05 g of 4'-hydroxybiphenyl 4-octyloxybenzoate and in the same procedure as in Example 26, there was obtained 0.61 g of the title compound.

EXAMPLE 29

Preparation of 4-octyloxyphenyl ester of 4'-[trans(1R,2S)-2-methoxymethyl-1-cyclopentyloxy]-4-biphenylcarboxylic acid Using 0.49 g of cis-(1S,2S)-2-methoxymethylcyclopentanol and 1.05 g of 4-octyloxyphenyl 4'-hydroxybiphenyl-4-carboxylate and in the same procedure as in Example 26, there was obtained 0.76 g of the title compound.

EXAMPLE 30

Preparation of trans (1R,2S)-2-methoxymethyl-1-cyclopentyl ester of 4'-octyloxy-4-biphenylcarboxylic acid Using 0.59 g of cis-(1S,2S)-2-methoxymethyl-1-cyclopentanol and 4'-octyloxy-4-biphenylcarboxylic acid and in the same procedure as in Example 26, there was obtained 0.35 g of the title compound.

EXAMPLE 31

Preparation of 4'-octyloxy-4-biphenyl ether of trans-(1R,2S)-2-methoxymethyl-1-cyclopentanol Using 0.68 g of cis-(1S,2S)-2-methoxymethyl-1-cyclopentanol and 4'-octyloxy-4-biphenol and in the same proceudre as in Example 26, there was obtained 0.78 g of the totel compound.

EXAMPLE 32

Preparation of cis-(1S,2S)-2-methoxymethyl-1-cyclopentyl ester of 4-(4'-octyloxy-4-biphenyloxycarbonyl)-benzoic acid (i) Esterification 20 ml of thionyl chloride was added to 1.11 g of 4-(4'-octyloxy-4-biphenyloxycarbonyl)benzoic acid. The mixture was refluxed for 3 hours. The reaction mixture was concentration under reduced pressure. To the residue was added 20 ml of thionyl chloride, and the mixture was refluxed for 4 hours. The reaction mixture was concentrated under reduced pressure. To the residue was added toluene, and the mixture was subjected to azoetropic distillation to remove excessive thionyl chloride and toluene. To the residue was added 25 ml of dry tetrahydrofuran to dissolve the residue. To the resulting solution were added 0.39 g of cis(1S,2S)-2-methoxymethyl-1-cyclopentanol and 0.40 g of pyridine. The mixture was stirred overnight at room temperature. The reaction mixture was concentrated under reduced pressure. The residue was subjected to column chromatography using silica gel and carbon tetrachloride-ether (30:1) to obtain 0.10 g of the title compound.

EXAMPLE 33

The compound of this Example shown in Table 1 was obtained in the same manner as in Example 32.

EXAMPLES 34–45

The compounds of these Examples shown in Table 1 were obtained by subjecting cis-(1R,2S)-2-methoxycyclopentanecarboxylic acid chloride to a condensation reaction with an appropriate skeletal compound in the same procedure as in Example 1.

EXAMPLE 46

(i) Preparation of cis-(1S,2S)-1-hydroxymethyl-2-methoxychclopentane

The compound described in Example 1 i), i.e. ethyl cis-(1R,2S)-2-hydroxycyclopentanecarboxylate was reduced with lithium aluminum hydride to obtain the title compound (the following reaction formula).

(ii) Condensation

The compound of Example 46 shown in Table 1 was obtained in the same procedure as in Example 26 (ii).

EXAMPLE 47

Preparation of 4'-octyloxy-4-biphenyl ester of cis-(1R,2S)-2-methoxycarbonylchclohex-4-enecarboxylic acid 3 ml of oxalyl chloride was added, with ice cooling, to 0.25 g of the cis-(1R,2S)-2-methoxycarbonylcyclohex-4-enecarboxylic acid prepared according to the known method [M. Ohno et al., Tetrahedron Lett., 24, 2557 (1984)]. The mixture was stirred for 2 hours. Excessive oxalyl chloride was removed by distillation. To the remaining crude acid cloride were added 5 ml of dry tetrahydrofuran and 0.30 g of 4'-octyloxy-4-biphenol. To the mixture was dropwise added 0.11 g of triethylamine with ice cooling. The mixture was stirred for 1 hour. The reaction mixture was concentrated under reduced pressure. The residue was mixed with carbon tetrachloride. The resulting insoluble materials were removed by filtration. The filtrate was concentrated under reduced pressure. The residue was subjected to separation and purification by column chromatography using silica gel and carbon tetrachloride-ethyl acetate (20:1) and then to recrystallization from ethanol to obtain 0.31 g of the title compound as colorless plates. The IR and $^1$H-NMR spectra of the compound are shown below.

IR $\nu_{max}^{KBr}$ cm$^{-1}$: 1760, 1730

$^1$H-NMR (90 MHz, CDCl$_3$) δ: 0.89(3H, t, —CH$_2$CH$_3$) 1.12–2.00(12H, m, CH$_2$), 2.18–2.95(4H, m, CH$_2$—C=C—CH$_2$), 3.10–3.42(2H, m, —OOC—CH—CH—COO—), 3.72(3H, s, OCH$_3$), 3.98(2H, t, J=6 Hz, OCH$_2$), 5.73(2H, m, CH=CH), 6.85–7.60(8H, m, aromatic H)

EXAMPLE 48

Preparation of 4'-(4-octyloxyphenyloxycarbonyl)-4-biphenyl ester of cis-(1R,2S)-2-methoxycarbonylcyclohex-4-enecarboxylic acid Using 0.22 g of cis-(1R,2S)-2-methoxycarbonylcyclohex-4-enecarboxylic acid and 0.50 g of 4'-(4-octyloxyphenyloxycarbonyl)-4-biphenol and in the same procedure as in Example 47, there was obtained 0.42 g of the title compound.

EXAMPLE 49

Preparation of 4'-(4-octyloxyphenyloxycarbonyl)-4-biphenyl ester of cis(1R,2S)-2-methoxycarbonylcyclohexanecarboxylic acid In 10 ml of chloroform was dissolved 0.20 g of the 4'-(4-octyloxyphenyloxycarbonyl)-4-biphenyl ester of cis-(1R,2S)-2-methoxycarbonylcyclohex-4-enecarboxylic acid, obtained in Example 48. Thereto was added 30 mg of 5% palladium carbon. The mixture was subjected to hydrogenation at room temperature at atmospheric pressure. After the completion of the reaction, the catalyst was removed by filtration. The filtrate was concentrated under reduced pressure. The residue was recrystallized from ethanol to obtain 0.18 g of the title compound. The IR and $^1$H-NMR spectra of the compound are shown below.

IR $\nu_{max}^{KBr}$ cm$^{-1}$: 1760, 1725

$^1$H-NMR (90 MHz, CDCl$_3$) δ: 0.89(3H, t, —CH$_2$CH$_3$), 1.15–2.47(20H, m, CH$_2$), 2.93–3.20(2H, m, OOC—CH—CH—COO—), 3.72(3H, s, OCH$_3$), 3.96(2H, t, J=6 Hz, OCH$_2$), 6.82–8.30(12H, m, aromatic H)

EXAMPLE 50

Preparation of 4'-octyloxy-4-biphenyl ester of cis-(1R,2S)-2-methoxycarbonylcyclohexanecarboxylic acid 0.18 g of the 4'-octyloxy-4-biphenyl ester of cis-(1R,2S)-2-methoxycarbonylcyclohex-4-enecarboxylic acid, obtained in Example 47 was subjected to the same procedure as in Example 49 to obtain 0.15 g of the title compound.

EXAMPLE 51

Preparation of cis-(3R,4S)-tetrahydro-3-methoxycarbonyl-4-thienyl ester of 4-(4'-octyloxy-4-biphenylcarbonyloxy)benzoic acid (i) Preparation of methyl cis-(3R,4S)-tetrahydro-4-trimethylsilyloxythiophene-3-carboxylate This optically active cyclic dichiral compound can be prepared according to the following scheme.

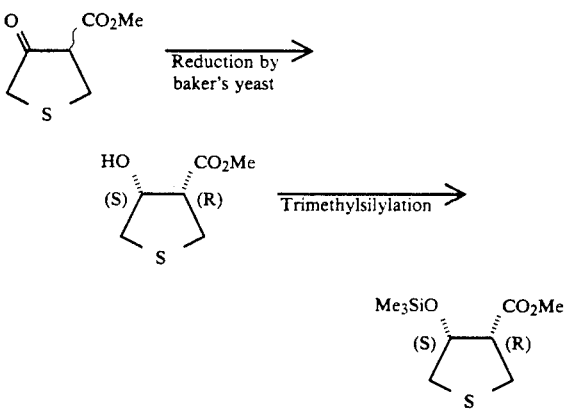

Methyl tetrahydro-4-oxothiophene-3-carboxylate was subjected to asymmetric reduction using baker's yeast according to the known method [R. W. Hoffmann et al., Tetrahedron Lett, 23. 3479 (1982)], and the resulting methyl cis-(3R,4S)-tetrahydro-4-hydroxythiophene-3-carboxylate was subjected to trimethylsilylation by 1,1,1,3,3,3-hexamethyldisilazane according to a conventional method, to obtain the title compound. The IR and $^1$H-NMR spectra of the compound are shown below.

IR $\nu_{max}^{neat}$ cm$^{-1}$: 1740

$^1$H-NMR (90 MHz, CDCl$_3$) δ: 0.11 (9H, s, —Si(CH$_3$)$_3$), 2.70–3.40(5H, m,

—CH$_2$SCH$_2$CH—CO$_2$—), 3.70(3H, s, OCH$_3$), 4.83(1H, m, >CH—OSi)

(ii) Esterification 0.50 g of 4-(4'-octyloxy-4-biphenylcarbonyloxy)benzoic acid was mixed with 10 ml of thionyl chloride, and the mixture was refluxed for 4 hours. Excessive thionyl chloride was removed by distillation. To the remaining crude acid chloride were added 20 ml of dry acetonitrile, 15 mg of zinc chloride and 0.26 g of the methyl cis-(3R,4S)-tetrahydro-4-trimethylsilyloxythiophene-3-carboxylate, obtained in i) above. The mixture was refluxed for 1 hour. After the completion of the reaction, the reaction mixture was concentrated. The residue was subjected to separation and purification by column chromatography using silica gel and dichloromethane-ethyl acetate (10:1) and then to recrystallization from dichloromethane-methanol (1:10) to obtain 0.36 g of the title compound as colorless powdery crystals. The IR and $^1$H-NMR spectra are shown below.

IR $\nu_{max}^{KBr}$ cm$^{-1}$: 1740, 1720

$^1$H-NMR (90 MHz, CDCl$_3$) δ: 0.90(3H, t, —CH$_2$C$\underline{H}_3$), 1.10–2.00(12H, m, CH$_2$), 3.03–3.56(5H, m,

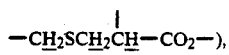

3.68(3H, s, OCH$_2$), 4.02(2H, t, J=6 Hz, OCH$_2$), 5.97(1H, m, >CH—OSi), 6.88–8.30(12H, m, aromatic H)

EXAMPLE 52

Preparation of cis-(3R,4S)-tetrahydro-3-methoxycarbonyl-4-thienyl ester of 4'-octyloxy-4-biphenylcarboxylic acid Using 0.36 g of methyl cis-(3R,4S)-tetrahydro-4-trimethylsilyloxythiophene-3-carboxylate and 0.50 g of 4'-octyloxy-4-biphenylcarboxylic acid and in the same procedure as in Example 51, there was obtained 0.42 g of the title compound as colorless powdery crystals [recrystalized from dichloromethane-methanol (1:10)]

EXAMPLE 53

Preparation of cis-(3R,4S)-tetrahydro-3-methoxycarbonyl-4-thienyl ester of 4-(4'-octyloxy-4-biphenyloxycarbonyl)benzoic acid Using 0.26 g of methyl cis-(3R,4S)-tetrahydro-4-trimethylsilyloxythiophene-3-carboxylate and 0.50 g of 4-(4'-octyloxy-4-biphenyloxycarbonyl)benzoic acid and in the same procedure as in Example 51, there was obtained 0.14 g of the title compound as colorless powdery crystals [recrystallized from dichloromethane-methanol (1:10)].

EXAMPLE 54

Preparation of cis-(2R,3S)-tetrahydro-2-methoxycarbonyl-3-thienyl ester of 4-(4'-octyloxy-4-biphenylcarbonyloxy)benzoic acid

(i) Preparation of methyl cis-(2R,3S)-tetrahydro-3-trimethylsilyloxythiophene-2-carboxylate This optically active cyclic dichiral compound can be prepared according to the following scheme.

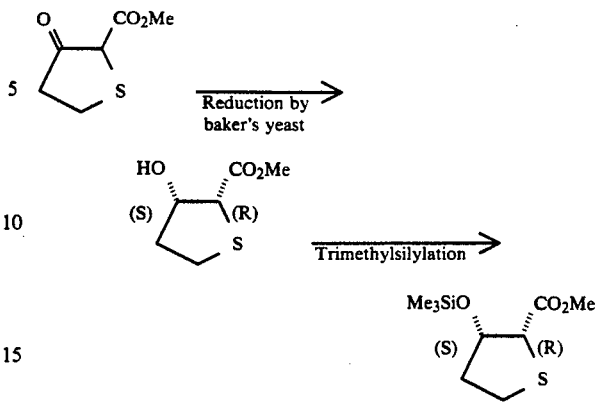

Methyl tetrahydro-3-oxothiophene-2-carboxylate was subjected to asymmetric reduction using baker's yeast according to the known method [R. W. Hoffmann et al., Tetrahedron Lett., 23, 3479 (1982)], and the resulting methyl cis-(2R, 3S)-tetrahydro-3-hydroxythiophene-2-carboxylate was subjected to trimethylsilylation by 1,1,1,3,3,3-hexamethyldisilazane according to a conventional method to obtain the title compound. The IR and $^1$H-NMR spectra of the compound are shown below.

IR $\nu_{max}^{neat}$ cm$^{-1}$: 1740

$^1$H-NMR (90 MHz, CDCl$_3$) δ: 0.12(9H, s, —Si(CH$_3$)$_3$), 2.78–3.30(4H, m, —C$\underline{H}_2$—C$\underline{H}_2$—S), 3.72(3H, s, —OC$\underline{H}_3$), 3.89(1H, d,

4.80 (1H, m, >C$\underline{H}$—OSi)

(ii) Esterification 10 ml of thionyl chloride was added to 0.70 g of 4-(4'-octyloxy-4-biphenylcarbonyloxy)benzoic acid. The mixture was refluxed for 4 hours. Excessive thionyl chloride was removed by distillation. To the remaining crude acid chloride were added 15 ml of dry acetonitrile, 27 mg of zinc chloride and 0.40 g of the methyl cis-(2R,3S)-tetrahydro-3-trimethylsilylthiophene-2-carboxylate. The mixture was refluxed for 1 hour. After the completion of the reaction, the reaction mixture was concentrated. The residue was subjected to separation and purification by column chromatography using silica gel and n-hexane-ethyl acetate (10:1) and then to recrystallization from ethanol to obtain 0.15 g of the title compound as colorless powder. The $^1$H-NMR spectrum of the compound is shown below.

$^1$H-NMR (90 MHz, CDCl$_3$) δ: 0.90 (3H, t, —CH$_2$C$\underline{H}_3$), 1.15–1.60(10H, b, —CH$_2$—), 1.60–1.98(2H, m, —OCH$_2$C$\underline{H}_2$CH$_2$—), 2.21–2.87(2H, m,

2.91–3.40 (2H, m, —CH$_2$—C$\underline{H}_2$—S—), 3.60(3H, s, OCH$_3$), 4.02(2H, t, —OCH$_2$—), 4.32(1H, d, >CH—S), 5.78(1H, d, t, >CH—O—), 6.94–8.26(12H, m, aromatic H)

EXAMPLE 55

Preparation of 4'-octyloxy-4-biphenyl ester of cis-(3R,4S)-tetrahydro-4-methoxyfuran-3-carboxylic acid (i) Preparation of ethyl cis-(3R,4S)-tetrahydro-4-methoxy-furan-3-carboxylate This optically active cyclic dichiral ethyl carboxylate can be prepared according to the following scheme.

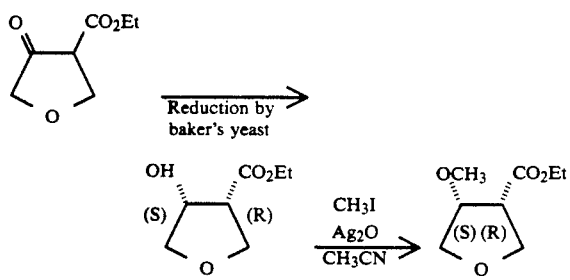

Ethyl 4-oxotetrahydrofuran-3-carboxylate was subjected to asymmetric reduction using baker's yeast and the resulting ethyl cis-(3R,4S)-4-hydroxy-tetrahydrofuran-3-carboxylate was subjected to methylation to obtain the title compound.

The IR and $^1$H-NMR spectra of the compound are shown below.

IR $\nu_{max}^{neat}$ cm$^{-1}$: 1740

$^1$H-NMR (90 MHz, CDCl$_3$) δ: 1.30(3H, t, —OCH$_2$C$\underline{H}_3$), 3.30(3H, s, —OCH$_3$), 3.43–3.57

(1H, m, H$\underline{C}$—CO$_2$Et), 4.17(2H, q, —OC$\underline{H}_2$CH$_3$), 3.70–4.45(5H, m, $\underline{H}$C—OCH$_3$, —CH$_2$—O—CH$_2$—)

(ii) Esterification 200 mg of the ethyl cis-(3R,4S)-tetrahydro-4-methoxyfuran-3-carboxylate obtained in i) above was added to a mixture of 2 ml of dioxane and 2 ml of 2N hydrochloric acid. The resulting mixture was stirred for 5 hours at 80° C. to effect acidic hydrolysis. 180 mg of the resulting crude carboxylic acid (IR $\nu_{max}^{neat}$ cm$^{-1}$: 1705) was reacted with 2 ml of oxalyl chloride to obtain 200 mg of a corresponding acid chloride (IR $\nu_{max}^{neat}$ cm$^{-1}$: 1790). The acid chloride was added to a solution of 596 mg of 4-octyloxy-4-biphenol and 202 mg of triethylamine dissolved in 10 ml of dry tetrahydrofuran, with stirring at room temperature. The mixture was stirred overnight and the reaction mixture was concentrated under reduced pressure. The residue was subjected to column chromatography (developing solvent: chloroform) to obtain 190 mg of the title compound. The IR and $^1$H-NMR spectra of the compound are shown below.

IR $\nu_{max}^{KBr}$ cm$^1$: 1760, 1610, 1500, 1170

$^1$H-NMR (90 MHz, CDCl$_3$) δ: 0.90(3H, t, —CH$_2$C$\underline{H}_3$), 1.10–2.00(12H, m, —CH$_2$—), 3.33–3.60

(1H, m, —C$\underline{H}$—C(=O)—O—), 3.47(3H, s, —OCH$_3$), 3.83–4.47(5H, m, —CH$_2$OCH$_2$—, —C$\underline{H}$—OCH$_3$),

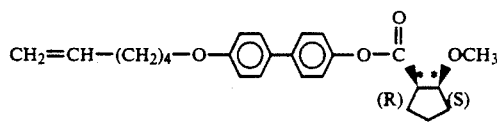
4.00(2H, t, —CH$_2$O—⌬—), 6.85–7.60(8H, m, aromatic H)

EXAMPLE 56

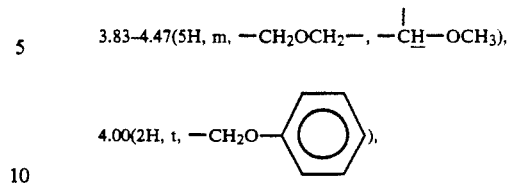

Using 0.56 g of cis-(1R,2S)-2-methoxycyclopentan-1-carboxylic chloride and 0.93 g of the sleletal compound, 4'-(5-hexenyl)oxy-4-biphenol, and in the procedure same as that of Example 1, there was obtained 0.70 g of the title compound as an oil. $^1$H-NMR spectra data of the present compound is shown as below.

$^1$H-NMR (CDCl$_3$) δ: 1.35 to 2.40(14H, m, —CH$_2$—), 3.10(1H, m,

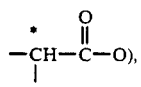
—C$\underline{H}$—C(=O)—O), 3.39(1H, S, —OCH$_3$), 3.98(2H, t, J=6 Hz, —O—CH$_2$—), 4.10(1H, m, —C*H—OCH$_3$), 5.0(2H, t, J=8.5 Hz, CH$_2$=C<), 5.60 to 5.78 (1H, m, >C=CH—), 6.80 to 7.60(8H, m,

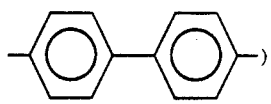
—⌬—⌬—)

EXAMPLE 57

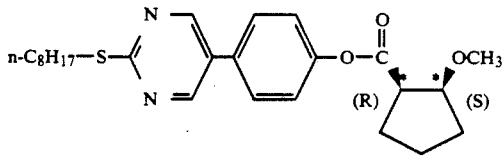

Using 0.50 g of cis-(1R,2S)-2-methoxycyclopentan-1-carboxylic chloride and 0.88 g of the skeletal compound, 4-(2-octylthio-5-pyrimidinyl) phenol, and in the procedure same as that of Example 1, there was obtained 0.76 g of the title compound as colorless plates (recrystallized from ethyl acetate-hexane), $^1$H-NMR spectra data of the present compound is shown as below.

$^1$H-NMR (CDCl$_3$) δ: 0.88(3H, t, —CH$_2$—CH$_3$), 1.12 to 2.40(18H, m, CH$_2$), 3.19(2H, t, J=7 Hz, S—C$\overline{\underline{H}}_2$), 3.0 to 3.2 (1H, m, CH—COO), 3.39(3H, S, OCH$_3$), 4.14(1H, m, C$\underline{H}$—OCH$_3$), 7.21(2H, d, J=9 Hz, aromatic H), 7.52(2H, d, J=9 Hz, aromatic H), 8.69(2H, s, aromatic H)

EXAMPLE 58

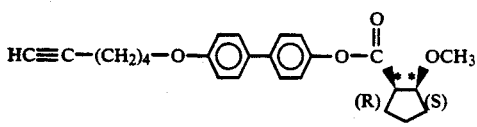

Using 0.53 g of cis-(1R,2S)-2-methoxycyclopentan-1-carboxylic chloride and 0.80 g of the skeletal compound, 4-(5-hexynyl)oxy-4-biphenol, and in the manner same as that of Example 1, there was obtained 0.92 g of the title compound as colorless plates (recrystallized from hot ethanol). $^1$H-NMR spectra data is shown as below.

$^1$H-NMR (CDCl$_3$) δ: 1.60 to 2.30(12H, m, —CH$_2$—), 2.35(1H, m, HC≡C—), 3.10(1H, m,

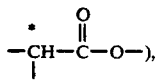

3.39(3H, S, —O—CH$_3$), 4.00(2H, t, J=6 Hz, —O—CH$_2$—), 4.10(1H, m, —C*H—OCH$_3$), 6.88 to 7.52(8H, m,

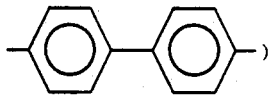

EXAMPLE 59

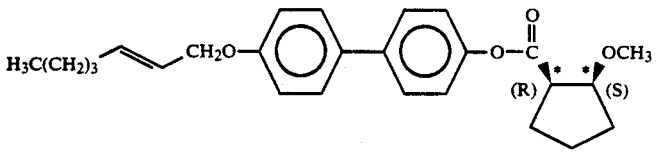

Using 0.50 g of cis-(1R,2S)-2-methoxycyclopentane-1-carboxychloride and 0.87 g of 4-(2-heptenyl)-4-biphenol and in the manner same as that of Example 1, there was obtained 0.64 g of the title compound as colorless needles (recrystallized from ethanol). $^1$H-NMR spectra data of the present compound is shown as below.

$^1$H-NMR (CDCl$_3$, 90 MHz) δ: 0.7 to 1.05(3H, m, CH$_3$), 1.05 to 2.5 (12H, m, CH$_2$), 2.9 to 3.35(1H, m, —OCH<), 3.39(3H, S, OCH$_3$), 4.0 to 4.26(1H, m,

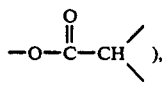

4.50(2H, d, g=4.7 Hz, allyl CH$_2$), 5.5 to 6.1(2H, m, vinyl H), 6.8 to 7.65(8H, m, aromatic H).

EXAMPLE 60

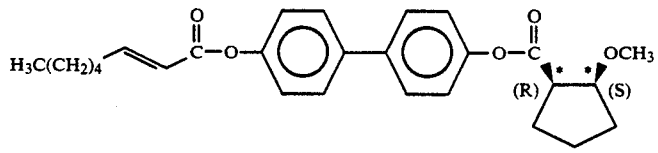

Using 0.50 g of cis-(1R,2S)-2-methoxycyclopentane-1-carboxylic acid chloride and 0.96 g of 4-(2-octenoyloxy)-4-biphenyl, and in the same procedure as in Example 1, there was obtained 0.92 g of the title compound as colorless needles (recrystallized from ethanol). $^1$H-NMR spectra data of the present compound is shown below.

$^1$H-NMR (CDCl$_3$, 90 MHz) δ: 0.75–1.05(3H, m, CH$_3$), 1.05–2.45 (14H, m, CH$_2$), 2.95–3.45(1H, m, OCH<), 3.40(3H, S, OCH$_3$), 3.9–4.3 (1H, m,

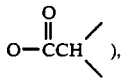

6.03(1H, d, g=15.5 Hz, vinyl H), 6.8–7.7(9H, m, aromatic H and vinyl H)

TABLE 1

| Example No. | Compound |
|---|---|
| 1 | 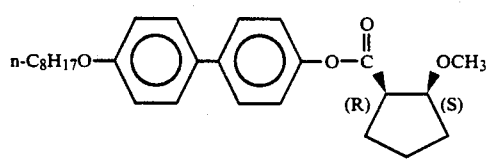 |

TABLE 1-continued
2 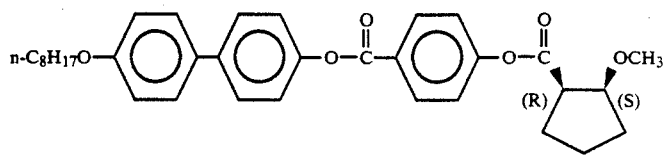
3 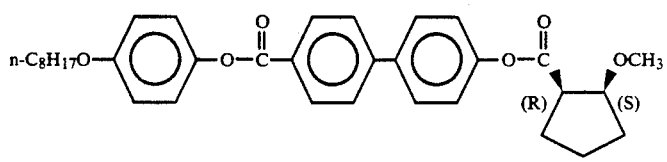
4 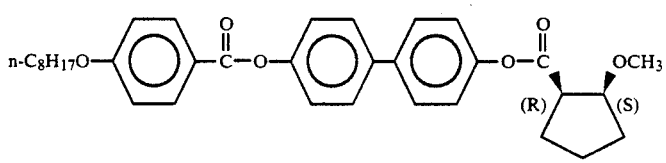
5 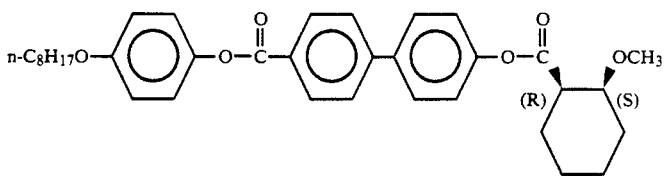
6 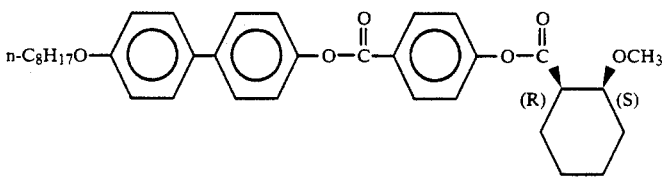
7 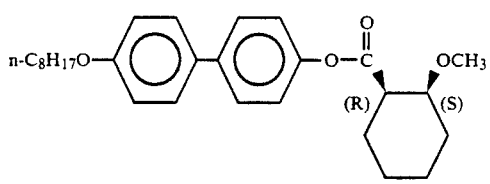
8 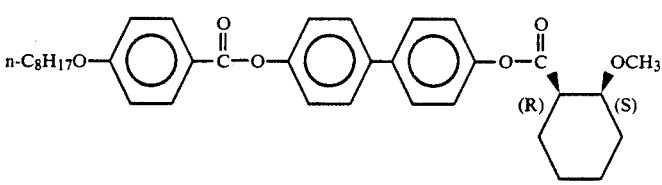
9 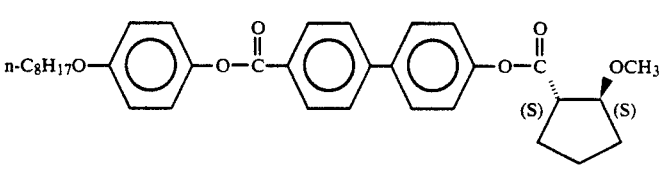
10 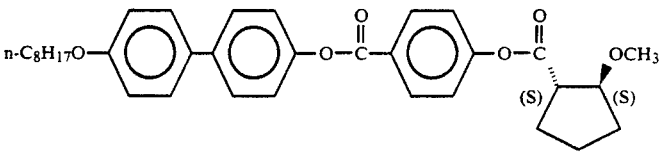

TABLE 1-continued
11 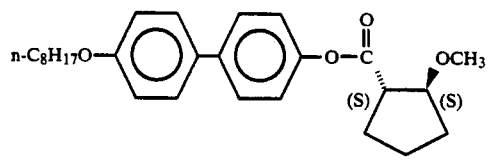
12 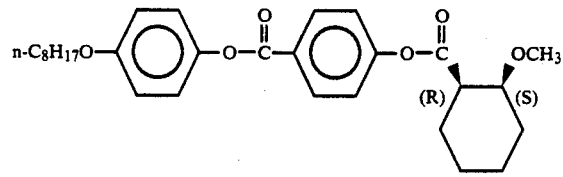
13 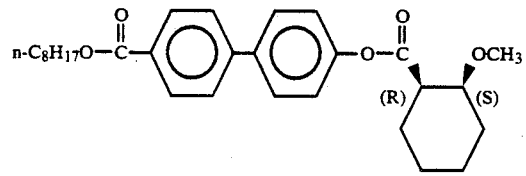
14 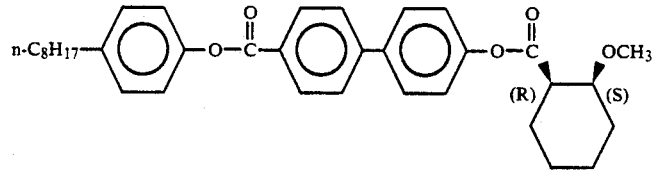
15 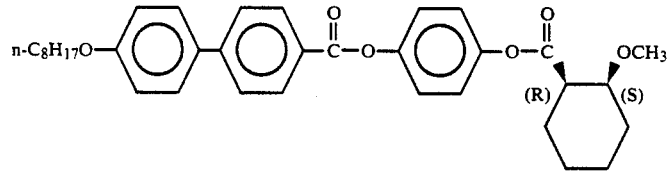
16 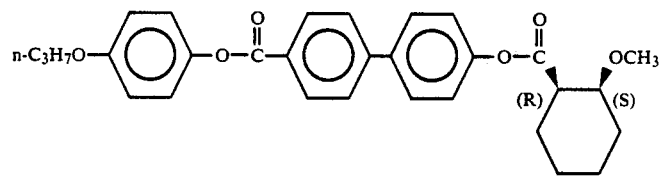
17 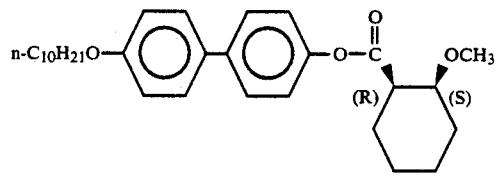
18 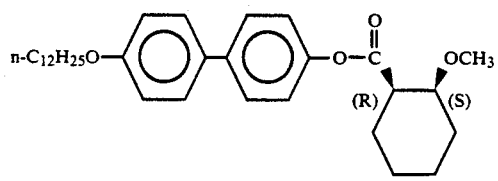

TABLE 1-continued
19 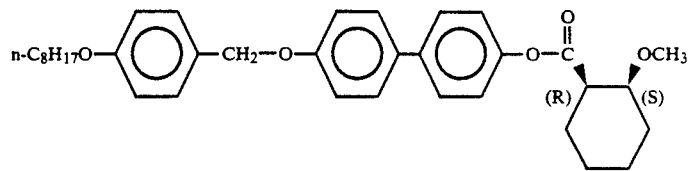
20 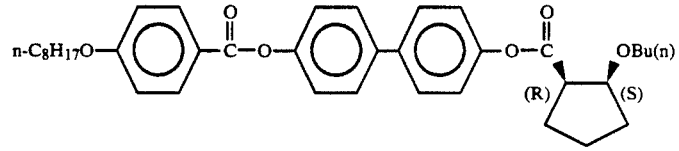
21 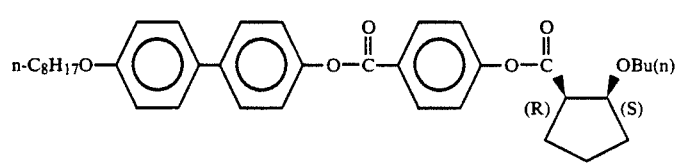
22 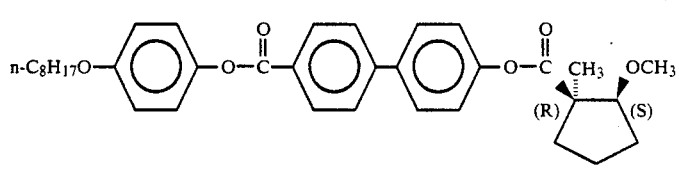
23 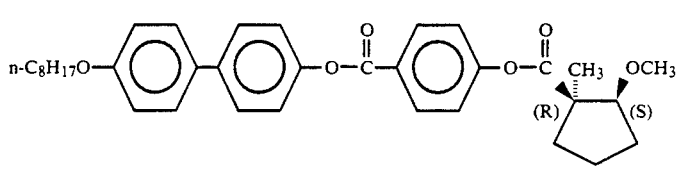
24 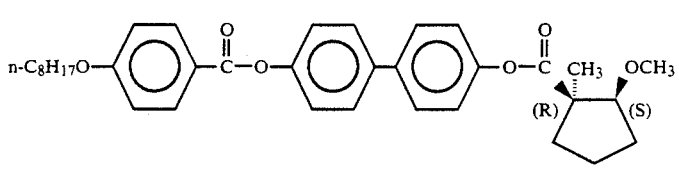
25 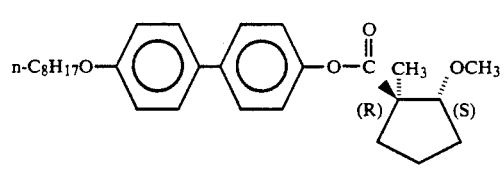
26 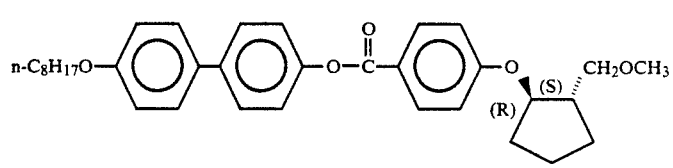
27 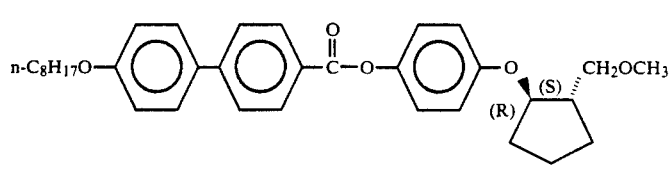

TABLE 1-continued
28 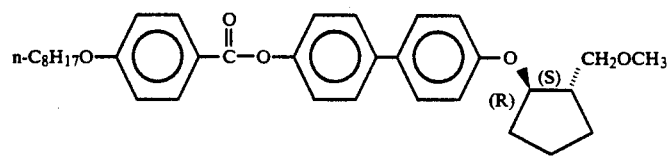
29 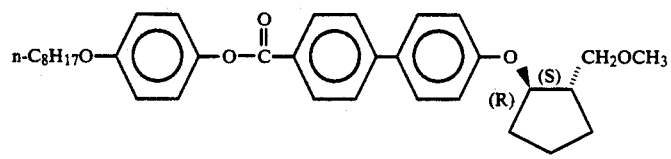
30 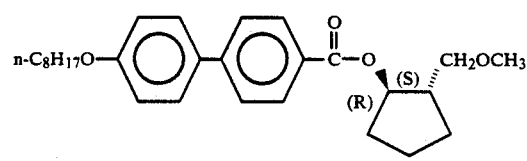
31 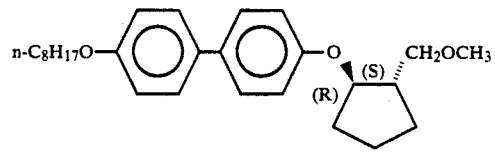
32 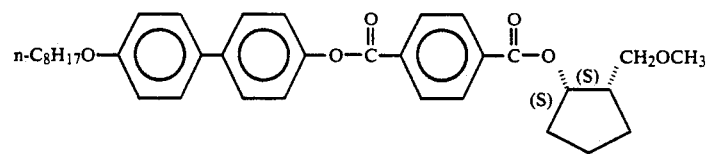
33 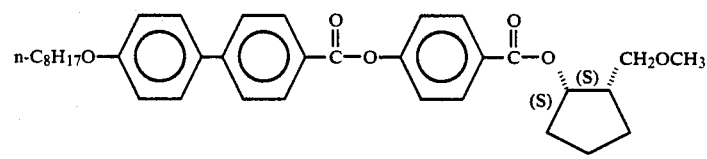
34 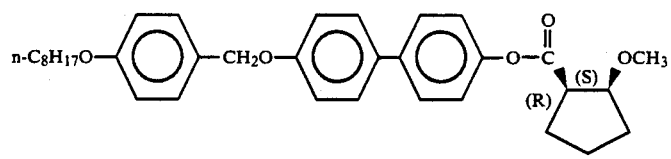
35 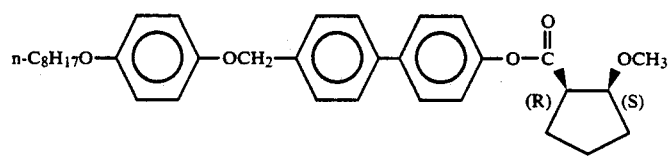
36 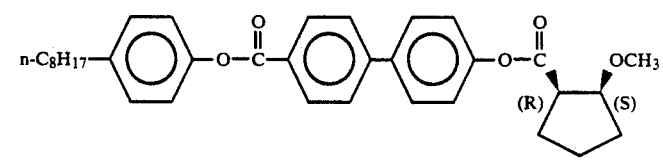

TABLE 1-continued
37 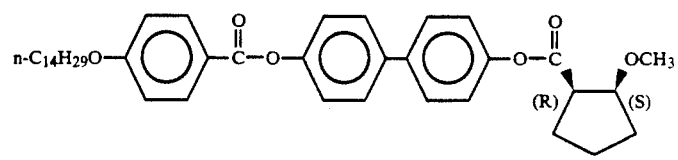
38 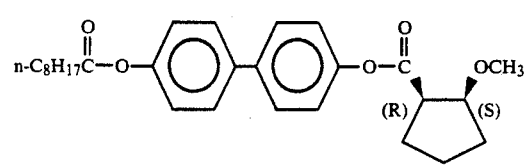
39 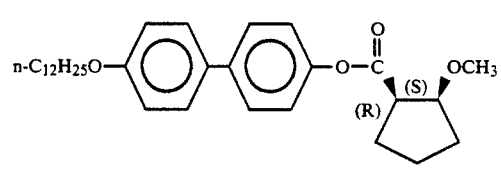
40 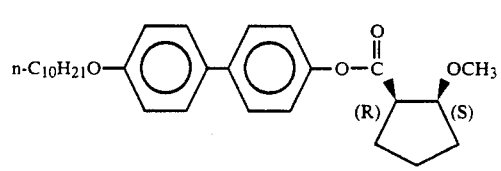
41 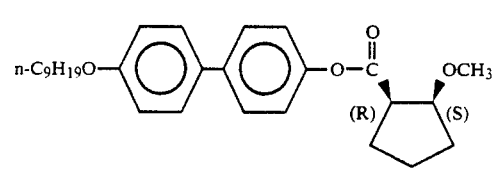
42 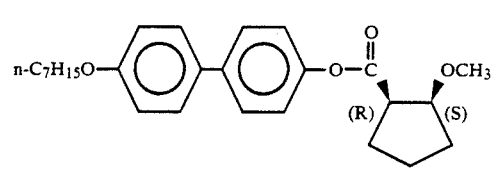
43 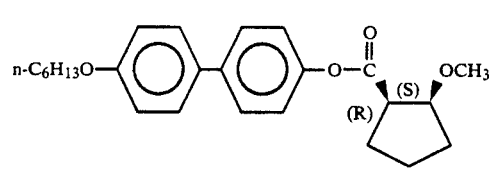
44 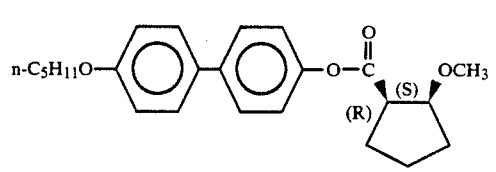
45 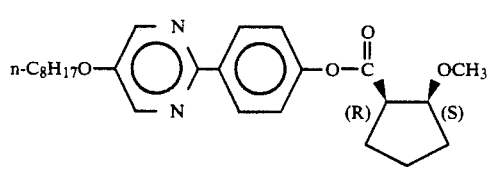

TABLE 1-continued
46 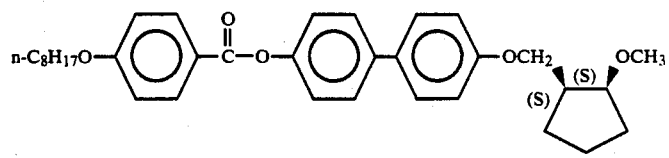
47 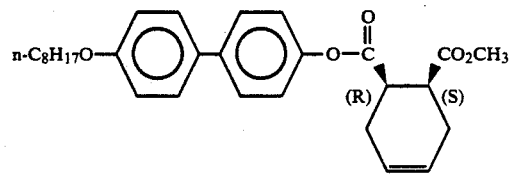
48 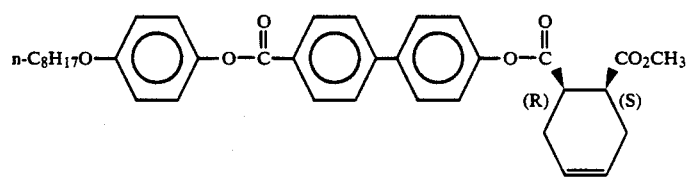
49 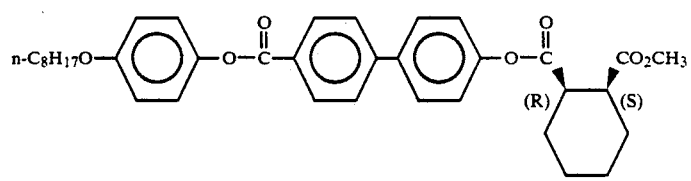
50 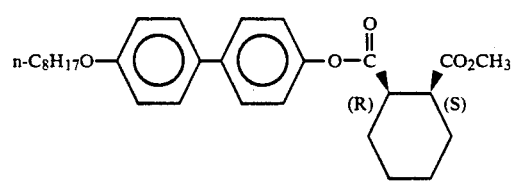
51 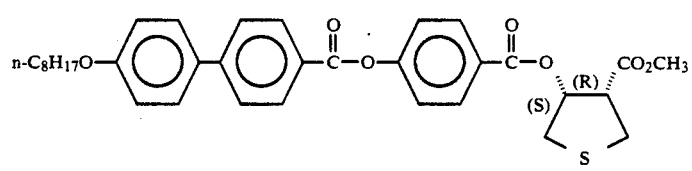
52 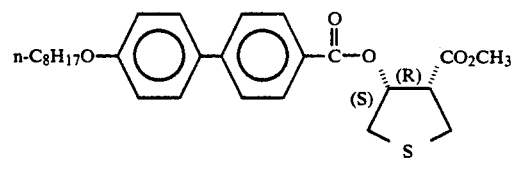
53 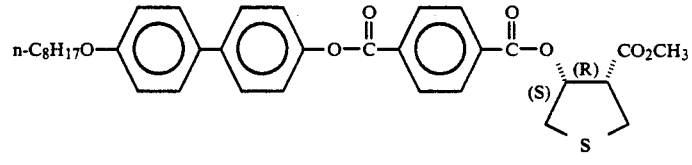
54 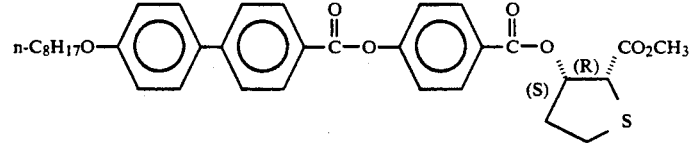

TABLE 1-continued

| | |
|---|---|
| 55 | 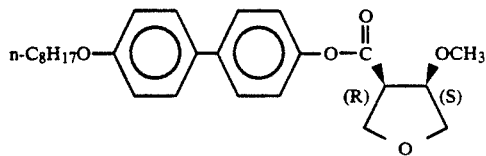 |
| 56 | 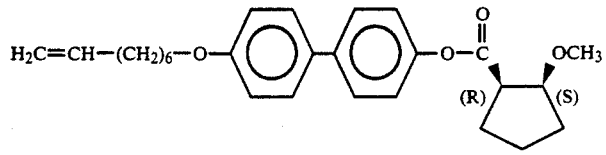 |
| 57 | 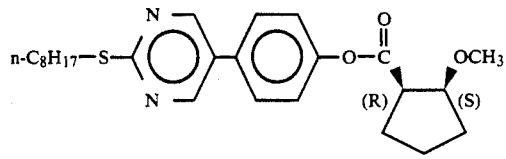 |
| 58 | 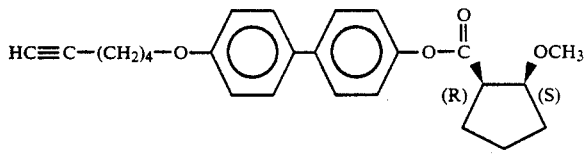 |
| 59 | 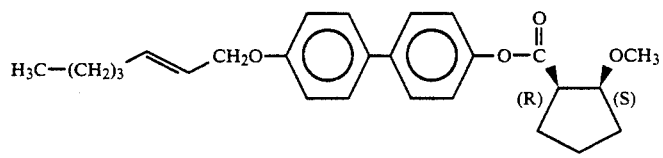 |
| 60 | 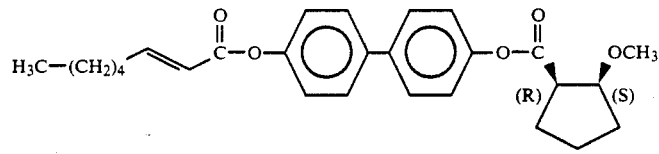 |

| Example No. | Phase transition temperature (°C.) | Spontaneous polarization (nC/cm$^2$) | Elemental analysis |
|---|---|---|---|
| 1 | K $\underset{31.5}{\overset{31.7}{\rightleftarrows}}$ Sc* $\overset{34.2}{\rightleftarrows}$ Ch $\overset{41.4}{\rightleftarrows}$ Iso | 180 | C$_{27}$H$_{36}$O$_4$ (424. 580) Calculated: C, 76.38; H, 8.55 Found: C, 76.67; H, 8.72 |
| 2 | K $\underset{97.1}{\overset{71.9}{\rightleftarrows}}$ Sc* $\underset{104.1}{\overset{102.7}{\rightleftarrows}}$ Ch $\overset{161.0}{\rightleftarrows}$ Iso | 270 | C$_{34}$H$_{40}$O$_6$ (544. 688) Calculated: C, 74.97; H, 7.40 Found: C, 75.14; H, 7.50 |
| 3 | K $\underset{69.0}{\overset{54.1}{\rightleftarrows}}$ Sc* $\overset{92.8}{\rightleftarrows}$ Ch $\overset{161.0}{\rightleftarrows}$ Iso | 180 | C$_{34}$H$_{40}$O$_6$ (544. 688) Calculated: C, 74.97; H, 7.40 Found: C, 74.96; H, 7.45 |
| 4 | K $\overset{64.5}{\rightarrow}$ Sc* $\overset{28.4}{\leftarrow}$ Si; Sc* $\overset{83.0}{\rightleftarrows}$ Ch $\overset{159.8}{\rightleftarrows}$ Iso | | C$_{34}$H$_{40}$O$_6$ (544. 688) Calculated: C, 74.97; H, 7.40 Found: C, 74.99; H, 7.36 |
| 5 | K $\underset{78.0}{\overset{39.7}{\rightleftarrows}}$ Sc* $\overset{104.9}{\rightleftarrows}$ Ch $\overset{168.8}{\rightleftarrows}$ Iso | 120 | C$_{35}$H$_{42}$O$_6$ (558. 71) Calculated: C, 75.24, H, 7.58 Found: C, 75.27; H, 7.58 |
| 6 | K $\underset{95.7}{\overset{75.5}{\rightleftarrows}}$ Sc* $\overset{104.5}{\rightleftarrows}$ Ch $\overset{168.9}{\rightleftarrows}$ Iso | 133 | C$_{35}$H$_{42}$O$_6$ (558. 71) Calculated: C, 75.24; H, 7.58 Found: C, 75.43; H, 7.66 |

TABLE 1-continued

| # | Phase transitions | | Formula / Analysis |
|---|---|---|---|
| 7 | K $\underset{46.2}{\overset{40.7}{\rightleftarrows}}$ Sc* $\overset{42.6}{\rightleftarrows}$ Ch $\underset{71.8-80.9}{\rightleftarrows}$ Iso | — | $C_{28}H_{38}O_4$<br>Calculated: C, 76.28; H, 8.73<br>Found: C, 76.57; H, 8.75 |
| 8 | K $\underset{78.6}{\overset{22.2}{\rightleftarrows}}$ Sc* $\overset{93.7}{\rightleftarrows}$ Ch $\underset{170.5}{\rightleftarrows}$ Iso | 160 (87° C., 82.7° C.) | $C_{35}H_{42}O_6$<br>Calculated: C, 75.24; H, 7.58<br>Found: C, 75.07; H, 7.62 |
| 9 | K $\underset{52.4}{\overset{33.6}{\rightleftarrows}}$ S$_1$ $\overset{41.7}{\rightleftarrows}$ Sc* $\underset{111.5}{\rightleftarrows}$ Ch $\underset{142.9}{\rightleftarrows}$ Iso | 14 | $C_{34}H_{40}O_6$ (544.688)<br>Calculated: C, 74.97; H, 7.40<br>Found: C, 75.21; H, 7.39 |
| 10 | K $\underset{98.0}{\overset{80.8}{\rightleftarrows}}$ S$_1$ $\overset{87.7}{\rightleftarrows}$ Sc* $\underset{119.3}{\rightleftarrows}$ Ch $\underset{147.4}{\rightleftarrows}$ Iso | 12 (105° C.) | $C_{34}H_{40}O_6$ (544.688)<br>Calculated: C, 74.97; H, 7.40<br>Found: C, 75.04; H, 7.50 |
| 11 | K $\underset{40.0}{\overset{34.5}{\rightleftarrows}}$ Sc* $\overset{37.4}{\rightleftarrows}$ S$_A$ $\overset{40.0}{\rightleftarrows}$ Iso | — | $C_{27}H_{36}O_4$ (424.580)<br>Calculated: C, 76.38; H, 8.55<br>Found: C, 76.28; H, 8.60 |
| 12 | K $\underset{86.9}{\overset{57.7}{\rightleftarrows}}$ Iso | — | $C_{29}H_{38}O_6$<br>Calculated: C, 72.17; H, 7.94<br>Found: C, 72.16; H, 7.96 |
| 13 | K $\underset{56.5}{\overset{}{\rightleftarrows}}$ S$_1$ $\overset{5.9}{\rightleftarrows}$ Iso | — | $C_{29}H_{38}O_5$<br>Calculated: C, 74.65; H, 8.21<br>Found: C, 74.37; H, 8.26 |
| 14 | K $\underset{80.9}{\overset{33.7}{\rightleftarrows}}$ S$_1$ $\overset{42.2}{\rightleftarrows}$ Sc* $\underset{88.0}{\rightleftarrows}$ Ch $\underset{146.2}{\rightleftarrows}$ Iso | 83 (81° C.) | $C_{35}H_{43}O_5$<br>Calculated: C, 77.32; H, 7.97<br>Found: C, 77.55; H, 7.85 |
| 15 | K $\underset{107.5}{\overset{85.1}{\rightleftarrows}}$ Sc* $\overset{108.2}{\rightleftarrows}$ Ch $\underset{169.9}{\rightleftarrows}$ Iso | ~0 | $C_{35}H_{42}O_6$<br>Calculated: C, 75.24; H, 7.58<br>Found: C, 75.30; H, 7.44 |
| 16 | K $\underset{132.3}{\overset{}{\rightleftarrows}}$ Ch $\underset{187.3}{\rightleftarrows}$ Iso | — | $C_{30}H_{32}O_6$<br>Calculated: C, 73.75; H, 6.60<br>Found: C, 73.98; H, 6.59 |
| 17 | K $\underset{48.9}{\overset{}{\rightleftarrows}}$ S$_1$ $\underset{59.2}{\rightleftarrows}$ Iso | — | $C_{30}H_{42}O_4$<br>Calculated: C, 77.21; H, 9.07<br>Found: C, 76.91; H, 9.10 |
| 18 | K $\underset{50.8}{\overset{48.0}{\rightleftarrows}}$ Ch $\overset{49.3}{\rightleftarrows}$ (S$_1$) $\underset{61.0}{\rightleftarrows}$ Iso | — | $C_{32}H_{46}O_4$<br>Calculated: C, 77.69; H, 9.37<br>Found: C, 77.90; H, 9.45 |
| 19 | $\overset{S_1\leftarrow 63.6}{K \underset{71.3}{\rightarrow} Sc^* \underset{131.3}{\overset{37.4}{\rightleftarrows}} Ch \underset{137.0}{\overset{40.0}{\rightleftarrows}} Iso}$ | 93 | $C_{35}H_{44}O_5$<br>Calculated: C, 77.17; H, 8.14<br>Found: C, 77.90; H, 8.12 |
| 20 | K $\underset{98.4}{\overset{}{\rightleftarrows}}$ S$_1$ $\overset{47.1}{\rightleftarrows}$ Sc* $\overset{59.6}{\rightleftarrows}$ Ch $\underset{108.5}{\rightleftarrows}$ Iso | — | $C_{37}H_{46}O_6$<br>Calculated: C, 75.74; H, 7.90<br>Found: C, 75.47; H, 7.89 |
| 21 | K $\underset{81.6}{\overset{60.0}{\rightleftarrows}}$ Sc* $\overset{83.0}{\rightleftarrows}$ Ch $\underset{110.0}{\rightleftarrows}$ Iso | — | $C_{37}H_{46}O_6$<br>Calculated: C, 75.74; H, 7.90<br>Found: C, 75.64; H, 7.89 |
| 22 | K $\underset{62.2}{\overset{}{\rightleftarrows}}$ S$_1$ $\underset{72.3}{\overset{71.8}{\rightleftarrows}}$ Sc* $\overset{72.0}{\rightleftarrows}$ Ch $\underset{99.3-102.0}{\rightleftarrows}$ Iso | — | $C_{35}H_{42}O_6$ (558.715)<br>Calculated: C, 75.24; H, 7.58<br>Found: C, 75.21; H, 7.57 |
| 23 | K $\underset{73.8}{\overset{33.6}{\rightleftarrows}}$ S$_1$ $\overset{38.7}{\rightleftarrows}$ S$_A$ $\underset{93.8}{\rightleftarrows}$ Ch $\underset{107.2}{\rightleftarrows}$ Iso | — | $C_{35}H_{42}O_6$ (558.715)<br>Calculated: C, 75.24; H, 7.57<br>Found: C, 75.42; H, 7.61 |
| 24 | K $\underset{77.4}{\overset{47.2}{\rightleftarrows}}$ S$_1$ $\overset{72.3}{\rightleftarrows}$ Ch $\underset{106.4}{\rightleftarrows}$ Iso | — | $C_{35}H_{42}O_6$ (558.715)<br>Calculated: C, 75.24; H, 7.58<br>Found: C, 75.27; H, 7.58 |
| 25 | K $\underset{30.2}{\overset{}{\rightleftarrows}}$ Iso | — | $C_{28}H_{38}O_4$ (438.607)<br>Calculated: C, 76.88; H, 8.73<br>Found: C, 76.81; H, 8.86 |
| 26 | K $\underset{71.0}{\overset{}{\rightleftarrows}}$ Ch $\underset{92.9}{\rightleftarrows}$ Iso | — | $C_{34}H_{42}O_5$<br>Calculated: C, 76.95; H, 7.98<br>Found: C, 77.21; H, 8.00 |

TABLE 1-continued

| | | | |
|---|---|---|---|
| 27 | K $\underset{80.9}{\overset{38.0}{\rightleftarrows}}$ S$_1$ $\underset{83.3}{\overset{61.0}{\rightleftarrows}}$ Sc* $\overset{79.7}{\rightleftarrows}$ S$_A$ $\underset{121.0}{\rightleftarrows}$ Iso | 6 | C$_{34}$H$_{42}$O$_5$<br>Calculated: C, 76.95; H, 7.98<br>Found: C, 77.21; H, 8.00 |
| 28 | K $\underset{77.5}{\overset{59.1}{\rightleftarrows}}$ S$_1$ $\overset{75.5}{\rightleftarrows}$ Ch $\underset{97.1}{\rightleftarrows}$ Iso | — | C$_{34}$H$_{42}$O$_5$<br>Calculated: C, 76.95; H, 7.98<br>Found: C, 77.06; H, 7.97 |
| 29 | K $\underset{73.8}{\overset{\sim35}{\rightleftarrows}}$ Sc* $\overset{42.1}{\rightleftarrows}$ Ch $\underset{87.4}{\rightleftarrows}$ Iso | — | C$_{34}$H$_{42}$O$_5$<br>Calculated: C, 76.95; H, 7.98<br>Found: C, 77.01; H, 7.93 |
| 30 | K $\underset{48.8}{\overset{17.6}{\rightleftarrows}}$ Iso | — | C$_{28}$H$_{38}$O$_4$<br>Calculated: C, 76.68; H, 8.73<br>Found: C, 76.93; H, 8.80 |
| 31 | K $\underset{34.8}{\overset{18.4}{\rightleftarrows}}$ Iso | — | C$_{27}$H$_{38}$O$_3$<br>Calculated: C, 78.98; H, 9.33<br>Found: C, 79.08; H, 9.35 |
| 32 | K $\overset{72.1}{\rightleftarrows}$ S$_1$ $\overset{\sim84.3}{\rightleftarrows}$ Iso | — | C$_{35}$H$_{42}$O$_6$<br>Calculated: C, 75.24; H, 7.58<br>Found: C, 73.72; H, 6.95 |
| 33 | K $\underset{84-104}{\overset{84.0}{\rightleftarrows}}$ Sc* $\overset{100.6}{\rightleftarrows}$ Ch $\underset{103.0}{\rightleftarrows}$ Iso | ~0 | C$_{35}$H$_{42}$O$_6$<br>Calculated: C, 75.24; H, 7.58<br>Found: C, 75.17; H, 7.57 |
| 34 | K $\underset{85.2}{\overset{60.3}{\rightleftarrows}}$ S$_1$ $\overset{82.8}{\rightleftarrows}$ Sc* $\underset{124.4}{\rightleftarrows}$ Ch $\overset{128.6}{\rightleftarrows}$ Iso | ~0 | C$_{34}$H$_{42}$O$_5$ (530. 705)<br>Calculated: C, 76.95; H, 7.98<br>Found: C, 76.78; H, 7.93 |
| 35 | K $\underset{90.4}{\rightleftarrows}$ Sc* $\underset{114.7}{\rightleftarrows}$ Ch $\underset{122.1}{\rightleftarrows}$ Iso | 200 | C$_{34}$H$_{42}$O$_5$ (530. 705)<br>Calculated: C, 76.95; H, 7.98<br>Found: C, 76.88; H, 7.97 |
| 36 | K $\underset{85.3}{\overset{49.4}{\rightleftarrows}}$ Sc* $\overset{69.6}{\rightleftarrows}$ Ch $\underset{132.4}{\rightleftarrows}$ Iso | 156 | C$_{34}$H$_{40}$O$_5$ (528. 689)<br>Calculated: C, 77.24; H, 7.63<br>Found: C, 77.32; H, 7.63 |
| 37 | K $\underset{84.0}{\overset{77.7}{\rightleftarrows}}$ Sc* $\underset{108.2}{\rightleftarrows}$ Ch $\underset{114.1}{\rightleftarrows}$ Iso | ~0 | C$_{40}$H$_{52}$O$_6$ (628. 849)<br>Calculated: C, 76.40; H, 8.33<br>Found: C, 76.59; H, 8.45 |
| 38 | K $\underset{43.6}{\overset{40.0}{\rightleftarrows}}$ Sc* $\overset{41.5}{\rightleftarrows}$ Iso | 180<br>(40° C.) | C$_{28}$H$_{36}$O$_5$ (452. 59)<br>Calculated: C, 74.31; H, 8.02<br>Found: C, 74.48; H, 8.06 |
| 39 | K $\underset{57.0}{\overset{44.7}{\rightleftarrows}}$ S$_1$ $\overset{50.5}{\rightleftarrows}$ Iso | — | C$_{31}$H$_{44}$O$_4$ (480. 68)<br>Calculated: C, 77.46; H, 9.23<br>Found: C, 77.44; H, 9.28 |
| 40 | K $\underset{46.9}{\overset{39.2}{\rightleftarrows}}$ S$_1$ $\overset{46.9}{\rightleftarrows}$ Iso | — | C$_{29}$H$_{40}$O$_4$ (452. 63)<br>Calculated: C, 76.95; H, 8.91<br>Found: C, 77.01; H, 8.98 |
| 41 | K $\underset{54.2}{\overset{30.9}{\rightleftarrows}}$ S$_1$ $\overset{30.9}{\rightleftarrows}$ Sc* $\overset{34.2}{\rightleftarrows}$ Iso | — | C$_{28}$H$_{38}$O$_4$ (438. 60)<br>Calculated: C, 76.68; H, 8.73<br>Found: C, 76.67; H, 8.66 |
| 42 | K $\underset{38.2}{\overset{31.3}{\rightleftarrows}}$ Iso | — | C$_{26}$H$_{34}$O$_4$ (410. 55)<br>Calculated: C, 76.06; H, 8.35<br>Found: C, 76.04; H, 8.35 |
| 43 | K $\underset{53.1}{\overset{38.1}{\rightleftarrows}}$ Iso | — | C$_{25}$H$_{32}$O$_4$ (396. 52)<br>Calculated: C, 75.73; H, 8.13<br>Found: C, 75.72; H, 8.17 |
| 44 | K $\underset{76.8}{\overset{43.1}{\rightleftarrows}}$ Iso | — | C$_{24}$H$_{30}$O$_4$ (382. 50)<br>Calculated: C, 75.36; H, 7.91<br>Found: C, 75.28; H, 7.83 |
| 45 | K $\underset{77.7}{\overset{54.8}{\rightleftarrows}}$ Iso | — | C$_{25}$H$_{34}$N$_2$O$_5$ (426. 55)<br>Calculated: C, 70.40; H, 8.03<br>Found: C, 70.30; H, 8.09 |
| 46 | K $\underset{79.9}{\overset{41.3}{\rightleftarrows}}$ Sc* $\overset{82.4}{\rightleftarrows}$ Ch $\underset{143.7}{\rightleftarrows}$ Iso | ~0 | C$_{34}$H$_{42}$O$_5$ (530. 705)<br>Calculated: C, 76.95; H, 7.98<br>Found: C, 76.90; H, 8.04 |

TABLE 1-continued

| | | | |
|---|---|---|---|
| 47 | K $\xrightleftharpoons[79.8]{21.1}$ Iso | — | $C_{29}H_{36}O_5$ (464. 602)<br>Calculated: C, 74.97; H, 7.81<br>Found: C, 75.16; H, 7.80 |
| 48 | K $\xrightleftharpoons[95.2]{48.6}$ $S_A$ $\xrightleftharpoons{67.0}$ Ch $\xrightleftharpoons{92.0}$ Iso | — | $C_{36}H_{40}O_7$ (584. 709)<br>Calculated: C, 73.95; H, 8.90<br>Found: C, 73.99; H, 6.93 |
| 49 | K $\xrightleftharpoons[89.6]{23.6}$ $S_1{}^*$ $\xrightleftharpoons{51.3}$ Sc* $\xrightleftharpoons{60.4}$ Ch $\xrightleftharpoons{89.6}$ Iso | — | $C_{36}H_{42}O_7$ (586. 725)<br>Calculated: C, 73.70; H, 7.22<br>Found: C, 73.60; H, 7.13 |
| 50 | K $\xrightleftharpoons[74.4]{29.6}$ Iso | — | $C_{29}H_{38}O_5$ (466. 618)<br>Calculated: C, 74.65; H, 8.21<br>Found: C, 74.59; H, 7.96 |
| 51 | K $\xrightleftharpoons[101.6]{76.5}$ Sc* $\xrightleftharpoons{81.6}$ Iso | — | $C_{34}H_{38}O_7S$ (590. 738)<br>Calculated: C, 69.13; H, 6.48<br>Found: C, 68.97; H, 6.38 |
| 52 | K $\xrightarrow[47.6]{}$ $S_1$ $\xrightarrow[72.5]{}$ Iso, $\searrow 84.0$ | — | $C_{27}H_{34}O_5S$ (470. 630)<br>Calculated: C, 68.91; H, 7.28<br>Found: C, 68.95; H, 7.15 |
| 53 | K $\xrightleftharpoons[120.9]{}$ Iso | — | $C_{34}H_{38}O_7S$ (590. 738)<br>Calculated: C, 69.13; H, 6.48<br>Found: C, 68.89; H, 6.36 |
| 54 | K $\xrightleftharpoons[84.7]{38}$ $S_2$ $\xrightleftharpoons{85.1}$ $S_1$ $\xrightleftharpoons{97.1}$ Ch $\xrightleftharpoons{100.6}$ Iso | — | $C_{34}H_{38}O_7S$ (590. 738)<br>Calculated: C, 69.13; H, 6.48<br>Found: C, 69.16; H, 6.36 |
| 55 | K $\xrightleftharpoons[76.6]{57.7}$ Iso | — | — |
| 56 | K $\xrightleftharpoons[26.7]{1.2}$ Sc* $\xrightleftharpoons{25.1}$ Iso | 298 | $C_{27}H_{34}O_4$ (422. 565)<br>Calculated: C, 69.55; H, 7.30<br>Found: C, 69.50; H, 7.34 |
| 57 | K $\xrightleftharpoons[87.6]{60.1}$ Iso | — | $C_{25}H_{24}N_2O_3S$ (442. 615)<br>Calculated: C, 67.84; H, 7.74; N, 6.33<br>Found: C, 67.89; H, 7.81; N, 6.28 |
| 58 | K $\xrightleftharpoons[61.0]{27.5}$ Iso | — | $C_{25}H_{28}O_4$ (392. 493)<br>Calculated: C, 76.50; H, 7.19<br>Found: C, 76.67; H, 7.26 |
| 59 | K $\xrightleftharpoons[59.7]{48.0}$ Iso | — | $C_{26}H_{32}O_4$ (408. 538)<br>Calculated: C, 76.44; H, 7.90<br>Found: C, 76.53; H, 7.94 |
| 60 | K $\xrightleftharpoons[99.1]{69.3}$ Iso | — | $C_{27}H_{32}O_5$ (436. 548)<br>Calculated: C, 74.29; H, 7.39<br>Found: C, 74.31; H, 7.46 |

APPLICATION EXAMPLE 1

The optically active compounds of the present invention shown in Table 1 were incorporated into the known ferroelectric liquid crystal compounds A to C (hereinafter referred to as mother liquid crystals) shown in Table 2, in given amounts, to prepare liquid crystal compositions shown in Table 3 each containing an optically active compound of the present invention.

These compositions and the mother liquid crystals A–C were measured for spontaneous polarization. The results are shown in Table 3.

In Table 3, the values of spontaneous polarization are those at a temperature lower by 10° C. than the upper limit temperature of chiral smectic C phase.

TABLE 2

| Mother liquid crystal | Chemical structure |
|---|---|
| A | $C_8H_{17}O$—〈 〉—CH=N—〈 〉—$CO_2CH_2\overset{*}{C}HC_2H_5$<br>                                                                    $\|$<br>                                                                   $CH_3$<br><br>$C_8H_{17}O$—〈 〉—〈 〉—$CO_2CH_2\overset{*}{C}HC_2H_5$<br>                                                         $\|$<br>                                                        $CH_3$<br>(equimolar mixture) |

TABLE 2-continued

| Mother liquid crystal | Chemical structure |
|---|---|
| B | $C_7H_{15}O$—⟨⟩—$CO_2$—⟨⟩—$O(CH_2)_3\overset{*}{C}HC_2H_5$ <br> $\phantom{xxxxxxxxxxxxxxxxxxxxxxxxxxxx}CH_3$ |
| C | $C_7H_{15}O$—⟨⟩—$OCO$—⟨⟩—$O(CH_2)_3\overset{*}{C}HC_2H_5$ <br> $\phantom{xxxxxxxxxxxxxxxxxxxxxxxxxxxx}CH_3$ <br><br> $C_7H_{15}O$—⟨⟩—$OCO$—⟨⟩—$O(CH_2)_5\overset{*}{C}HC_2H_5$ <br> $\phantom{xxxxxxxxxxxxxxxxxxxxxxxxxxxx}CH_3$ <br> (equimolar mixture) |

TABLE 3

| Mother liquid crystal | Optically active compound I of this invention | | Spontaneous polarization (nC/cm²) |
|---|---|---|---|
| | Example No. | Amount used (wt. %) | |
| A | — | — | 4 |
| A | 2 | 10 | 30 |
| A | 3 | 10 | 26 |
| A | 8 | 20 | 34 |
| B | — | — | <1 |
| B | 1 | 20 | 32 |
| B | 2 | 10 | 26 |
| B | 5 | 10 | 13 |
| B | 21 | 10 | 11 |
| B | 38 | 20 | 25 |
| C | — | — | <1 |
| C | 1 | 30 | 51 |
| C | 6 | 10 | 15 |
| C | 14 | 20 | 15 |

Each liquid crystal composition shown in Table 3 was sealed in a cell constituted by (a) two glass substrates each with a transparent electrode, obtained by spin coating of a polyimide and subsequent rubbing and (b) a spacer consisting of a polyethylene terephthalate film of 6 μm in thickness, whereby liquid crystal devices were prepared. A rectangular wave (40 Vp-p) was applied to the liquid crystal devices at room temperature, and their optical responses were observed by a polarizing microscope. The devices containing the compositions using the optically active compounds of the present invention gave an optical contrast and showed a very good optical response, while the devices containing the mother liquid crystal B or C alone showed no clear optical response.

APPLICATION EXAMPLE 2

The optically active compounds of the present invention shown in Table 4 were incorporated into the mother liquid crystal A, and the resulting compositions were measured for spontaneous polarization. The results are shown in Table 4. In Table 4, the values of spontaneous polarization are those at a temperature 10° C. lower than the upper limit of Sc* phase.

TABLE 4

| Mother liquid crystal | Optically active compound I of this invention | | Spontaneous polarization (nC/cm²) |
|---|---|---|---|
| | Example No. | Amount used (wt. %) | |
| A | 51 | 10 | 15 |
| A | 51 | 20 | 28 |
| A | 51 | 30 | 41 |
| A | 52 | 10 | 13 |
| A | 47 | 30 | 44 |
| A | 48 | 20 | 25 |
| A | — | — | <1 |

Mother liquid crystal A:

$C_7H_{15}O$—⟨⟩—$OCO$—⟨⟩—$O(CH_2)_3\overset{*}{C}HC_2H_5$
$\phantom{xxxxxxxxxxxxxxxxxxxxxxxxxxxxxx}CH_3$ $C_7H_{15}O$—⟨⟩—$OCO$—⟨⟩—$O(CH_2)_5\overset{*}{C}HC_2H_5$
$\phantom{xxxxxxxxxxxxxxxxxxxxxxxxxxxxxx}CH_3$
(equimolar mixture)

The composition shown in the uppermost column of Table 4 was sealed in a cell constituted by (a) two glass substrates each with a transparent electrode, obtained by spin coating of a polyimide and subsequent rubbing and (b) a spacer consisting of a polyethylene terephthalate film of 6 μm in thickness, whereby a liquid crystal display device shown in FIG. 1 was prepared. A rectangular wave (40 Vp-p, 10 Hz) was applied to the device at room temperature and observation was made using a polarizing microscope. An optical response was observed. Meanwhile, a device containing the mother liquid crystal shown in the lowermost column of Table 4 showed no optical response even when the applied voltage was increased to 50 Vp-p.

As is clear from Examples and Application Examples, the present invention provides liquid crystal compounds and liquid crystal compositions having a large spontaneous polarization and showing a chiral smectic C phase. The liquid crystal compounds of the present invention can be effectively used to provide a liquid crystal composition of significantly increased spontaneous polarization. Accordingly, the optically active compounds of the present invention and the liquid crystal compositions containing these compounds are useful as a liquid crystal to be employed in optical modulators such as liquid crystal display apparatuses and can provide such apparatuses having excellent capabilities in response, etc.

What is claimed is:

1. Optically active compounds represented by the general formula

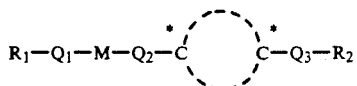

wherein $R_1$ is an alkyl group, an alkenyl group or an alkynyl group each of 3-14 carbon atoms; $R_2$ is an alkyl group of 1-10 carbon atoms, an alkenyl group of 2-10 carbon atoms or an alkynyl group of 2-10 carbon atoms;

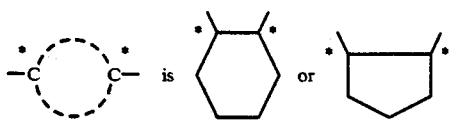 is 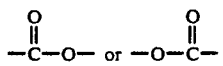

$Q_1$ is a single bond, a (thio)ether group, a carboxylic acid ester group, a carbonyl group or a carbonyldioxy group; $Q_2$ and $Q_3$ are independently, a (thio)ether group, a carboxylic acid ester group, a carbonyl group, a carbonyldioxy group or a methyleneoxy group; M is

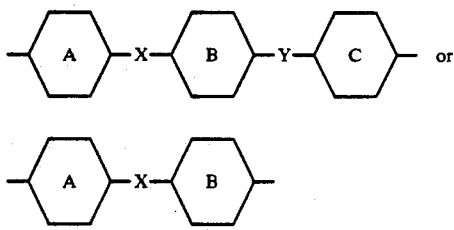

(X and Y are independently a single bond, a carboxylic acid ester group, a methylenoxy group or an ethylene group, and

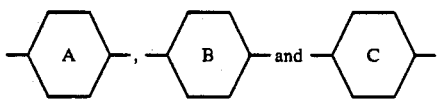

are independently a six-membered ring-1,4-diyl group which may contain 1-2 oxygen or nitrogen atoms as ring-forming atoms); the carbon atoms with the asterisk (*) denote asymmetric carbon atoms.

2. Optically active compounds according to claim 1, wherein the two polar groups bonding to the asymmetric carbon atoms of the five- or six-membered ring represented by

are in the same direction conformation.

3. Optically active compounds according to claim 1, wherein the asymmetric carbon atoms are adjacent to each other and $Q_2$ and $Q_3$ each bonding to either of the asymmetric carbon atoms are in a cis form.

4. Optically active compounds according to claim 1, wherein $R_1$ is an alkyl group of 6-11 carbon atoms and $R_2$ is an alkyl group of 1-8 carbon atoms.

5. Optically active compounds according to claim 1, wherein $Q_1$ is a single bond, a (thio)ether group or a

ester group; $Q_2$ is a

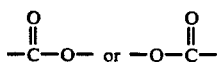

ester group or an ether group; $Q_3$ is a (thio)ether group or a

ester group.

6. Optically active compounds according to claim 1, wherein M is

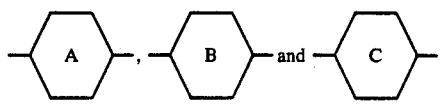

one of X and Y is a single bond and the other is a carboxylic acid ester group; all of

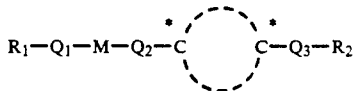

are p-phenylene, or one of them is 2,5-pyrimidinediyl.

7. Liquid crystal compositions comprising at least one of the optically active compounds according to any one of claims 1-6 and optionally a mother liquid crystal.

8. Liquid crystal optical modulators comprising at least one pair of substrates and one of the liquid crystal compositions according to claim 7 placed between the substrates.

9. An optically active compound of the formula:

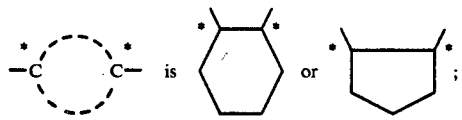

wherein
$R_1$ is a straight chain alkyl group of 6 to 12 carbon atoms, a straight chain alkenyl group of 6 to 12 carbon atoms or a straight chain alkynyl group of 6 to 12 carbon atoms;
$R_2$ is a straight chain alkyl group of 1 to 8 carbon atoms;

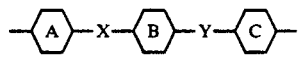

$Q_1$ is a single bond, a (thio)ether group or a —C(=O)—O— ester group;
$Q_2$ is a —C(=O)—O— ester group, a —O—C(=O)— ester group or an ether group;
$Q_3$ is a (thio)ether group, a —C(=O)—)—O— ester group or a —O—C(=O)— ester group;
M is

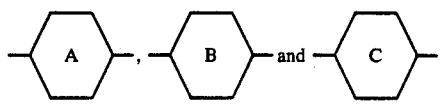

(in which one of X and Y is a single bond and the other of X and Y is a carboxylic acid ester bond) or

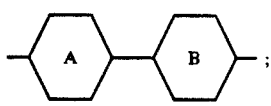

all of the rings A to C are p-phenylene or one of the rings is 2,5-pyrimidinedlyl; and

*-marked carbon atoms are each an asymmetric carbon atom.

10. An optically active compound according to claim 9 in which

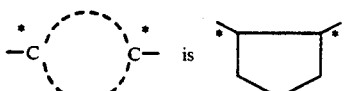

11. An optically active compound according to claim 10, which is

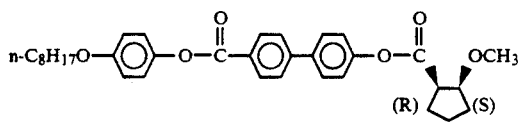

12. An optically active compound according to claim 10 which is

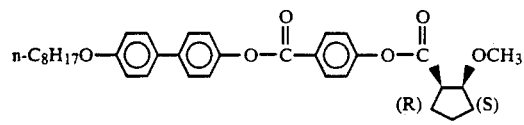

13. An optically active compound according to claim 10 which is

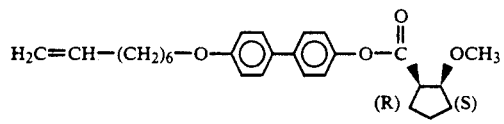

14. An optically active compound according to claim 9 in which

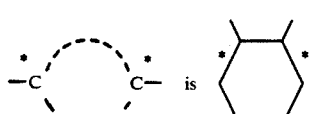

15. An optically active compound according to claim 14 which is

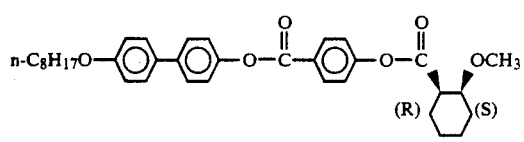

16. An optically active compound according to claim 14 which is

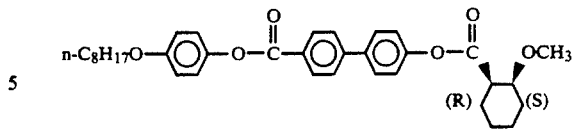

17. An optically active compound according to claim 10, which is represented by the formula:

wherein $R_1$ is a straight chain alkyl group of 6 to 12 carbon atoms, a straight chain alkenyl group of 6 to 12 carbon atoms or a straight chain alkynyl group of 6 to 12 carbon atoms;

$R_2$ is a straight chain alkyl group of 1 to 8 carbon atoms;

$Q_1$ is a single bond, an ether group or a —C(=O)—O— ester group;

$Q_2$ is a —C(=O)—O— ester group, a —O—C(=O)— ester group or an ether group;

$Q_3$ is an ether group, a —C(=O)—O— ester group or a —O—C(=O)— ester group;

M is

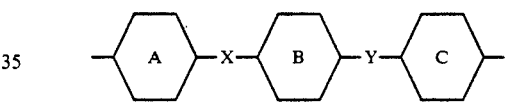

(in which one of X and Y is a single bond and the other of X and Y is a carboxylic acid ester bond) or

all of the rings A to C are p-phenylene or one of the rings is 2,5-pyrimidinedlyl; and

*-marked carbon atoms are each an asymmetric carbon atom.

18. An optically active compound according to claim 17, wherein all of the rings A to C are p-phenylene.

19. An optically active compound according to claim 17, wherein M is

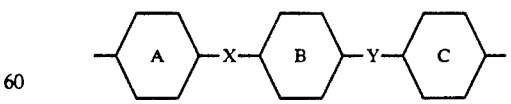

(in which one of X and Y is a single bond and the other of X and Y is a carboxylic acid ester bond).

20. An optically active compound according to claim 19, wherein all of the rings A to C are p-phenylene.

21. An optically active compound according to claim 17, wherein M is

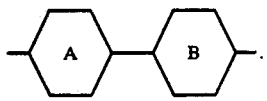

22. An optically active compound according to claim 19, wherein both of the rings A and B are p-phenylene.

23. An optically active compound according to claim 10, which is represented by the formula:

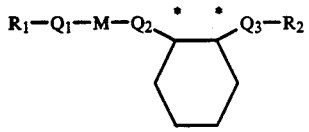

wherein
$R_1$ is a straight chain alkyl group of 6 to 12 carbon atoms, a straight chain alkenyl group of 6 to 12 carbon atoms or a straight chain alkynyl group of 6 to 12 carbon atoms;
$R_2$ is a straight chain alkyl group of 1 to 8 carbon atoms;
$Q_1$ is a single bond, an ether group or a —C(=O)—O— ester group;
$Q_2$ is a —C(=O)—O— ester group, a —O—C(=O)— ester group or an ether group;
$Q_3$ is an ether group, a —C(=O)—O— ester group or a —O—C(=O)— ester group;
M is

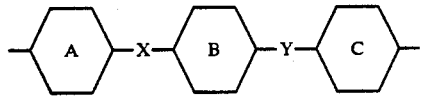

(in which one of X and Y is a single bond and the other of X and Y is a carboxylic acid ester bond) or

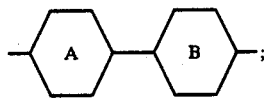

all of the rings A to C are p-phenylene or one of the rings is 2,5-pyrimidinedlyl; and
*-marked carbon atoms are each an asymmetric carbon atom.

24. An optically active compound according to claim 23, wherein all of the rings A to C are p-phenylene.

25. An optically active compound according to claim 23, wherein M is

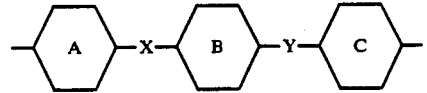

(in which one of X and Y is a single bond and the other of X and Y is a carboxylic acid ester bond).

26. An optically active compound according to claim 25, wherein all of the rings A to C are p-phenylene.

27. An optically active compound according to claim 23, wherein M is

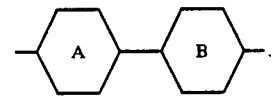

28. An optically active compound according to claim 27, wherein both of the rings A and B are p-phenylene.

* * * * *